(12) United States Patent
Chin et al.

(10) Patent No.: US 11,491,178 B2
(45) Date of Patent: Nov. 8, 2022

(54) CHITOSAN COVALENTLY LINKED WITH SMALL MOLECULE INTEGRIN ANTAGONIST FOR TARGETED DELIVERY

(71) Applicant: Hoffmann-La Roche Inc., Nutley, NJ (US)

(72) Inventors: Jayne Chin, Warren, NJ (US); Robert Alan Goodnow, Jr., Gillette, NJ (US); Matthew Michael Hamilton, Hackettstown, NJ (US); Achyutharao Sidduri, Livingston, NJ (US)

(73) Assignee: HOFFMANN-LA ROCHE, INC., Nutley, NJ (US)

( * ) Notice: Subject to any disclaimer, the term of this patent is extended or adjusted under 35 U.S.C. 154(b) by 0 days.

(21) Appl. No.: 15/812,406

(22) Filed: Nov. 14, 2017

(65) Prior Publication Data

US 2018/0099005 A1 Apr. 12, 2018

Related U.S. Application Data

(63) Continuation of application No. 14/373,669, filed as application No. PCT/EP2013/051279 on Jan. 24, 2013, now abandoned.

(60) Provisional application No. 61/591,293, filed on Jan. 27, 2012, provisional application No. 61/670,665, filed on Jul. 12, 2012.

(51) Int. Cl.
| | |
|---|---|
| *A61K 31/722* | (2006.01) |
| *A61K 47/60* | (2017.01) |
| *A61K 47/61* | (2017.01) |
| *C08B 37/08* | (2006.01) |

(52) U.S. Cl.
CPC ............ *A61K 31/722* (2013.01); *A61K 47/60* (2017.08); *A61K 47/61* (2017.08); *C08B 37/003* (2013.01)

(58) Field of Classification Search
CPC .............. A61K 47/4823; A61K 31/722; A61K 47/48215; C08B 37/003
USPC .......................................................... 514/55
See application file for complete search history.

(56) References Cited

U.S. PATENT DOCUMENTS

| | | | |
|---|---|---|---|
| 5,486,140 | A | 1/1996 | Abbott et al. |
| 8,431,543 | B2 | 4/2013 | ParK et al. |
| 8,466,127 | B2 | 6/2013 | Hu et al. |

FOREIGN PATENT DOCUMENTS

| | | |
|---|---|---|
| WO | 9602259 A1 | 2/1996 |
| WO | 2010085959 A1 | 8/2010 |

OTHER PUBLICATIONS

The English translation of the Japanese Office Action, dated Dec. 15, 2016, in the related Japanese patent application No. 2014-553708.
The English translation of the Russian Office Action, dated Nov. 23, 2016, in the related Russian patent application No. 2014132564.
The International Search Report and Written Opinion, dated Mar. 27, 2013, in the related PCT Appl. No. PCT/EP2013/051279.

(Continued)

*Primary Examiner* — Shaojia A Jiang
*Assistant Examiner* — Michael C Henry

(57) ABSTRACT

The invention relates to the chitosan polymer derivatives of formula I: and pharmaceutically acceptable salts and esters thereof, wherein Y, $X^1$, $X^4$, $R^1$, $R^2$, and n are defined in the detailed description and claims. The chitosan polymer derivatives of formula I bind to or associate with alpha-4-beta-1 ($\alpha 4\beta 1$) and alpha-V-beta-3 ($\alpha V\beta 3$) integrin dimers and can be used in delivery formulations to deliver drugs, nucleic acids, or other therapeutic compounds to tissues or cells expressing such integrins.

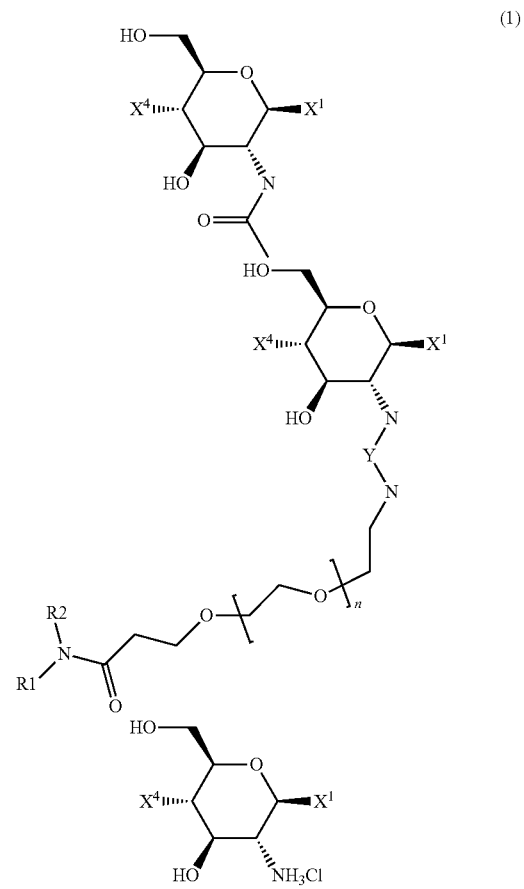

(1)

3 Claims, 3 Drawing Sheets

(56) References Cited

OTHER PUBLICATIONS

Noh et al., "Pegylated poly-L-arginine derivatives of chitosan for effective delivery of siRNA," Journal of Controlled Release, vol. 145, pp. 159-164 (2010).
Casettari et al., "PEGylated chitosan derivatives: Synthesis, characterizations andpharmaceutical applications," Progress in Polymer Science, vol. 37(5), pp. 659-685 (2012).
The U.S. Office Action, dated Mar. 16, 2015, in the related U.S. Appl. No. 13/748,642.
The U.S. Office Actions, dated Feb. 16, 2016 and Nov. 17, 2016, in the related U.S. Appl. No. 14/373,669.

CHITOSAN COVALENTLY LINKED WITH SMALL MOLECULE INTEGRIN ANTAGONIST FOR TARGETED DELIVERY

CROSS-REFERENCE TO RELATED APPLICATIONS

This application is a Continuation of application Ser. No. 14/373,669, filed Jul. 22, 2014, which is a National Stage Application of PCT/EP2013/051279, filed Jan. 24, 2013, which claims the benefit of U.S. Provisional Patent Application No. 61/591,293, filed Jan. 27, 2012 and U.S. Provisional Patent Application No. 61/670,665, filed Jul. 12, 2012. Each of these applications is hereby incorporated by reference herein in its entirety.

The present invention relates to chitosan polymer derivatives that are covalently linked to small molecule integrin antagonists for targeted delivery. Some of these small molecule integrin antagonists bind to the VLA-4 (Very Late Antigen-4) dimer (also referred to as the Integrin alpha-4-beta-1 dimer or α4β1). Other small molecule integrin antagonists of the present invention bind to the alpha-V-beta-3 (αVβ3) dimer. Such chitosan linked integrins can be used as targeting ligands for the delivery of other small molecules, peptides, and nucleic acids. For example, such chitosans may be used for the formation of oligonucleotide or siRNA nanoparticles which aid in the selective delivery of such oligonucleotides or siRNA to cells which express such integrin receptors, thereby altering or preventing the expression of target genes through RNA interference (RNAi) or other mechanisms.

VLA-4 (Very Late Antigen-4, also called α4β1) is an integrin dimer. It is comprised of two subunits consisting of CD49d (alpha) and CD29 (beta). VLA-4 is expressed on leukocyte plasma membranes which bind to VCAM-1 on blood vessels (after activation by cytokines) helping the leukocytes to adhere to vascular endothelium (contributing to atherosclerosis or other inflammatory diseases). Certain cancer cells may also express VLA-4 which bind to VCAM-1 adhering to the endothelium (increasing the risk of metastasis). Thus, compounds that bind to VLA-4 may block the interaction with VCAM-1 potentially treating or preventing diseases mediated by this interaction. Alternatively, compounds that bind to VLA-4 may be used in delivery formulations to deliver drugs, nucleic acids, or other therapeutic compounds to tissues or cells expressing VLA-4 for the treatment or prevention of disease.

The present invention relates to chitosan polymer derivatives that are covalently linked to small molecule integrin antagonists for targeted delivery. Some of these small molecule integrin antagonists bind to the VLA-4 (Very Late Antigen-4) dimer (also referred to as the Integrin alpha-4-beta-1 dimer or α4β1). Other small molecule integrin antagonists of the present invention bind to the alpha-V-beta-3 (αVβ3) dimer. Such chitosan linked integrins can be used as targeting ligands for the delivery of other small molecules, peptides, and nucleic acids. For example, such chitosans may be used for the formation of oligonucleotide or siRNA nanoparticles which aid in the selective delivery of such oligonucleotides or siRNA to cells which express such integrin receptors, thereby altering or preventing the expression of target genes through RNA interference (RNAi) or other mechanisms.

BACKGROUND OF THE INVENTION

VLA-4 (Very Late Antigen-4, also called α4β1) is an integrin dimer. It is comprised of two subunits consisting of CD49d (alpha) and CD29 (beta). VLA-4 is expressed on leukocyte plasma membranes which bind to VCAM-1 on blood vessels (after activation by cytokines) helping the leukocytes to adhere to vascular endothelium (contributing to atherosclerosis or other inflammatory diseases). Certain cancer cells may also express VLA-4 which bind to VCAM-1 adhering to the endothelium (increasing the risk of metastasis). Thus, compounds that bind to VLA-4 may block the interaction with VCAM-1 potentially treating or preventing diseases mediated by this interaction. Alternatively, compounds that bind to VLA-4 may be used in delivery formulations to deliver drugs, nucleic acids, or other therapeutic compounds to tissues or cells expressing VLA-4 for the treatment or prevention of disease.

The integrin type αVβ3 is a receptor for vitronectin [Hermann, P. et al. "The vitronectin receptor and its associated CD47 molecule mediates proinflammatory cytokine synthesis in human monocytes by interaction with soluble CD23" [*The Journal of cell biology* 144 (1999): 767-75]. It consists of two components, integrin alpha V and integrin beta 3 (CD61), and is expressed by platelets as well as other cell types. It has been shown that inhibitors of αVβ3 like etaracizumab may be used as antiangiogenics. Alternatively, compounds that bind to αVβ3 may be used in delivery formulations to deliver drugs, nucleic acids, or other therapeutic compounds to tissues or cells expressing αVβ3 for the treatment or prevention of disease.

RNA interference is a well-known process in which the translation of messenger RNA (mRNA) into protein is interfered with by the association or binding of complementary or partially complementary oligonucleotides such as small interfering RNA (siRNA), short hairpin RNA (shRNA), micro RNA (miRNA), or antisense oligonucleotides. siRNAs are double-stranded RNA molecules, usually ranging from 19-25 nucleotides in length that associate with a set of proteins in the cytoplasm known as RISC (RNA-induced silencing complex). RISC ultimately separates the double stranded siRNA allowing one strand to bind or associate with a complementary or partially complementary portion of an mRNA molecule after which the mRNA is destroyed by RISC or otherwise prevented from being translated-consequently suppressing the expression of the encoded protein or gene product.

One of the problems in using nucleic acids such as siRNA in therapeutic applications (especially for systemic administration in humans) has been in delivering the nucleic acids to: (1) particular target tissues or cell types and (2) to the cytoplasm of those cells (i.e., where the mRNA is present and translated into protein). Part of the delivery problem is based on the fact that nucleic acids are negatively charged and easily degraded (especially if unmodified), efficiently filtered by the kidney, and cannot be easily transported to the cytoplasm of the cells by themselves. Thus, a significant amount of research has focused on solving the delivery problem with various carriers and formulations including liposomes, micelles, peptides, polymers, conjugates and aptamers. See Ling et al, *Advances in Systemic siRNA Delivery*, Drugs Future 34(9): 721 (September 2009). Some of the more promising delivery vehicles have involved the use of lipidic systems including lipid nanoparticles. See Wu et al., *Lipidic Systems for In Vivo siRNA Delivery*, AAPS J. 11(4): 639-652 (December 2009); International Patent Application Publication No. WO 2010/042877 by Hope et al ("*Improved Amino Lipids And Methods For the Delivery of Nucleic Acids*"). However, clinical trials using lipid-based nanoparticles (LNPs) have been somewhat limited by safety concerns, antibody opsonization and phagocytosis, and an inability to deliver nucleic acids, such as siRNA, to organs other than the liver and lung after intravenous administration.

Chitosan spontaneously forms complexes with DNA and siRNA due to the association of the mildly positively charged oligomer with the anionic DNA and/or siRNA. Chitosan has been shown to mediate in vitro transfection and knock down of siRNA targeted mRNA in 10% serum. The mechanism of release of siRNA from endosomal compartments is unknown, but it is thought to occur with the acidification of the endosomal compartment upon its maturation. It has also been reported that chitosan has mucoadhesive properties. Chitosan is biodegradable and it has been reported to have an Oral LD50 of 16 g/kg in rats. It has been approved for human therapy for wound healing and it is currently in clinical trials for enhanced delivery of peptides via the lung. There are reports for the use of chitosan for delivery of oligonucleotides (see International Patent Application Publication Nos. WO2008/031899, WO2010085959, WO2009012786, and WO2009006905). In these cases, the chitosan does not contain targeted ligands.

The use of targeting ligands with biodegradable polymers has been reported to a lesser extent. The use of folic acid, covalently attached to chitosan for delivery of siRNA has been reported (Jiang, H.-L. et al., "The suppression of lung tumorigenesis by aerosol-delivered folate-chitosan-graft-polyethylenimine/Akt1 shRNA complexes through the Akt signaling pathway" *Biomaterials* (2009), 30, 5844-5852). See also Rudzinski, W. E. and Aminabhavi, "Chitosan as a carrier for targeted delivery of small interfering RNA" in *International Journal of Pharmaceutics* 399 (2010): 1-11. Although the use of an integrin targeting peptide for targeted delivery of chitosan-siRNA nanoparticles has also been reported (Han, H. D. et al., "Targeted gene silencing using RGD-labeled chitosan nanoparticles" *Clinical Cancer Research* (2010), 16, 3910-3922), a need remains for further improved carriers and formulations including small molecule chitosan derivative conjugates for the targeted delivery of therapeutics.

SUMMARY OF THE INVENTION

The invention relates to chitosan polymer derivatives comprising three monomers of formula I:

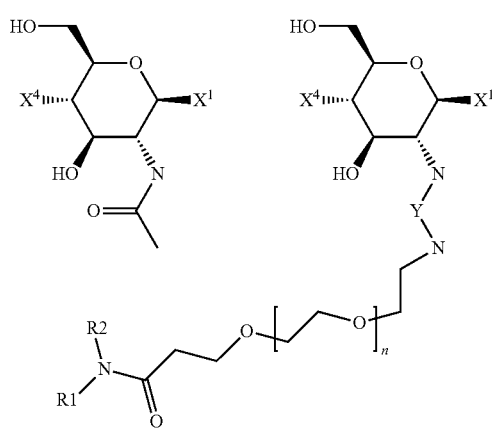

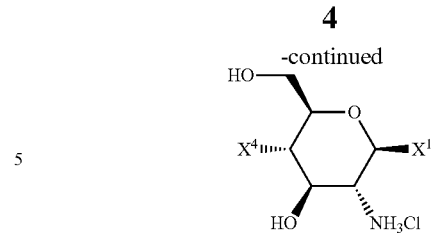

wherein the monomers are covalently linked to each by a single oxygen atom at positions $X^1$ and $X^4$ which represent beta-1-4 linkages, except at the terminal ends of the polymer wherein $X^1$ and $X^4$ represent hydroxy of any stereochemistry; and wherein Y, R1, R2, and n are defined in the detailed description and claims. In addition, the present invention relates to conjugates and compositions linked to such polymers for the improved delivery of small molecules, peptides, and nucleic acids to target cells expressing the integrin α4β1 (Very Late Antigen-4) dimer or the αVβ3 dimer for various therapeutic and other applications. The present invention also relates to methods of manufacturing and using such polymers, conjugates, and compositions.

DETAILED DESCRIPTION OF THE INVENTION

Figure 1:
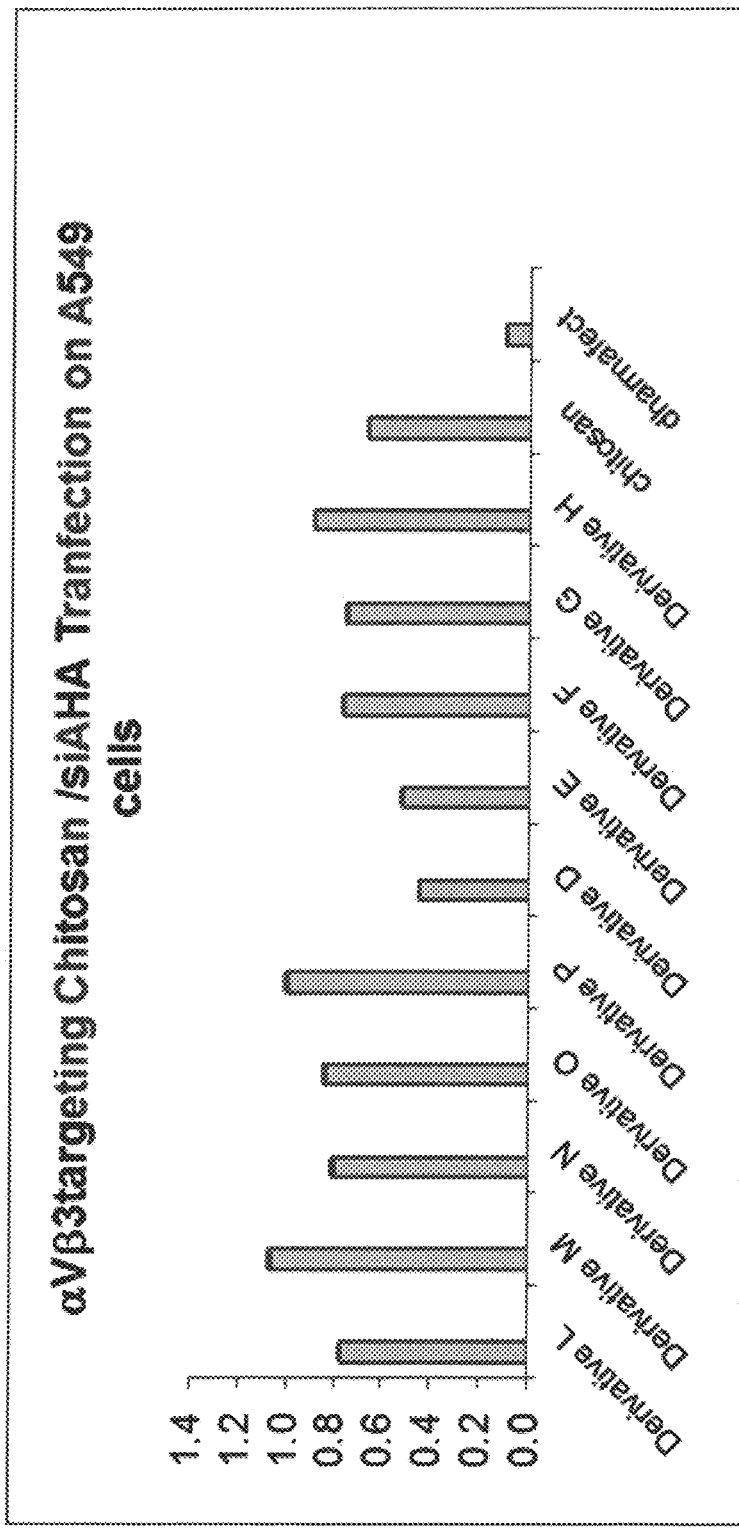
FIG. 1 shows a bar graph of Aha1 mRNA knockdown in A549 cells (relative to GAPDAH RNA as a control) with chitosan-siRNA nanoparticles in which the chitosans were covalently derivatized with a αVβ3 small molecule antagonist. The chitosans vary by the degree to which the small molecule has been loaded to available reactive amino termini of the chitosan oligomer prior to complexation with siRNA.

Unless otherwise indicated, the following specific terms and phrases used in the description and claims are defined as follows:

The term "moiety" refers to an atom or group of chemically bonded atoms that is attached to another atom or molecule by one or more chemical bonds thereby forming part of a molecule. For example, the variables Y, R1, and R2 of formula I refer to moieties that are attached to the structure shown in formula I by a covalent bond where indicated.

Unless otherwise indicated, the term "hydrogen" or "hydro" refers to the moiety of a hydrogen atom (—H) and not $H_2$.

The term "alkyl" refers to an aliphatic straight-chain or branched-chain saturated hydrocarbon moiety having 1 to 25 carbon atoms.

The term "TFA" refers to trifluoroacetic acid.

Unless otherwise indicated, the term "a compound of the formula" or "a compound of formula" or "compounds of the formula" or "compounds of formula" means any compound selected from the genus of compounds as defined by the formula (including any pharmaceutically acceptable salt or ester of any such compound if not otherwise noted).

Chitosan is a natural biopolymer, occurring as a linear polysaccharide comprised of β-(1-4)-linked D-glucosamine (deacetylated unit) and N-acetyl-D-glucosamine (acetylated unit); the acetylated and free amino-glucosamine moieties are randomly ordered. Chitosan has many biomedical applications. Chitosan is also produced by the deacetylation of chitin. Different forms of chitosan are characterized by the degree of de-acetylation (% DA) as well as the average molecular weight (e.g., MW>150 KDa) of a diverse collection of oligomers within a preparation of chitosan. Polydispersity relates the diversity of different molecular weight chitosan within a preparation. The amino termini of chitosan are believed to have a pKa ~6.5. The oliogermer is stereochemically defined.

Chitosan polymers comprise randomly ordered β-(1-4)-linked D-glucosamine and N-acetyl β-(1-4)-linked D-glucosamine moieties. In the case of β-(1-4)-linked D-glucosamine, the amino group may be protonated depending on pH. In the case of derivatization of an amine group of one or more of these chitosan monomers with a targeting ligand, the polymer is then comprised of a random arrangement of these derivatized monomers. In order to denote the random arrangement of the monomers of the chitosan polymer derivative of the present invention, the genus structure contains the letters $X^1$ and $X^4$ which indicate that the monomers are covalently linked to each other by a single oxygen atom between those positions in beta-1-4 linkages, except at the terminal ends of the polymer wherein $X^1$ and $X^4$ represent a hydroxy group of any stereochemistry. Thus, in denoting the point of attachment between the monomers in formula I, the orientation of the saccharides must be β-(1-4)-linked.

The term "pharmaceutically acceptable salts" refers to those salts which retain the biological effectiveness and properties of the free bases or free acids, which are not biologically or otherwise undesirable. Salts may be formed with inorganic acids such as hydrochloric acid, hydrobromic acid, sulfuric acid, nitric acid, phosphoric acid and the like, preferably hydrochloric acid, and organic acids such as acetic acid, propionic acid, glycolic acid, pyruvic acid, oxalic acid, maleic acid, malonic acid, salicylic acid, succinic acid, fumaric acid, tartaric acid, citric acid, benzoic acid, cinnamic acid, mandelic acid, methanesulfonic acid, ethanesulfonic acid, p-toluenesulfonic acid, N-acetylcystein and the like. In addition, salts may be prepared by the addition of an inorganic base or an organic base to the free acid. Salts derived from an inorganic base include, but are not limited to, the sodium, potassium, lithium, ammonium, calcium, and magnesium salts and the like. Salts derived from organic bases include, but are not limited to salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, lysine, arginine, N-ethylpiperidine, piperidine, polyamine resins and the like. Depending on the substitution patterns, the compounds of the present invention may also exist as zwitterions.

The compounds of the present invention can be present in the form of pharmaceutically acceptable salts. The compounds of the present invention can also be present in the form of pharmaceutically acceptable esters (i.e., the methyl and ethyl esters of the acids of formula I to be used as prodrugs). The compounds of the present invention can also be solvated, i.e. hydrated. The solvation can be affected in the course of the manufacturing process or can take place, i.e. as a consequence of hygroscopic properties of an initially anhydrous compound of formula I (hydration).

Compounds that have the same molecular formula but differ in the nature or sequence of bonding of their atoms or the arrangement of their atoms in space are termed "isomers." Isomers that differ in the arrangement of their atoms in space are termed "stereoisomers." Diastereomers are stereoisomers with opposite configuration at one or more chiral centers which are not enantiomers. Stereoisomers bearing one or more asymmetric centers that are non-superimposable mirror images of each other are termed "enantiomers." When a compound has an asymmetric center, for example, if a carbon atom is bonded to four different groups, a pair of enantiomers is possible. An enantiomer can be characterized by the absolute configuration of its asymmetric center or centers and is described by the R- and S-sequencing rules of Cahn, Ingold and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture".

The term "a therapeutically effective amount" of a formulation of siRNA means an amount of an siRNA compound that is effective to prevent, alleviate or ameliorate symptoms of disease or prolong the survival of the subject being treated. Determination of a therapeutically effective amount is within the skill in the art. The therapeutically effective amount or dosage of a compound according to this invention can vary within wide limits and may be determined in a manner known in the art. Such dosage will be adjusted to the individual requirements in each particular case including the specific compound(s) being administered, the route of administration, the condition being treated, as well as the patient being treated. The daily dosage can be administered as a single dose or in divided doses, or for parenteral administration, it may be given as continuous infusion.

The term "pharmaceutically acceptable carrier" is intended to include any and all material compatible with pharmaceutical administration including solvents, dispersion media, coatings, antibacterial and antifungal agents, isotonic and absorption delaying agents, and other materials and compounds compatible with pharmaceutical administration. Except insofar as any conventional media or agent is incompatible with the active compound, use thereof in the compositions of the invention is contemplated. Supplementary active compounds can also be incorporated into the compositions.

In detail, the present invention relates to chitosan polymer derivatives comprising three monomers of formula I:

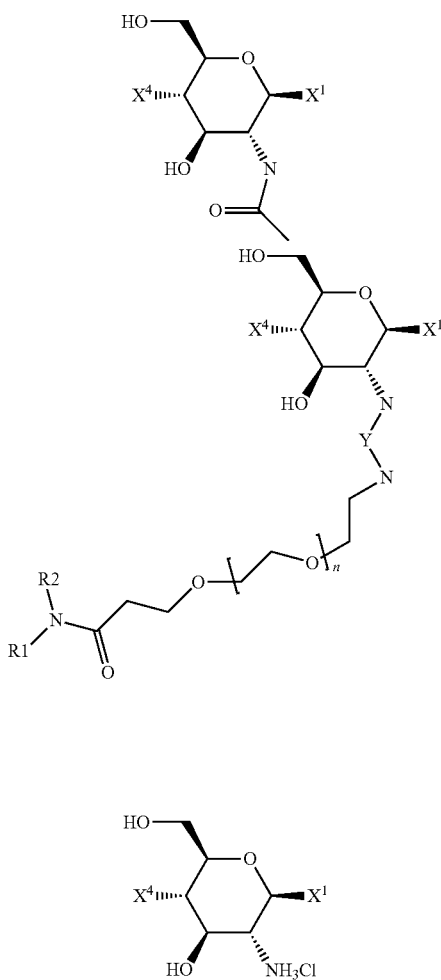

wherein the monomers are covalently linked to each other by a single oxygen atom at positions $X^1$ and $X^4$ which represent beta-1-4 linkages, except at the terminal ends of the polymer wherein $X^1$ and $X^4$ represent hydroxy of any stereochemistry; and wherein:

Y is selected from the group consisting of:
(1) amide-propionyl-thiol-maleimide-propionyl-amide (Pr—S-Mal) of the formula:

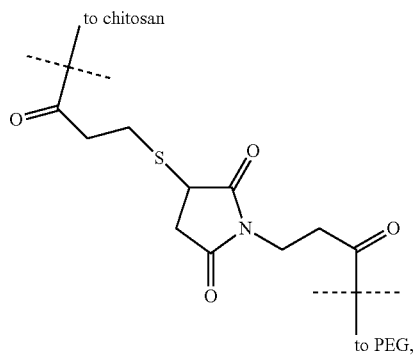

and
(2) succinic acid amide (Suc) of the formula:

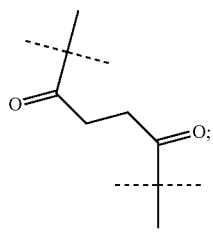

R1 is selected from the group consisting of:
(1) an integrin antagonist for αVβ3 of the formula:

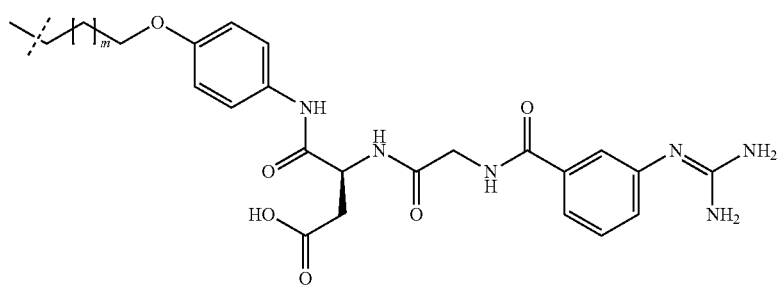

and pharmaceutically acceptable salts and esters thereof, wherein m is 0 or 1; and (2) an integrin antagonist for α4β1 of the formula:

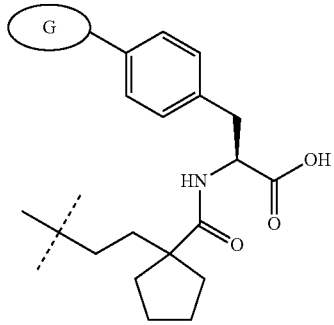

and pharmaceutically acceptable salts and esters thereof, wherein

is:

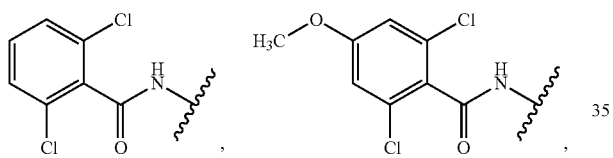

and

R2 is hydrogen or methyl, and n is 8-25.

As used in the above structures, a dashed line "- - -" or the symbol " 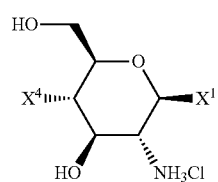 " is used to indicate where the structure or moiety is attached to the base molecule by a covalent bond. In addition, the phrase "to PEG" or "to chitosan" or similar language used in combination with a dashed line or the above symbol, indicates where or how the structure or moiety is attached to the base molecule if there a multiple attachment points.

For example, in particular embodiments, the present invention relates to the chitosan polymer derivatives of formula I wherein Y is amide-propionyl-thiol-maleimide-propionly-amide:

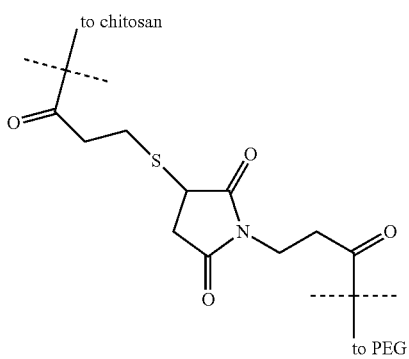

wherein "to chitosan" and "to PEG" indicate the attachment points of the molecule as shown below in formula IA wherein $X^1$, $X^4$, R1, R2, and n are as defined in formula I:

IA

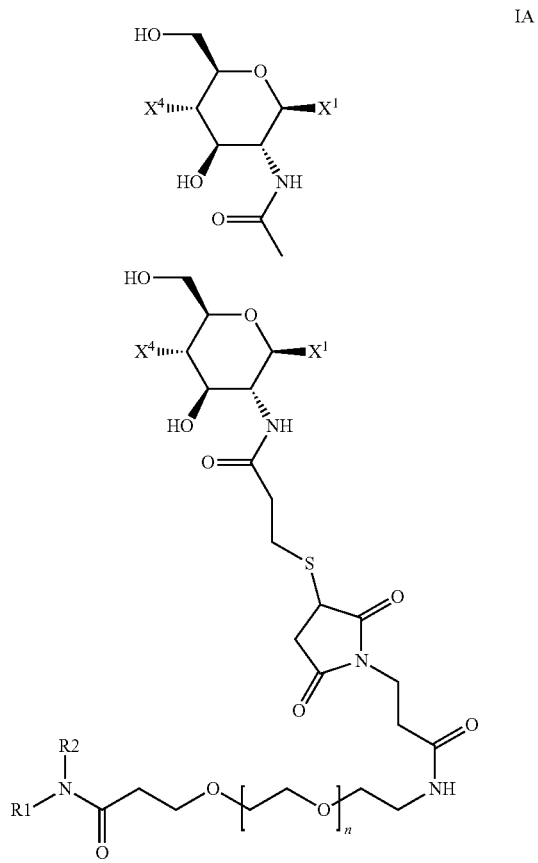

In other particular embodiments, the present invention relates to the chitosan polymer derivatives of formula I wherein Y is succinic acid amide:

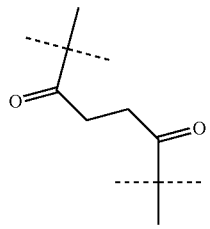

as shown below in formula IB wherein $X^1$, $X^4$, R1, R2, and n are as defined in formula I:

IB

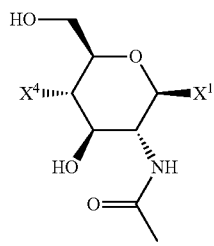

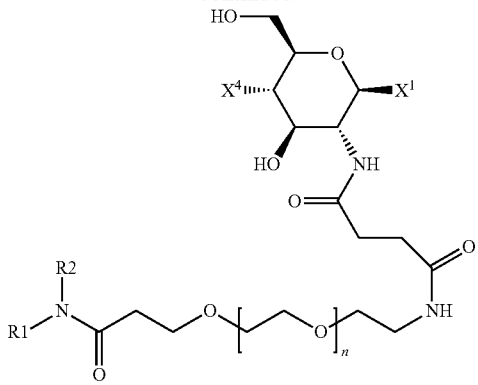

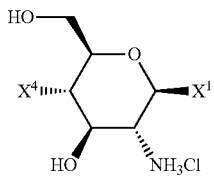

In other particular embodiments, the present invention relates to the chitosan polymer derivatives of formula I wherein R1 is an αVβ3 integrin antagonist of the formula:

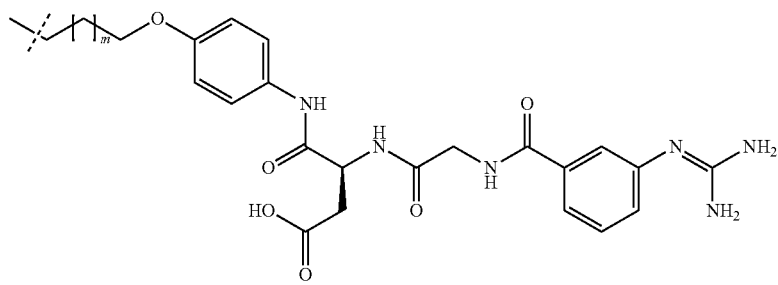

or a pharmaceutically acceptable salt or ester thereof; wherein m is 0 or 1, as shown below in formula IC wherein $X^1$, $X^4$, Y, R2, m and n are as defined in formula I:

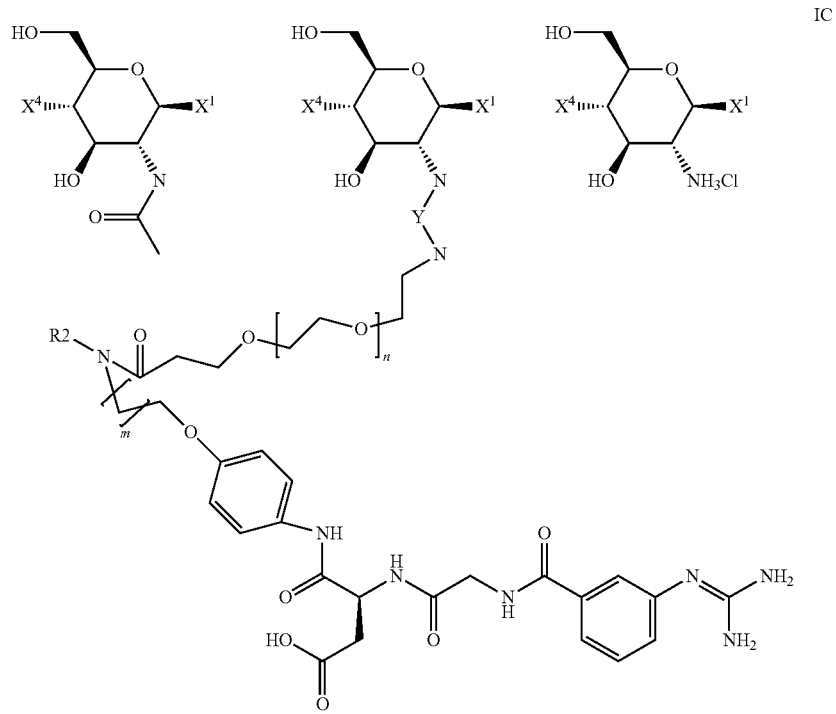

In other particular embodiments, the present invention relates to the chitosan polymer derivatives of formula I wherein R1 is an α4β1 integrin antagonist of the formula:

as shown below in formula ID wherein $X^1$, $X^4$, Y, R2, m and n are as defined in formula I:

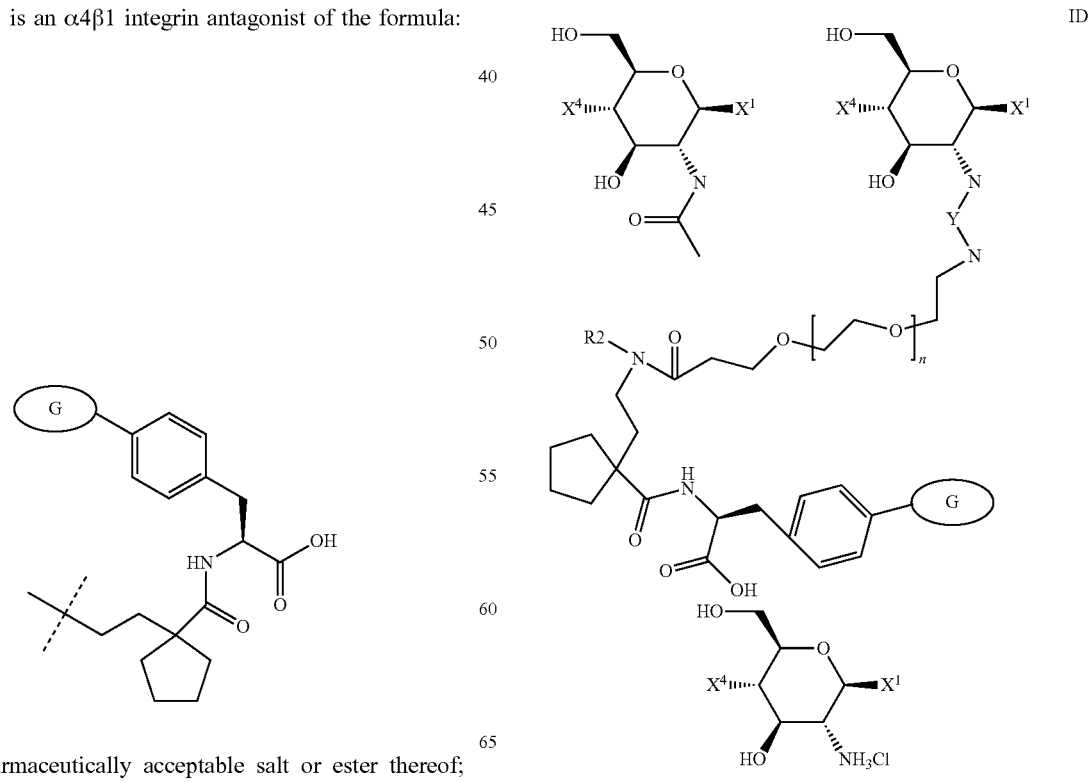

or a pharmaceutically acceptable salt or ester thereof; wherein G is as defined in formula I, The point of covalent linkage of the R1 group is such that the affinity of binding of the integrin antagonist to the integrin receptor is not substantially reduced.

The present invention also relates to conjugates connected to and compositions containing the chitosan polymer derivatives of formula I. In particular embodiments, the chitosan polymer derivatives of the present invention are used for the creation of nanoparticles for the formulation and delivery of siRNA, resulting in the improved delivery to the cytoplasm of target cells expressing α4β1 and/or αVβ3 dimers. The present invention also relates to methods of manufacturing and using such conjugates and compositions. The chitosan polymer derivatives of the present invention are useful as components of conjugates and compositions which improve the delivery of drugs, nucleic acids, or other therapeutic compounds to tissues or cells expressing α4β1 and αVβ3 dimers. In particular embodiments, the present invention relates to nanoparticle formulations containing the chitosan polymer derivatives of the present invention which are useful in delivering siRNA to the cytoplasm of target cells expressing α4β1 and αVβ3 dimers to inhibit the expression of certain proteins through RNA interference. In more particular embodiments, the present invention relates to the chitosan polymer derivatives of formula I for use in formulations that can effectively deliver siRNA to tumor cells and other cell types expressing α4β1 and αVβ3 dimers for the treatment of cancer or inflammatory diseases. Such conjugates, compositions, and formulations are more efficacious and demonstrate improved knockdown capability compared to similar formulations lacking the chitosan polymer derivatives of the present invention.

When using chitosan and its derivatives, the degree of deacetylation is an important aspect for control. Preferably, the chitosan has a relatively high degree of deacetylation. Thus, in one embodiment, the chitosan has a degree of deacetylation of at least 60%.

The molecular weight of the chitosan is preferably more than 10 kDa. In another embodiment, the molecular weight is more than 50 kDa and even more preferred is a molecular weight of more than 100 kDa.

Another important parameter is the so-called N:P ratio, defined herein as the ratio of basic (non-acetylated or acylated) chitosan amino groups (N) to RNA phosphate groups (P). In a preferred embodiment, a nanoparticle containing the chitosan polymer derivatives of the present invention is formed at an N:P ratio larger than 3 to 50. The above mentioned parameters can all be used to control the characteristics of the formed nanoparticle. In other embodiments, the N:P ratio is at least 20. When employing a high N:P ratio and a low RNA concentration, nanoparticles can be formed that comprise loosely bound chitosan.

Those scientists skilled in the art will appreciate how to manipulate parameters such as the concentration of siRNA and derivatized chitosan to create nanoparticles. In one embodiment, the concentration of the RNA solution is at least 30 nM.

In particular embodiments, the present invention relates to the chitosan polymer derivatives of the present invention wherein R1 in formula I is:

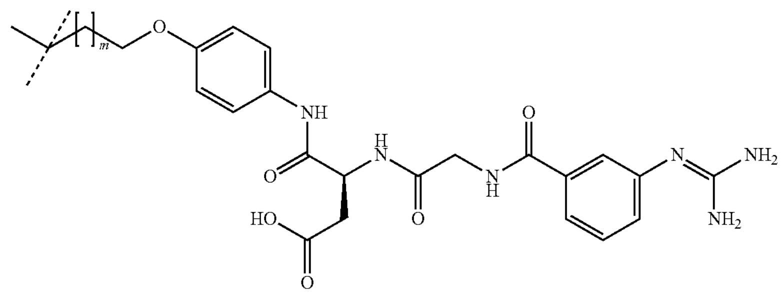

2 or pharmaceutically acceptable salts and esters thereof, wherein m is 0 or 1.

In other embodiments, the present invention relates to the chitosan polymer derivatives of the present invention wherein R1 in formula I is:

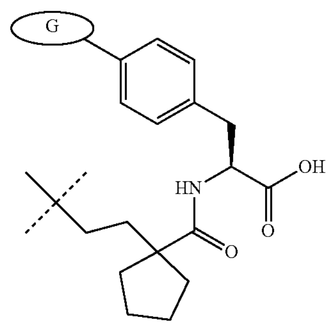

3 or pharmaceutically acceptable salts and esters thereof, wherein:

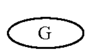

is 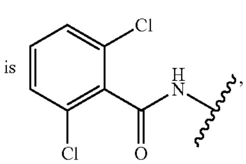 ,

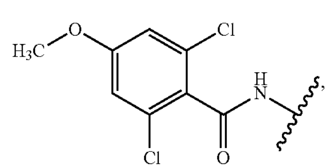

, 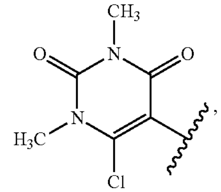 , or

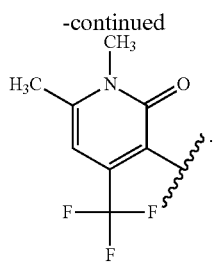

In more particular embodiments, the present invention is directed to the chitosan polymer derivatives of formula I wherein:

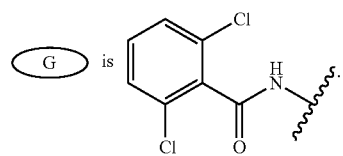 [SMILES: *NC(=O)c1c(Cl)cccc1Cl]

In other embodiments, the present invention is directed to the chitosan polymer derivatives of formula I wherein:

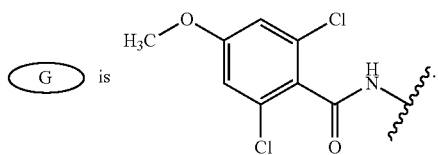 [SMILES: *NC(=O)c1c(Cl)cc(OC)cc1Cl]

In other embodiments, the present invention is directed to the chitosan polymer derivatives of formula I wherein:

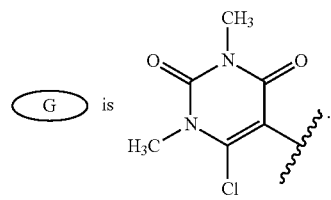 [SMILES: *c1c(Cl)n(C)c(=O)n(C)c1=O]

In other embodiments, the present invention is directed to the chitosan polymer derivatives of formula I wherein:

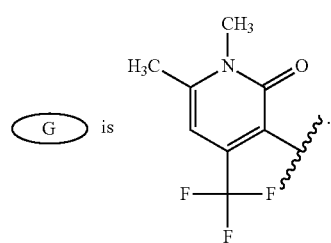 [SMILES: *c1c(C(F)(F)F)cc(C)n(C)c1=O]

In other embodiments, the present invention is directed to the chitosan polymer derivatives of formula I wherein m is 0.

In more specific embodiments, the present invention is directed to a chitosan polymer derivative of formula I selected from the group consisting of:

Cs(AK)-αvβ3 Ligand 2 (Chitosan Derivative A), 2.5% N-acetyl-chitosan loaded with 0.15% of (S)—N-[4-[3-[3-[2-[2-[2-[2-[2-[2-[2-[2-[2-[2-[2-[3-(2,5-dioxo-2,5-dihydro-pyrrol-1-yl)-propionylamino]ethoxy]ethoxy]ethoxy]ethoxy]ethoxy]ethoxy]ethoxy]ethoxy]ethoxy]ethoxy]ethoxy]-1-oxopropyl]amino]propoxy]-phenyl]-3-[2-[3-[guanidino]-benzoylamino]-acetylamino]-succinamic acid;

Cs(AK)-αvβ3 Ligand 2 (Chitosan Derivative B), 2.5% N-acetyl-chitosan loaded with 0.21% of (S)—N-[4-[3-[3-[2-[2-[2-[2-[2-[2-[2-[2-[2-[2-[2-[3-(2,5-dioxo-2,5-dihydro-pyrrol-1-yl)-propionylamino]ethoxy]ethoxy]ethoxy]ethoxy]ethoxy]ethoxy]ethoxy]ethoxy]ethoxy]ethoxy]ethoxy]-1-oxopropyl]amino]propoxy]-phenyl]-3-[2-[3-[guanidino]-benzoylamino]-acetylamino]-succinamic acid;

Cs(AK)-αvβ3 Ligand 2 (Chitosan Derivative C), 2.5% N-acetyl-chitosan loaded with 0.76% of (S)—N-[4-[3-[3-[2-[2-[2-[2-[2-[2-[2-[2-[2-[2-[2-[3-(2,5-dioxo-2,5-dihydro-pyrrol-1-yl)-propionylamino]ethoxy]ethoxy]ethoxy]ethoxy]ethoxy]ethoxy]ethoxy]ethoxy]ethoxy]ethoxy]ethoxy]-1-oxopropyl]amino]propoxy]-phenyl]-3-[2-[3-[guanidino]-benzoylamino]-acetylamino]-succinamic acid;

Cs(NM)-αvβ3 Ligand 3 (Chitosan Derivative D), 14% N-acetyl-chitosan loaded with 0.3% of (S)—N-[4-[3-[3-[2-[2-[2-[2-[2-[2-[2-[2-[2-[2-[2-[3-(2,5-dioxo-2,5-dihydro-pyrrol-1-yl)-propionylamino]ethoxy]ethoxy]ethoxy]ethoxy]ethoxy]ethoxy]ethoxy]ethoxy]ethoxy]ethoxy]ethoxy]-1-oxopropyl]amino]ethoxy]-phenyl]-3-[2-[3-[guanidino]-benzoylamino]-acetylamino]-succinamic acid;

Cs(NM)-αvβ3 Ligand 3 (Chitosan Derivative E), 14% N-acetyl-chitosan loaded with 0.6% of (S)—N-[4-[3-[2-[2-[2-[2-[2-[2-[2-[2-[2-[2-[2-[3-(2,5-dioxo-2,5-dihydro-pyrrol-1-yl)-propionylamino]ethoxy]ethoxy]ethoxy]ethoxy]ethoxy]ethoxy]ethoxy]ethoxy]ethoxy]ethoxy]ethoxy]-1-oxopropyl]amino]ethoxy]-phenyl]-3-[2-[3-[guanidino]-benzoylamino]-acetylamino]-succinamic acid;

Cs(NM)-αvβ3 Ligand 3 (Chitosan Derivative F), 14% N-acetyl-chitosant loaded with 1.9% of (S)—N-[4-[3-[3-[2-[2-[2-[2-[2-[2-[2-[2-[2-[2-[2-[3-(2,5-dioxo-2,5-dihydro-pyrrol-1-yl)-propionylamino]ethoxy]ethoxy]ethoxy]ethoxy]ethoxy]ethoxy]ethoxy]ethoxy]ethoxy]ethoxy]ethoxy]-1-oxopropyl]amino]ethoxy]-phenyl]-3-[2-[3-[guanidino]-benzoylamino]-acetylamino]-succinamic acid;

Cs(NM)-αvβ3 Ligand 3 (Chitosan Derivative G), 14% N-acetyl-claitosan loaded with 6% of (S)—N-[4-[3-[3-[2-[2-[2-[2-[2-[2-[2-[2-[2-[2-[3-(2,5-dioxo-2,5-dihydro- pyrrol-1-yl)-propionylamino]ethoxy]ethoxy]ethoxy]ethoxy]ethoxy]ethoxy]ethoxy]ethoxy]ethoxy]ethoxy]ethoxy]-1-oxopropyl]amino]ethoxy]-phenyl]-3-[2-[3-[guanidino]-benzoylamino]-acetylamino]-succinamic acid;

Cs(NM)-αvβ3 Ligand 3 (Chitosan Derivative H), 14% N-acetyl-chitosan loaded with 5.0% of (S)—N-[4-[3-[3-[2-[2-[2-[2-[2-[2-[2-[2-[2-[2-[2-[3-(2,5-dioxo-2,5-dihydro-pyrrol-1-yl)-propionylamino]ethoxy]ethoxy]ethoxy]ethoxy]ethoxy]ethoxy]ethoxy]ethoxy]ethoxy]ethoxy]ethoxy]-1-oxopropyl]amino]ethoxy]-phenyl]-3-[2-[3-[guanidino]-benzoylamino]-acetylamino]-succinamic acid;

Cs(NM)-VLA$_4$ Ligand 1 (Chitosan Derivative I), 14% N-acetyl-chitosan derivatized with 20% of (S)-3-[4-(2,6-dichlorobenzoylamino)phenyl]-2-[[[1-[2-[3-[2-[2-

[2-[2-[2-[2-[2-[2-[3-(2,5-dioxo-2,5-dihydropyrrol-1-yl)propionylamino]-ethoxy]ethoxy]ethoxy]ethoxy]ethoxy]ethoxy]ethoxy]propionylamino]ethyl]cyclopentyl]carbonyl]amino]propionic acid;

Cs(NM)-VLA$_4$ Ligand 3 (Chitosan Derivative J), 14% N-acetyl-chitosan derivatized with 18% of (S)-2-[4-[(3-[2-[2-[2-[2-[2-[2-[2-[3-(2,5-Dioxo-2,5-dihydropyrrol-1-yl)propionylamino]ethoxy]ethoxy]ethoxy]ethoxy]ethoxy]ethoxy]ethoxy]propionylamino)methyl]-2,6-difluorobenzoylamino]-3-[4-(1,3,6-trimethyl-2,4-dioxo-1,2,3,4-tetrahydropyrimidin-5-yl)phenyl]propionic acid; and Cs(NM)-VLA$_4$ Ligand 2 Acid (4% Loading) (Chitosan Derivative K), 14% N-acetyl-chitosan derivatized with 4% of N-[2-[2-[2-[2-[2-[2-[2-[2-[2-[2-[2-[2-[2-[2-[2-[2-[2- [2-[2-[2-[2-[2-[2-[2-[1-(S)-1-carboxy-2-[4-(2,6-dichlorobenzoylamino)phenyl]ethylcarbamoyl]cyclopentyl]ethylcarbamoyl]ethoxy]ethoxy]ethoxy]ethoxy]ethoxy]ethoxy]ethoxy]ethoxy]ethoxy]ethoxy]ethoxy]ethoxy]ethoxy]ethoxy]ethoxy]ethoxy]ethoxy]ethoxy]ethoxy]ethoxy]ethoxy]ethyl]succinamic acid.

In other particular embodiments, the present invention is directed to chitosans which are covalently linked with small molecule integrin antagonist-siRNA nanoparticle compositions comprising:

(1) derivatized and underivatized chitosan, and
(2) a polynucleotide (such as siRNA).

In addition, the present invention relates to methods of manufacturing and using the chitosan polymer derivatives of formula I as well as pharmaceutical compositions containing such polymers. The chitosan polymer derivatives of formula I are useful in formulating compositions such as nanoparticles to improve the delivery of small molecules, peptides, and nucleic acids such as siRNA to the cytoplasm of target cells expressing VLA-4 or the αVβ3 dimers. In particular embodiments, the present invention relates to chitosan-containing nanoparticle compositions and formulations containing the chitosan polymer derivatives of formula I which are useful in delivering siRNA to the cytoplasm of target cells expressing VLA-4 or the αVβ3 dimers to inhibit the expression of certain target proteins through RNA interference.

In more particular embodiments, the invention relates to the use of the chitosan polymer derivatives of formula I for formulation into derivatized chitosan nanoparticle compositions to facilitate the delivery of nucleic acids such as siRNA to tumor cells and other cell types expressing VLA-4 or the αVβ3 dimers. Furthermore, the use of chitosan polymer derivatives of formula I to synthesize delivery formulations to treat inflammation and proliferative disorders, like cancers, is part of the invention.

In one embodiment there is provided a chitosan polymer derivative of formula I:

I

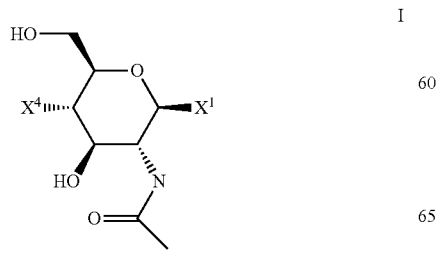

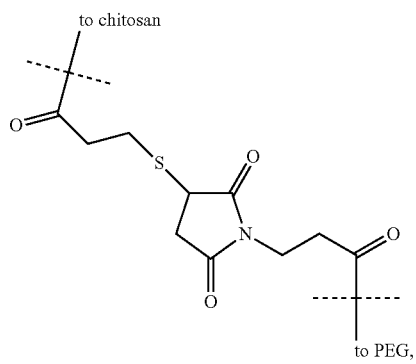

wherein the monomers of formula I are covalently linked to each other by a single oxygen atom at positions $X^1$ and $X^4$ which represent beta-1-4 linkages, except at the terminal ends of the polymer wherein $X^1$ and $X^4$ represent hydroxy of any stereochemistry; and wherein:

Y is selected from the group consisting of:

(1) a moiety of the formula:

and (2) a moiety of the formula:

R1 is selected from the group consisting of:
(1) a moiety of the formula:

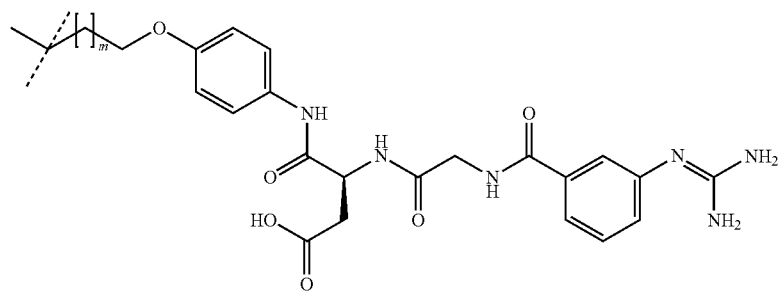

wherein m is 0 or 1; and
(2) a moiety of the formula:

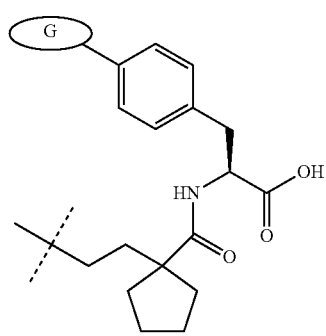

wherein

G is:

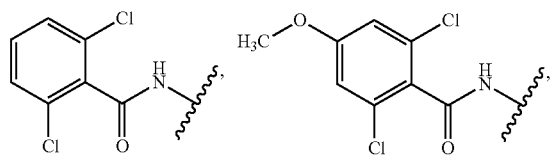

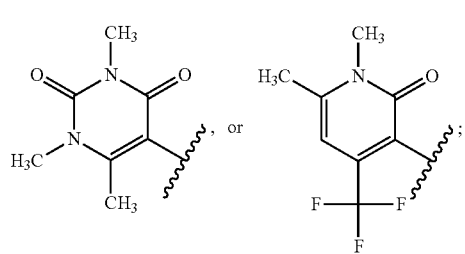, or 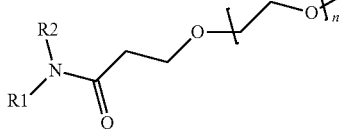;

R2 is hydrogen or methyl, and n is 8-25.

In one embodiment there is provided a chitosan polymer derivative of formula I:

I

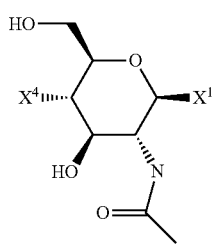

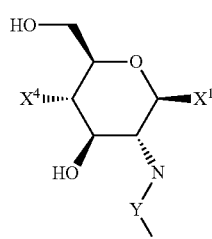

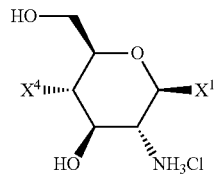

wherein the monomers of formula I are covalently linked to each other by a single oxygen atom at positions $X^1$ and $X^4$ which represent beta-1-4 linkages, except at the terminal ends of the polymer wherein $X^1$ and $X^4$ represent hydroxy of any stereochemistry; and wherein:

Y is a moiety of the formula:
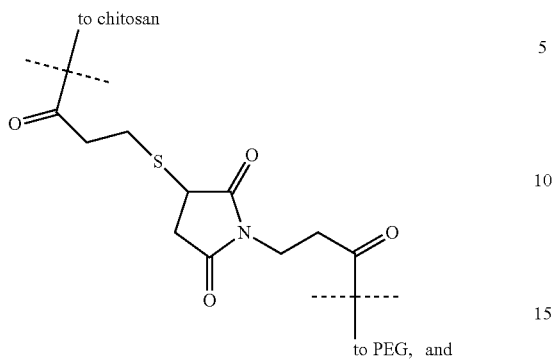
R1 is selected from the group consisting of:
(1) a moiety of the formula:
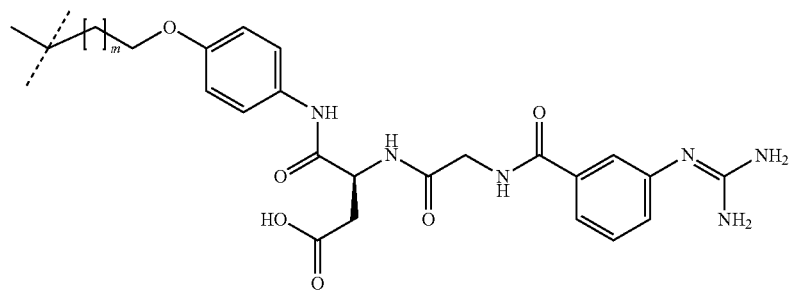
wherein m is 0 or 1; and
(2) a moiety of the formula:
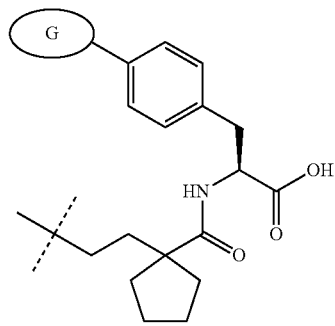
wherein
is:
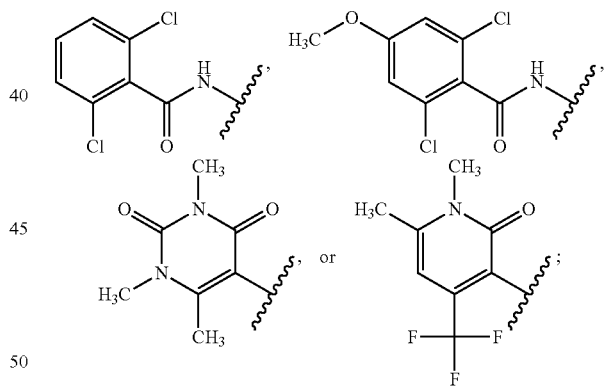
R2 is hydrogen or methyl, and n is 8-25.
In one embodiment there is provided a chitosan polymer derivative of formula I:
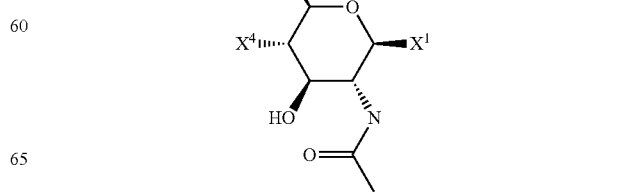

-continued

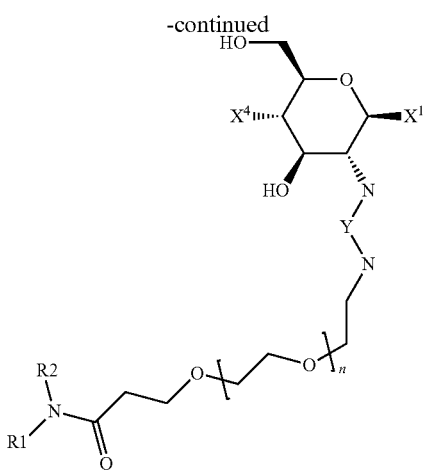

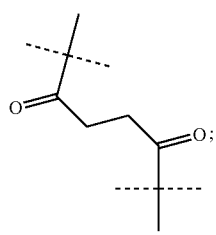

wherein the monomers of formula I are covalently linked to each other by a single oxygen atom at positions $X^1$ and $X^4$ which represent beta-1-4 linkages, except at the terminal ends of the polymer wherein $X^1$ and $X^4$ represent hydroxy of any stereochemistry; and wherein:

Y is a moiety of the formula:

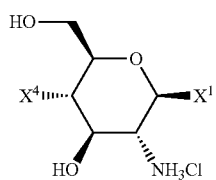

R1 is selected from the group consisting of:
(1) a moiety of the formula:

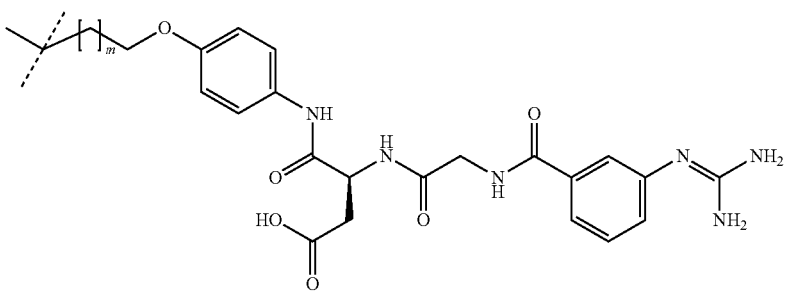

wherein m is 0 or 1; and
(2) a moiety of the formula:

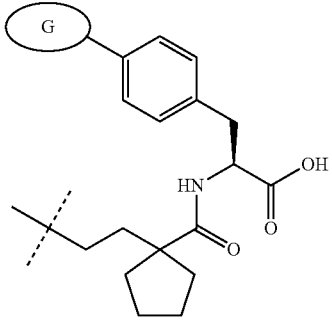

wherein

G is:

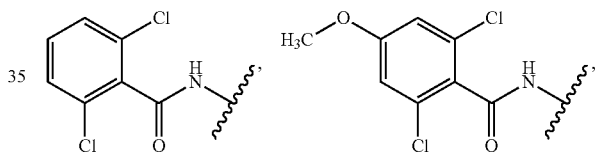

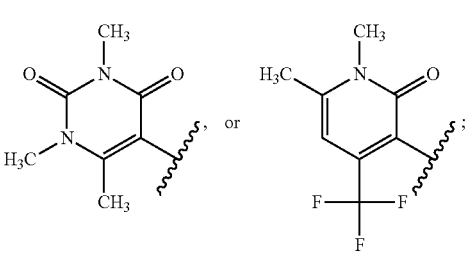

R2 is hydrogen or methyl, and n is 8-25.

In one embodiment there is provided a chitosan polymer derivative of formula I:

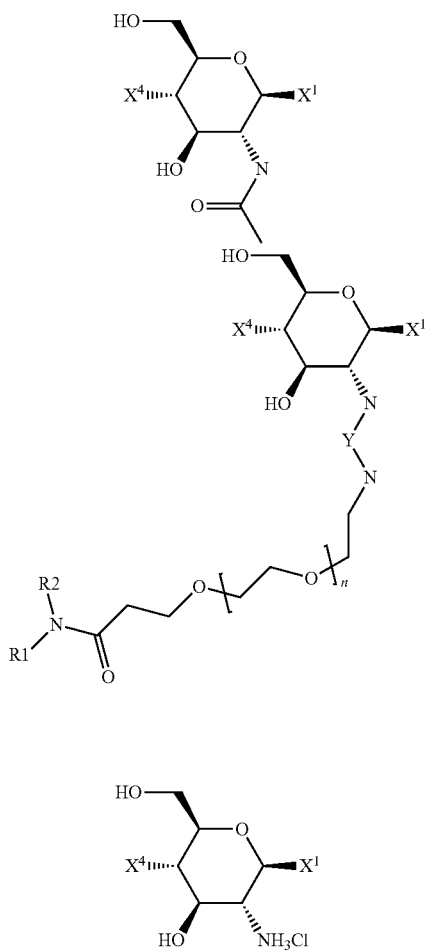

wherein the monomers of formula I are covalently linked to each other by a single oxygen atom at positions $X^1$ and $X^4$ which represent beta-1-4 linkages, except at the terminal ends of the polymer wherein $X^1$ and $X^4$ represent hydroxy of any stereochemistry; and wherein:

Y is selected from the group consisting of:

(1) a moiety of the formula:

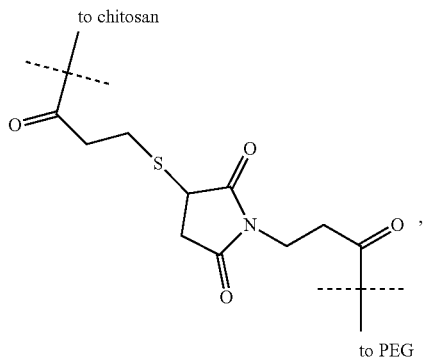

and (2) a moiety of the formula:

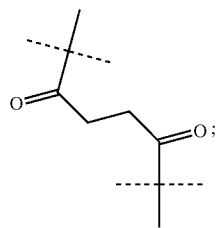

R1 is

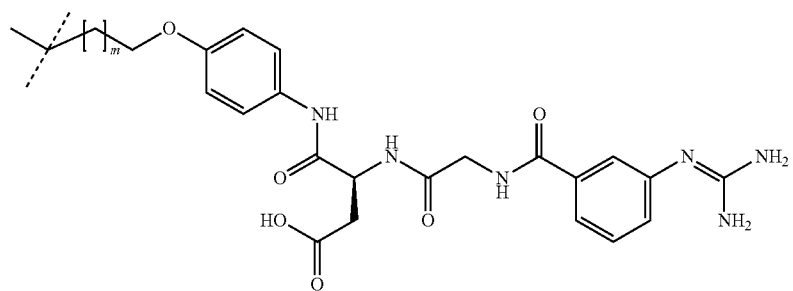

and

R2 is hydrogen or methyl, and n is 8-25.

In one embodiment there is provided a chitosan polymer derivative of formula I:

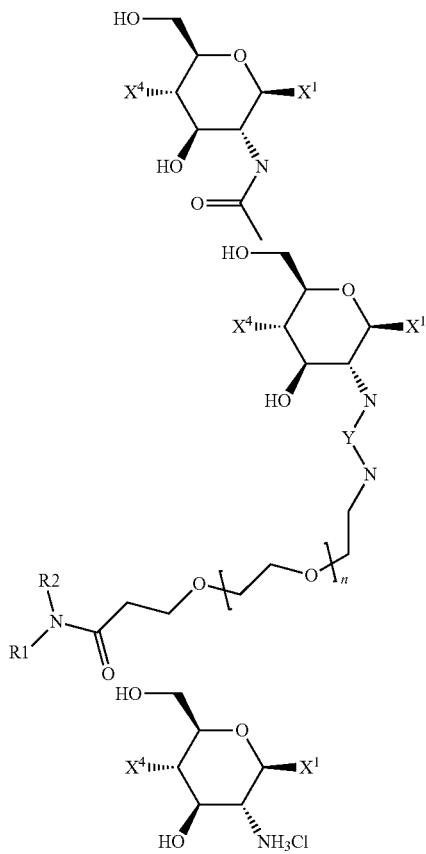

I wherein the monomers of formula I are covalently linked to each other by a single oxygen atom at positions $X^1$ and $X^4$ which represent beta-1-4 linkages, except at the terminal ends of the polymer wherein $X^1$ and $X^4$ represent hydroxy of any stereochemistry; and wherein:

Y is selected from the group consisting of:

(1) a moiety of the formula:

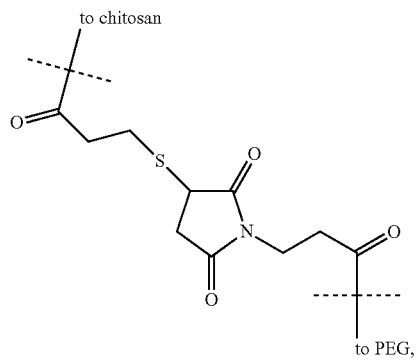

and (2) a moiety of the formula:

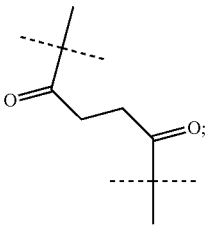

R1 is a moiety of the formula:

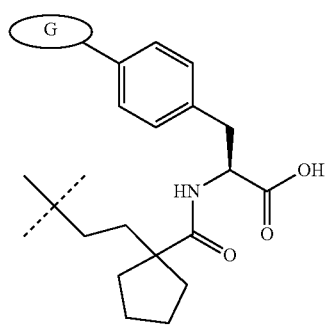

wherein

G is:

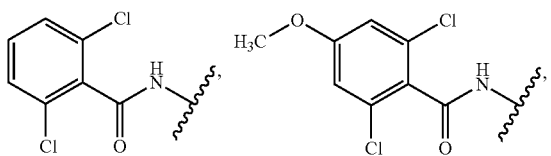

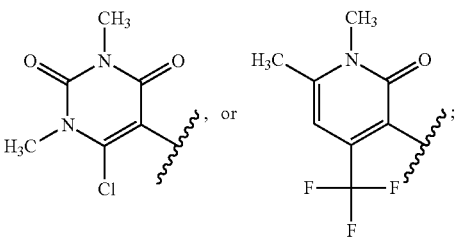

R2 is hydrogen or methyl, and n is 8-25.

In one embodiment there is provided a chitosan polymer derivative of formula I:

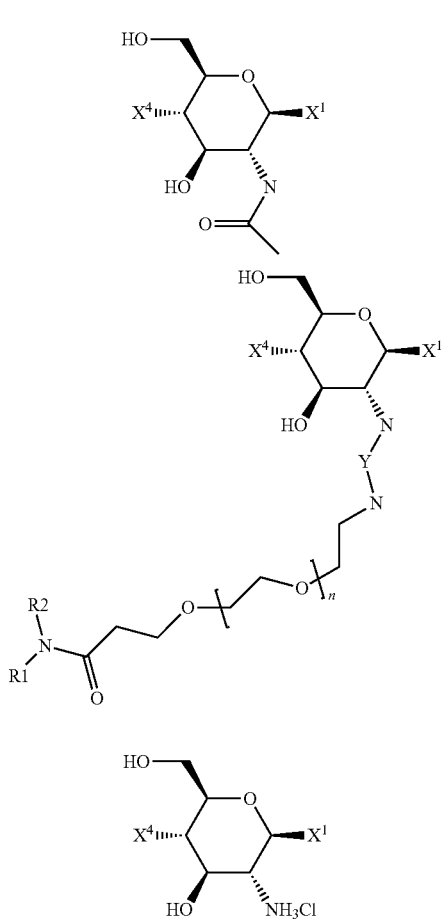

wherein the monomers of formula I are covalently linked to each other by a single oxygen atom at positions $X^1$ and $X^4$ which represent beta-1-4 linkages, except at the terminal ends of the polymer wherein $X^1$ and $X^4$ represent hydroxy of any stereochemistry; and wherein:

Y is selected from the group consisting of:

(1) a moiety of the formula:

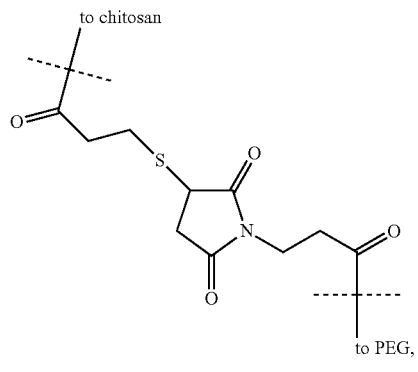

and (2) a moiety of the formula:

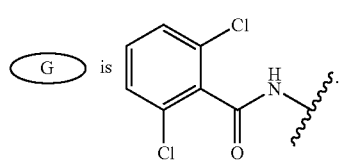 [SMILES: *NC(=O)c1c(Cl)cccc1Cl]

R1 is a moiety of the formula:

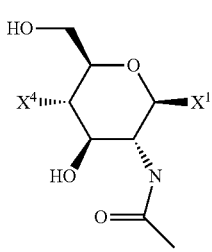

wherein

G is

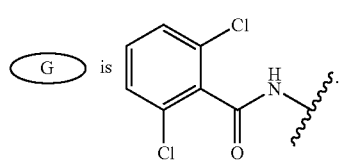 [SMILES: *NC(=O)c1c(Cl)cccc1Cl]

In one embodiment there is provided a chitosan polymer derivative of formula I:

33

-continued

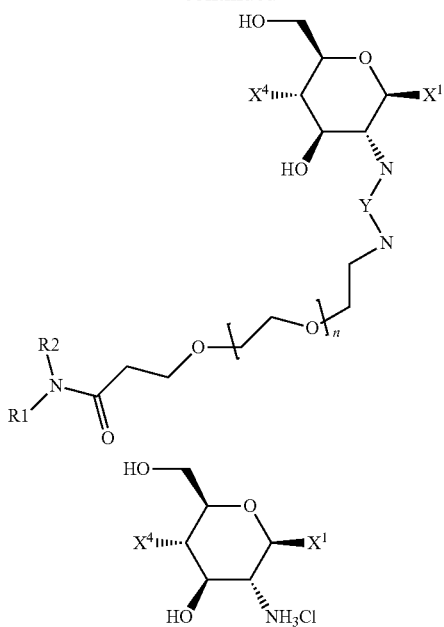

wherein the monomers of formula I are covalently linked to each other by a single oxygen atom at positions $X^1$ and $X^4$ which represent beta-1-4 linkages, except at the terminal ends of the polymer wherein $X^1$ and $X^4$ represent hydroxy of any stereochemistry; and wherein:

Y is selected from the group consisting of:

(1) a moiety of the formula:

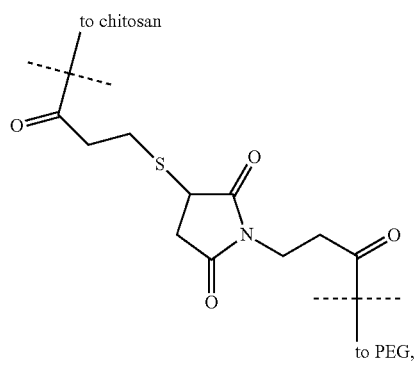

and (2) a moiety of the formula:

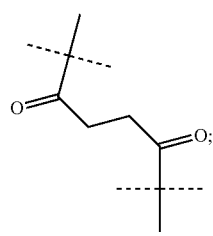

34

R1 is a moiety of the formula:

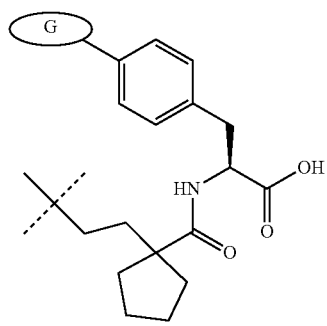

wherein

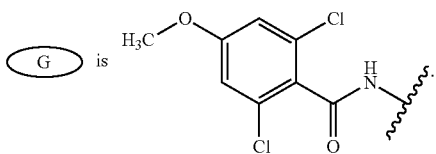 [SMILES: *NC(=O)c1c(Cl)cc(OC)cc1Cl]

In one embodiment there is provided a chitosan polymer derivative of formula I:

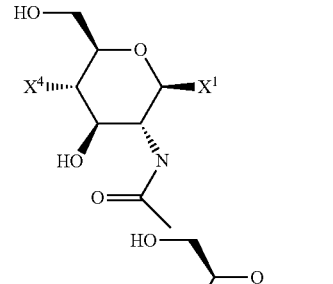

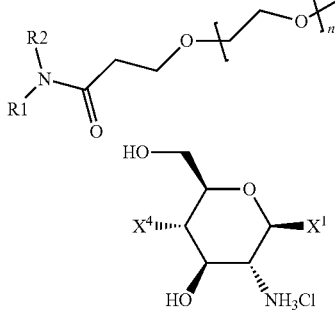

wherein the monomers of formula I are covalently linked to each other by a single oxygen atom at positions $X^1$ and $X^4$ which represent beta-1-4 linkages, except at the terminal ends of the polymer wherein $X^1$ and $X^4$ represent hydroxy of any stereochemistry; and wherein:

Y is selected from the group consisting of:

(1) a moiety of the formula:

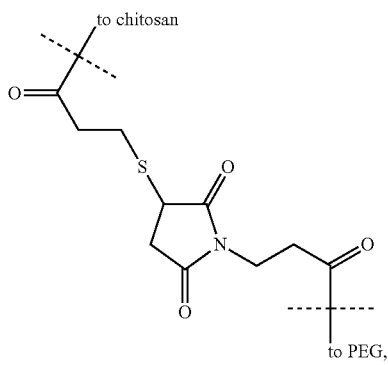

and (2) a moiety of the formula:

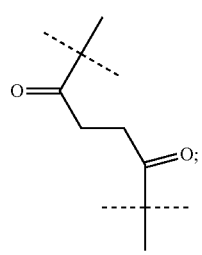

R1 is a moiety of the formula:

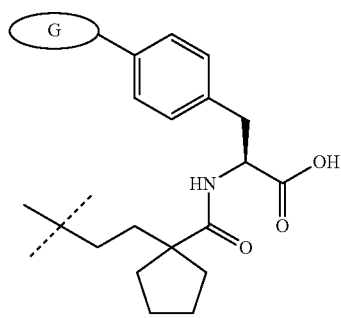

wherein

G is 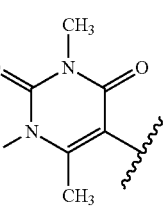

In one embodiment there is provided a chitosan polymer derivative of formula I:

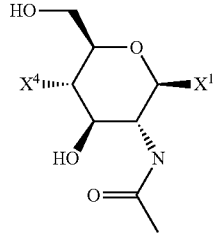
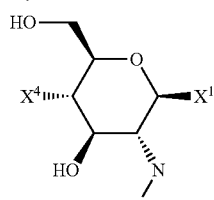
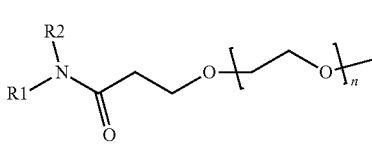
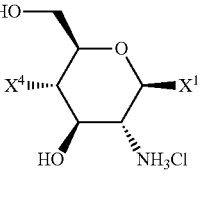

wherein the monomers of formula I are covalently linked to each other by a single oxygen atom at positions $X^1$ and $X^4$ which represent beta-1-4 linkages, except at the terminal ends of the polymer wherein $X^1$ and $X^4$ represent hydroxy of any stereochemistry; and wherein:

Y is selected from the group consisting of:

(1) a moiety of the formula:

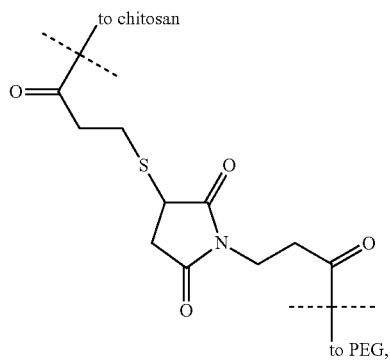

and (2) a moiety of the formula:

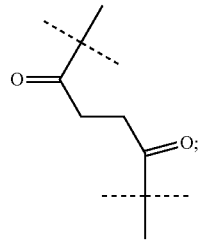

R1 is a moiety of the formula:

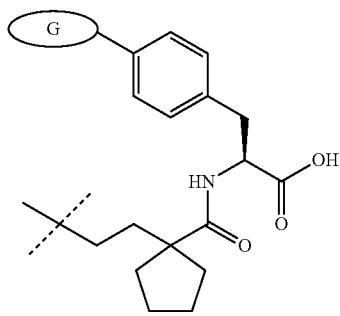

wherein

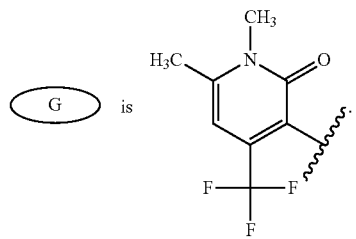 [SMILES: *c1c(C(F)(F)F)cc(C)n(C)c1=O] is

General Synthesis of the Compounds of the Invention

Chitosan in various forms is widely available. There are many commercial sources having a specified degree of deacetylation and molecular weight range. The degree of de-acetylation may be changed by treatment with a strong base according to published methods. It is possible to size chitosans into narrower molecular weight ranges through the use of dialysis bags which have different molecular weight cut-offs. Methods for manipulation of chitosan in this way have been published and are known to those skilled in the art.

Suitable processes for synthesizing chitosan polymer derivatives of formula I are provided in the examples. Generally, chitosan polymer derivatives of formula I can be prepared according to the schemes illustrated below. Unless otherwise indicated, the variables such as R1, R2, X1, X2, Y, etc. in the schemes below are defined in the same manner as defined previously for the genus of formula I.

Integrin targeting chitosan polymer derivatives consisting of three monomers of formula I:

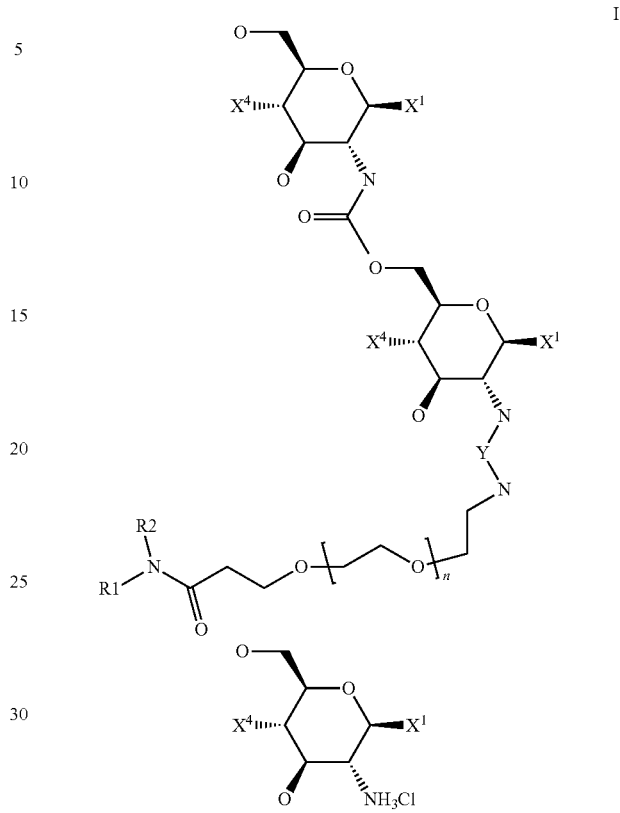

wherein the variables are as defined in the detailed description and claims were made in the following general manner as shown in the following schemes.

General Synthesis of Maleimide-(PEG)n-Integrin Antagonists Conjugating Agents

Compounds such as 4 of various lengths of PEG are commercially available (such as from Pierce BioScience). Such compounds can also be made as shown in Scheme I by acylating the amino terminal of PEG amino acids with 3-(2,5-dioxo-2,5-dihydro-pyrrol-1-yl)-propionic acid under amide bond forming conditions, followed by formation of reactive N-hydroxysuccinic esters by reaction of N-hydroxy succinic acid under ester forming conditions. Reaction with compounds containing primary or secondary amines such as 5 are conducted in aprotic or protic solvents in the presence of a basic amine such as DIEA (diisopropylethylamine) at room temperature generating PEGylated intermediates such as 6:

Scheme 1

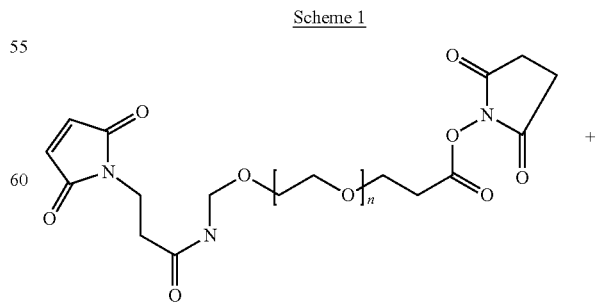

4

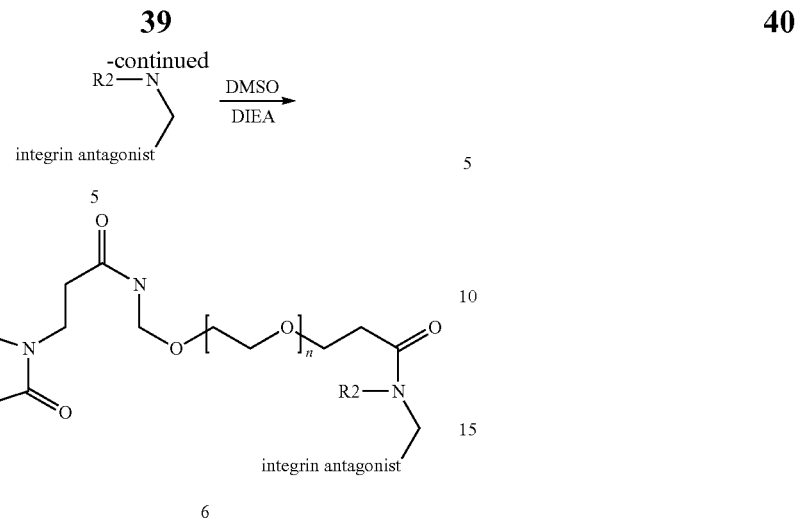
Specifically for this invention, intermediate 2 is reacted with 4 to produce the maleimide intermediate 7:
Scheme 2
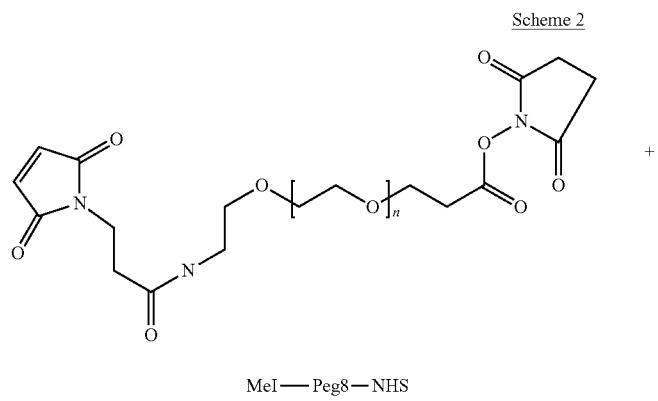
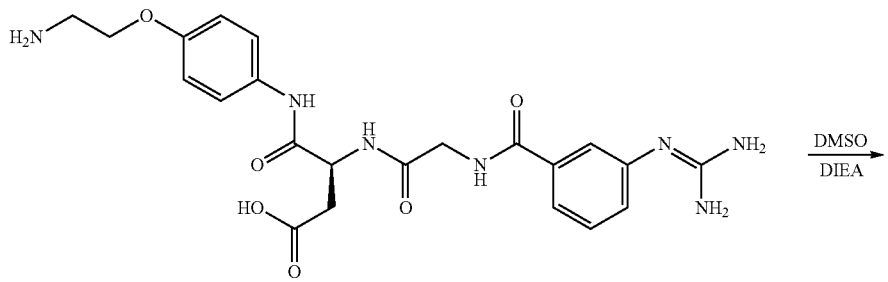

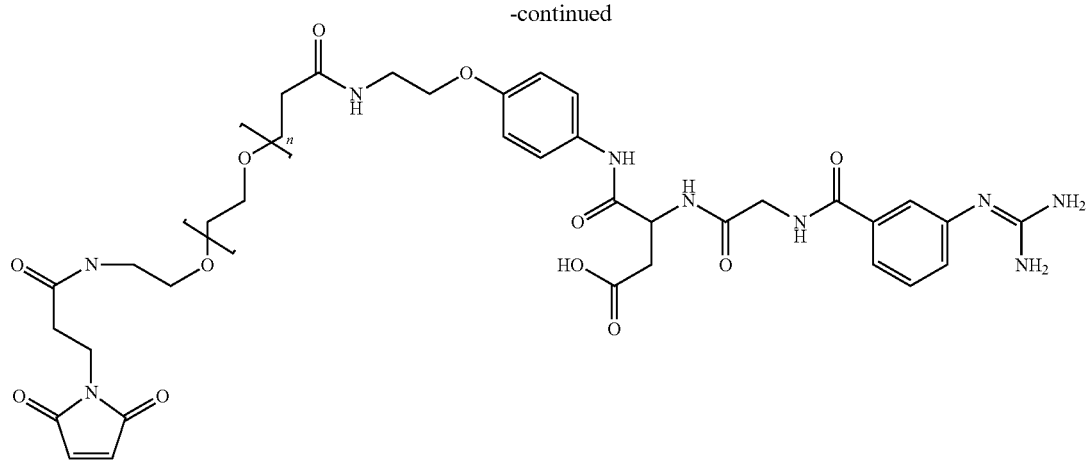
7
In a similar manner, intermediate 8 is reacted with 4 to produce the maleimide intermediate 9:
Scheme 3
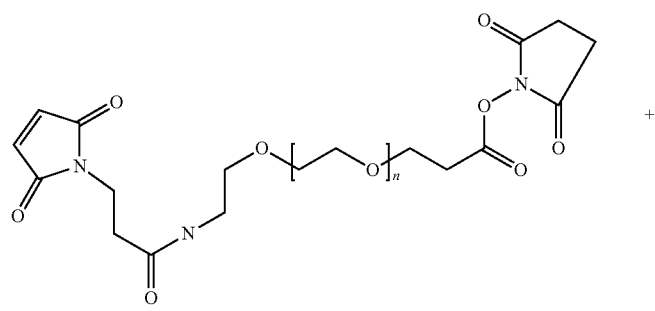
4
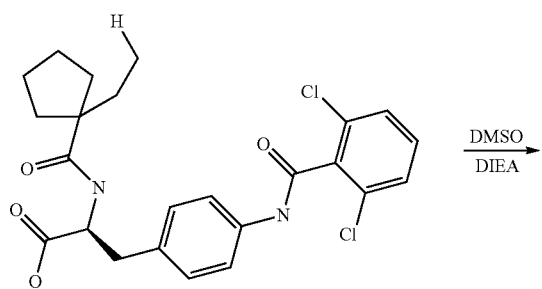
8

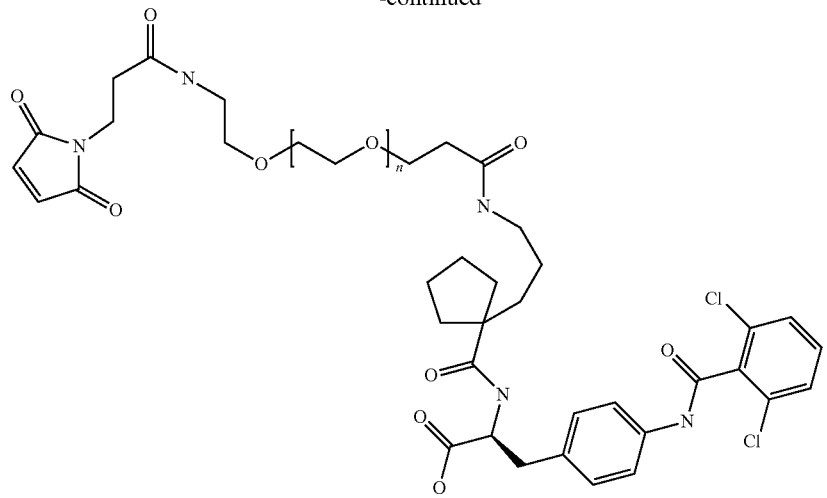

9

With a chitosan of a desired molecular weight and degree of de-acetylation (10), 3-acetylsulfanyl-propionic acid 11 is reacted in the presence of 1-ethyl-3-(3-dimethylaminopropyl)carbodiimide hydrochloride (EDC-HCl) and hydroxybenzotriazole, forming protected thiolated chitosan 12 as shown in Scheme 4:

Scheme 4

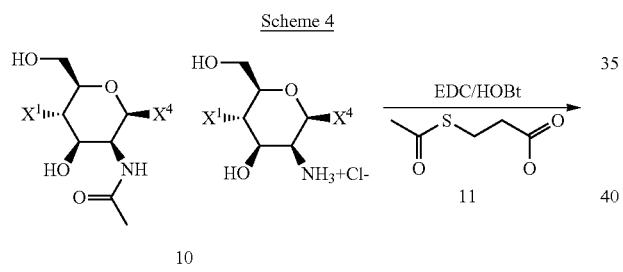

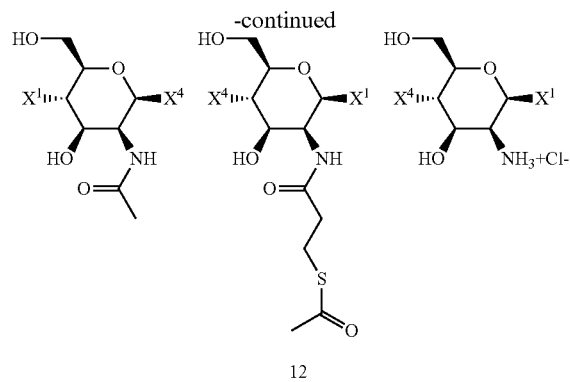

12

Protected thiolated chitosan 12 is deprotected with 0.1N aqueous HCl for 4 hours at 100° C., thereby forming thiolated chitosan 13 as shown in Scheme 5:

Scheme 5

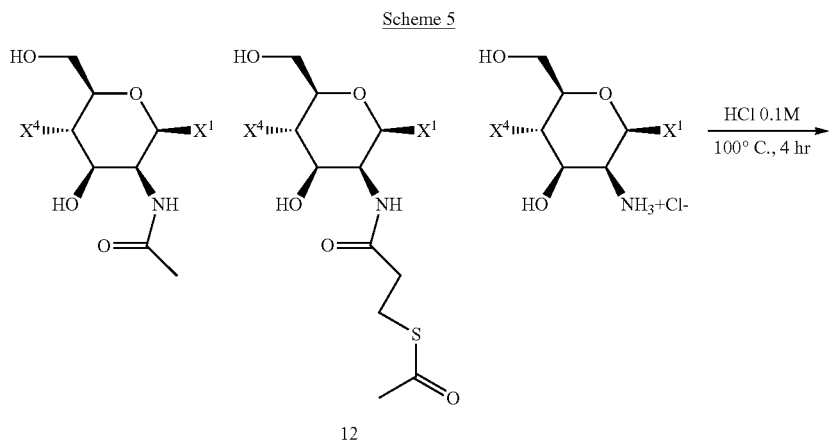

12

-continued
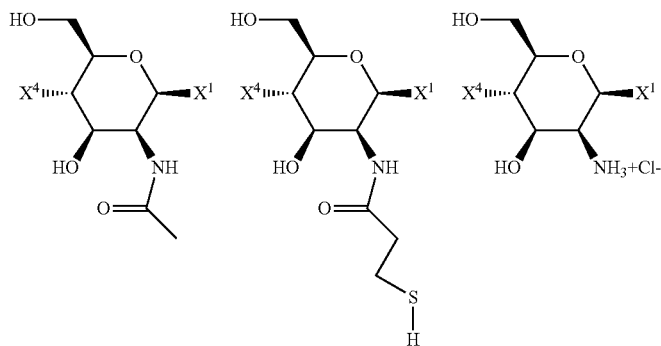
13
With thiolated chitosan 13, reaction with PEGylated targeting ligand 6 is conducted in aqueous conditions at room temperature, for small molecule—PEG—chitosan conjugate (Scheme 6). The degree of small molecule loading or substitution is controlled by the extent of reaction with 3-acetylsulfanyl-propionic acid as shown in Scheme 4.
Scheme 6
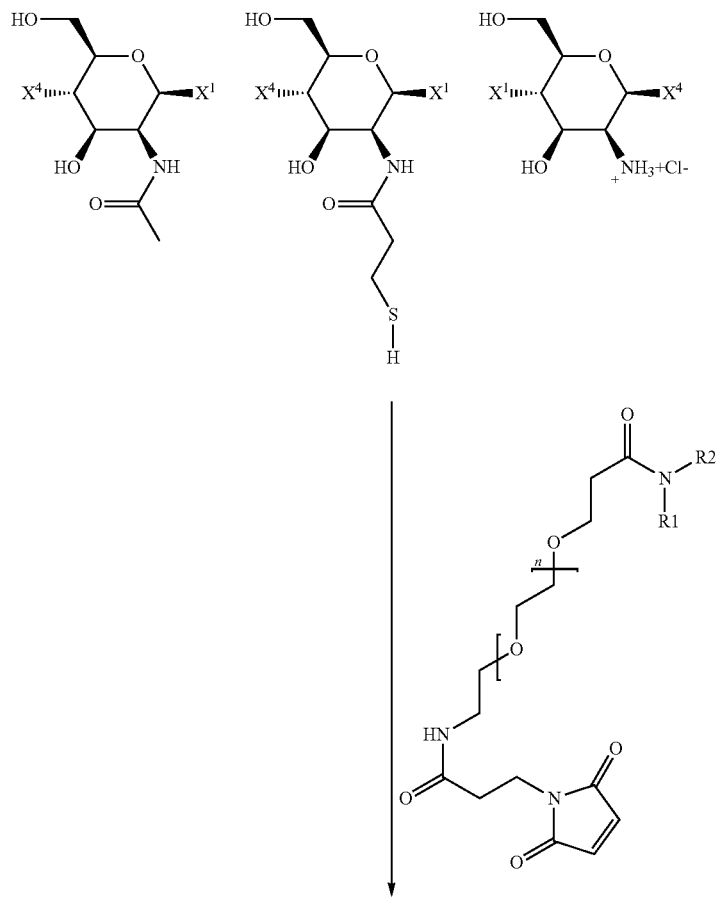

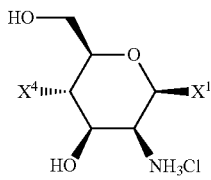
-continued
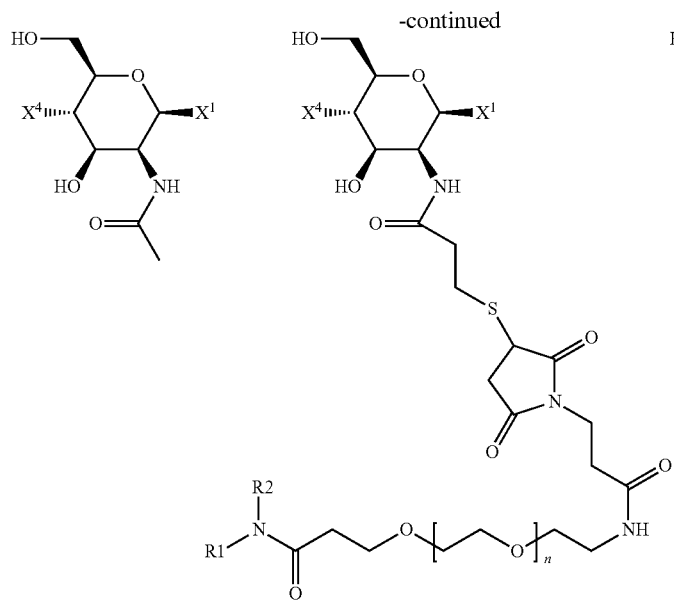

Intermediate 2 where m=1, αVβ3 targeting module, can be synthesized as shown in the Scheme 8 below. Briefly, meta-aminobenzoic acid 14 is reacted with N,N-di-Boc-methylthiourea 15 in DMF, dichloromethane, and pyridine in the presence of mercuric acetate. At this point, benzyl ester protected glycine is coupled to the carboxylic acid of the product of the above reaction under standard peptide forming conditions. The benzyl ester is removed by hydrogenolysis conditions, thereby providing the free acid 16. In a separate reaction sequence, para-nitrophenol 17 is coupled with (2-hydroxy-ethyl)carbamic acid tert-butyl ester in the presence of triphenyl phosphine and diisopropyl azodicarboxylate in an aprotic solvent such as tetrahydrofuran. The nitro group of this product is reduced to the corresponding aniline 18, which is coupled under amide bond forming conditions to N-α-Fmoc-L-aspartic acid β-tert-butyl ester. After removal of the amino protecting group Fmoc, by treatment with piperidine, the amino terminus is coupled to intermediate 19 again under standard amide bond forming conditions to form intermediate 16. Upon treatment with a strong acid, such as trifluoracetic acid, intermediate 2 is formed and is isolated by purification methods well known to those skilled in the art:

Scheme 8

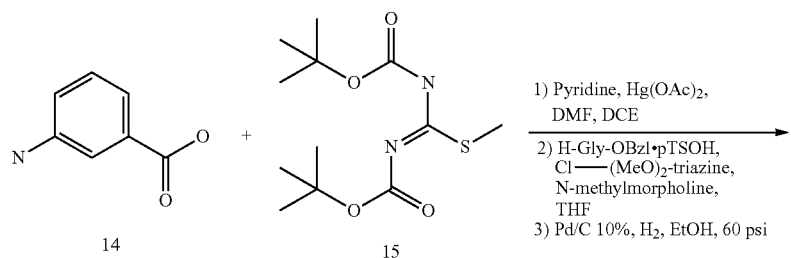

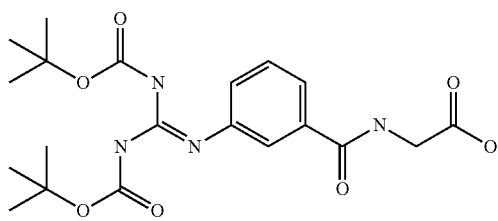

16

-continued
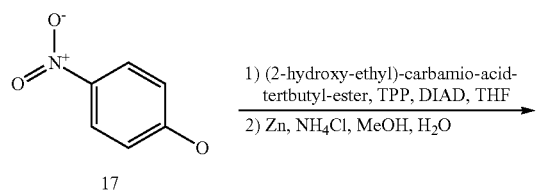
17
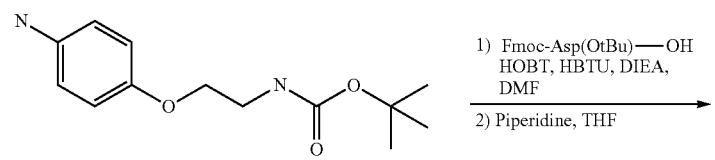
18
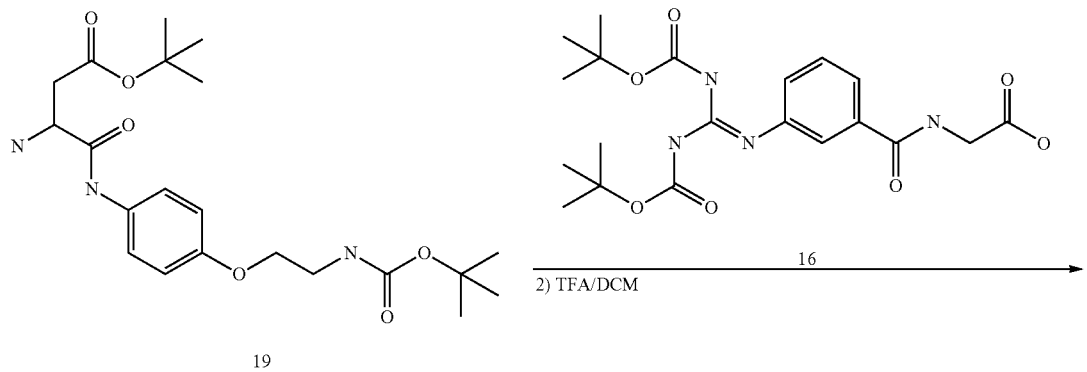
19
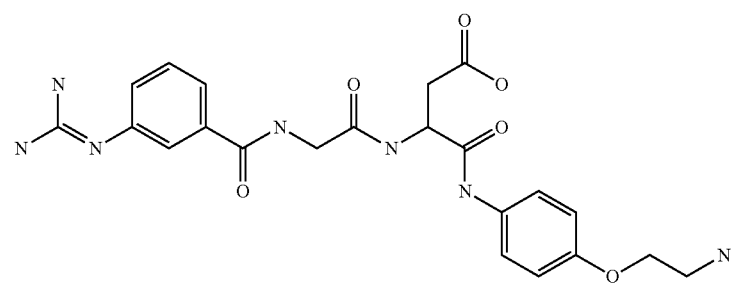
2

The 3-carbon chain amine analogue of 2 where m=1 can be prepared in a similar manner as shown in Scheme 8 using (3-bromopropyl)carbamic acid tert-butyl ester instead of (2-hydroxyethyl)carbamic acid tert-butyl ester.

Intermediate 3 can be synthesized in a manner similar to that as has been reported (Sidduri, A. et al. *Bioorganic & Medicinal Chemistry Letters*, 2002, 12, 2475-2478) and as shown in Scheme 9:

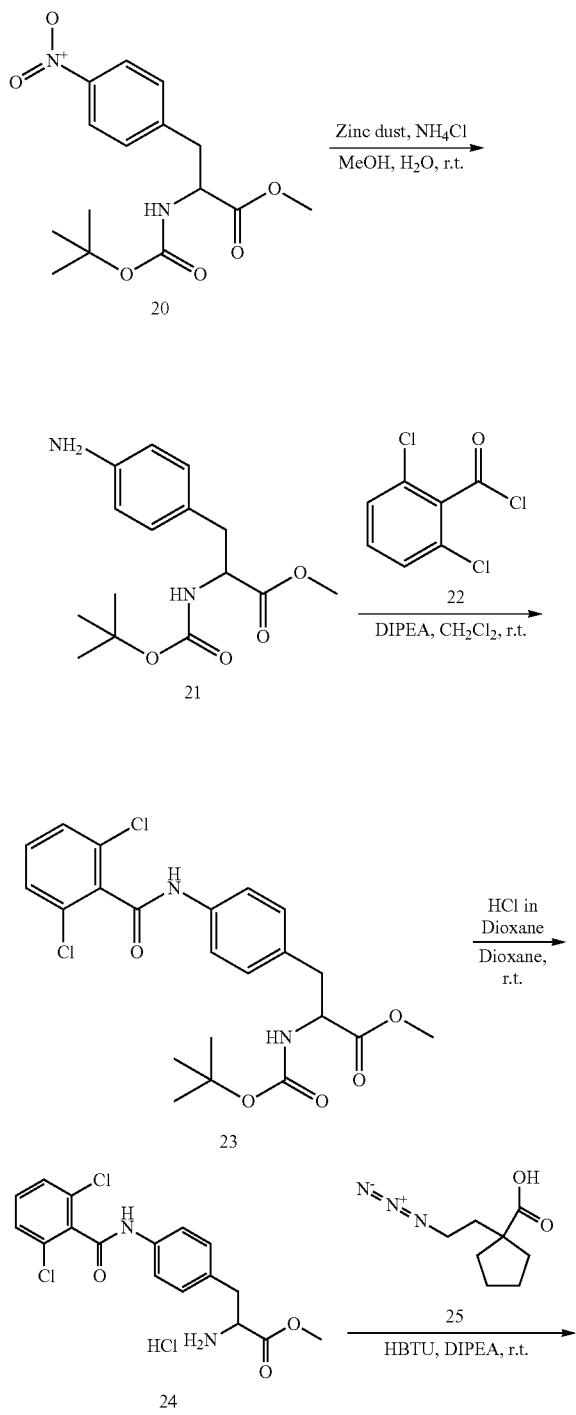

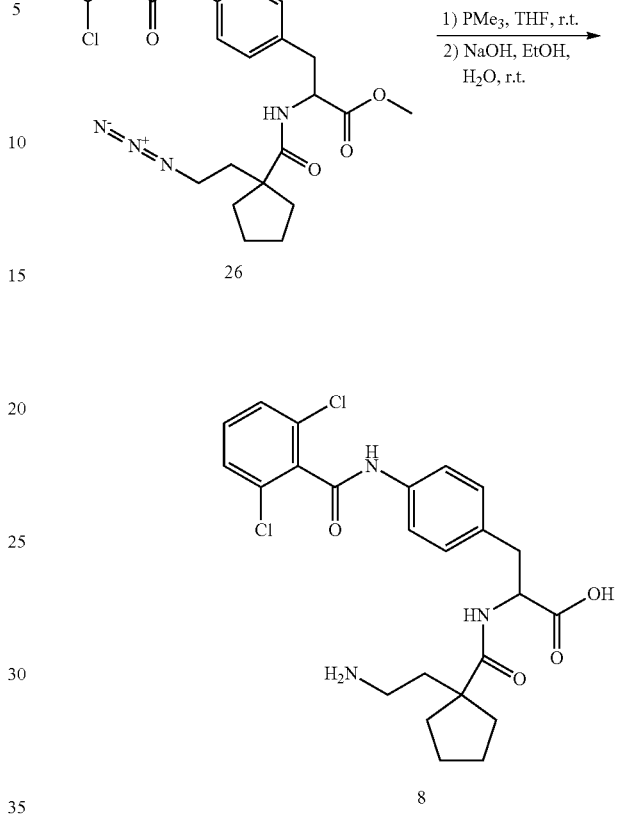

Specifically, as shown in Scheme 9, intermediate 21 was created from commercially available (S)-3-[4-nitrophenyl]-2-tert-butoxycarbonylamino-propionic acid 20. The nitro group of commercially available starting material 20 in a methanol solution was reduced with zinc dust in the presence of ammonium chloride at room temperature over the course of several hours, resulting in amine 21. Other methods for nitro reduction are known to those skilled in the art. Aniline 21 was acylated with benzoyl halide derivatives such as 2,6-dichlorobenzoyl chloride 22 in an aprotic solvent such as dichloromethane in the presence of a base such as di-isopropyl-ethyl amine at room temperature. In this manner, amide 23 was formed. The t-butylcarbonyl (Boc) amine protecting group was removed according to standard methods known to those skilled in the art, such as by the treatment with an HCl solution in dioxane at room temperature; resulting in hydrochloride 24. Hydrochloride 24 was treated with amide bond forming conditions (also well known to those skilled in the art) in presence of known 1-(2-azido-ethyl)-cyclopentanecarboxylic acid 25 resulting in the production of di-amide 26. The azide group of intermediate 26 was reduced by treatment with a tri-alkyl phosphine in an aprotic solvent such as tetrahydrofuran at room temperature. Further, the methyl ester was saponified by treatment with sodium hydroxide in a solvent mixture such as ethanol and tetrahydrofuran at an elevated temperature such as 50° C. and for 15 hours. This process resulted in the formation of intermediate 8 which may also be presented as a zwitterion.

The synthesis of the integrin antagonist of the formula:
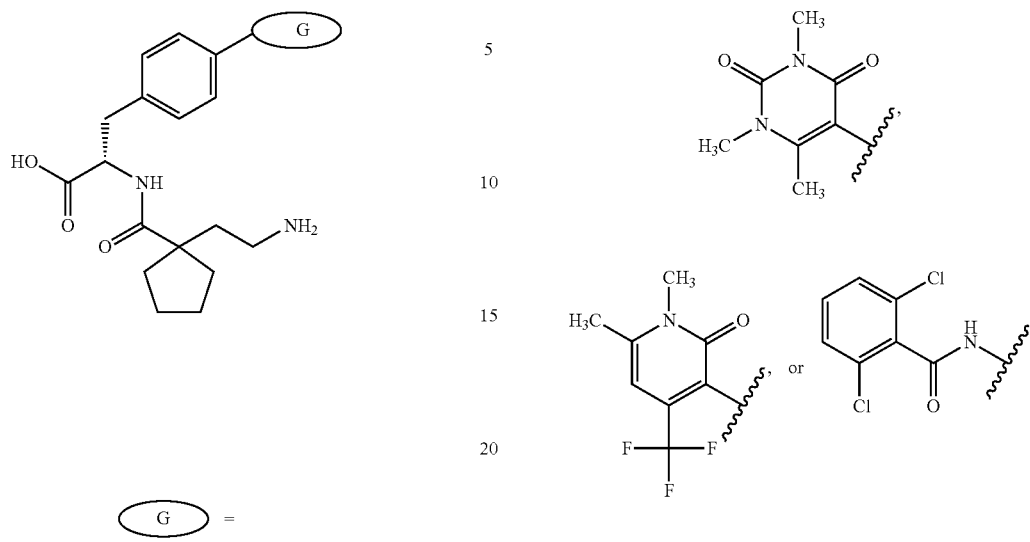
wherein:
can be efficiently accomplished in accordance with Scheme 10:
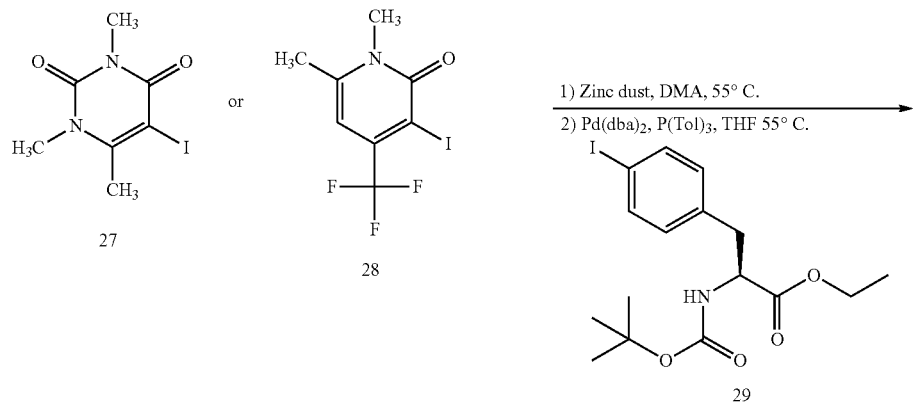
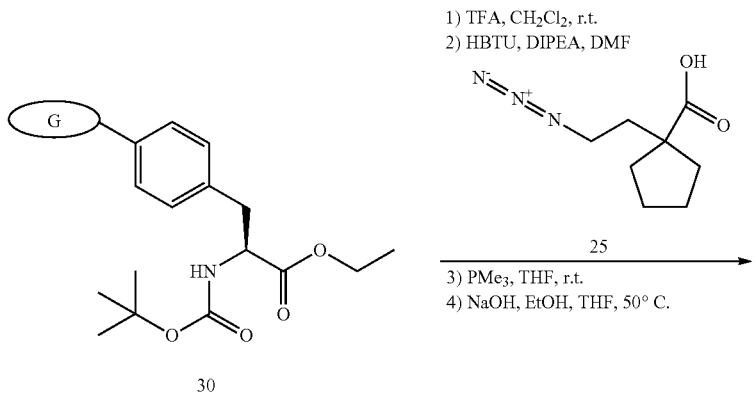

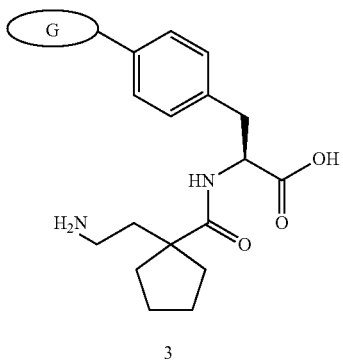

3

Rings represented by G may be installed into intermediate 3 as shown in Scheme 10. Then intermediate 3 is made available for subsequent coupling in the similar manner as that shown in Schemes 3 and to produce a target module ready for coupling according to Scheme 1 enroute to making the chitosan polymer derivatives of formula I. Detailed synthesis methods of the preparation of intermediate 27 in Scheme 10 above are published in U.S. Pat. Nos. 6,388,084 B1 and 6,380,387 B1, Briefly, aryl or heteroaryl zinc reagents are formed from known intermediates 27 or 28 in an anhydrous solvent such as dimethyl acetamide (DMA). At this point the zinc reagents are reacted with commercially available (S)-2-tert-butoxycarbonylamino-3-(4-iodo)phenyl]propionic acid ethyl ester 29 in the presence of a palladium catalysts such as Pd(dba)$_2$ and in the presence of palladium ligands tri-toluylphosphine in an aprotic solvent such as tetrahydrofuran (THF) at 50° C. In this manner, an intermediate of general structure 30 is formed. Intermediate 30 is then transformed to intermediate 3 in four steps which are routine to those skilled in the art. First, the removal of the amino protecting group N-tert-butoxycarbonyl is effected in the presence of a strong acid such as trifluoroacetic acid (TFA) in dichloromethane (CH$_2$Cl$_2$) solvent. Second, cyclic intermediate 15 is coupled to the amino group revealed in the previous step using standard amide bond forming conditions well known to those skilled in the art. Third, the azido group is reduced to the corresponding amine using trimethyl phosphine in THF and finally the carboxylic ester is saponified using sodium hydroxide in a solvent mixture of THF and ethyl alcohol (EtOH) at 50° C. for 15 hours.

For compounds of general structure 4, different PEG lengths are available or easily made by those skilled in the art; specifically, n=8-24. The use of 9H-fluoren-9-yl-methoxycarbonyl protection (N-Fmoc) of the amino terminus of the pegylation reagents is preferred. The N-Fmoc protecting group is removed by treatment with a secondary amine such as dimethylamine in THF (tetrahydrofuran) or piperidine in DMF (dimethylformamide). Having deprotected the amino terminus of the pegylated conjugate 18, reaction with commercially available succinic anhydride is performed as a means to expose a carboxylic acid group for subsequent coupling to the amino terminus of intermediate 8, using amide bond forming reaction conditions that are well known to those skilled in the art.

In detail, the present invention relates compounds of formula 1, in the case where Y represents a succinimide linker as shown below. The synthesis shown in Scheme 11 using Intermediate 31 provides sufficient detail for replication by those skilled in the art. This method is also applicable to other integrin targeting small molecules which contain a nucleophilic amine and appropriate carboxylic acid group, preferably tert-butyl ester, as necessary. Specifically, intermediate 31, is reacted with commercially available PEGylating reagent 32, in presence of HBTU and diisopropylethylamine in an aprotic solvent such as DMSO thereby yielding intermediate 33. At this time, the Fmoc amine protecting group is removed with a secondary amine reagent, such as DBU (34) in a solvent such as DMF in the presence of a thiol quenching reagent such as 35. At this time, treatment of the amine-deprotected intermediate with succinic anhydride 36 is followed by a preferred method for activation with the use of hydroxy-2,5-dioxopyrrolidine-3-sulfonic acid (Sulfo-NHS, 38) as the catalyst for a coupling, mediated by 1-ethyl-3-(3-dimethylaminopropyl)carbodiimide hydrochloride (EDC-HCl) in the presence of a base such as di-isopropylethylamine (DIPEA) and in a solvent such as dimethylsulfoxide (DMSO). This results in derivatizing reagent 39. Reaction of 39 with an appropriately de-acetylated chitosan 11, provides small molecule targeted chitosans of general formula I as previously described in the detailed description and claims:

Scheme 11
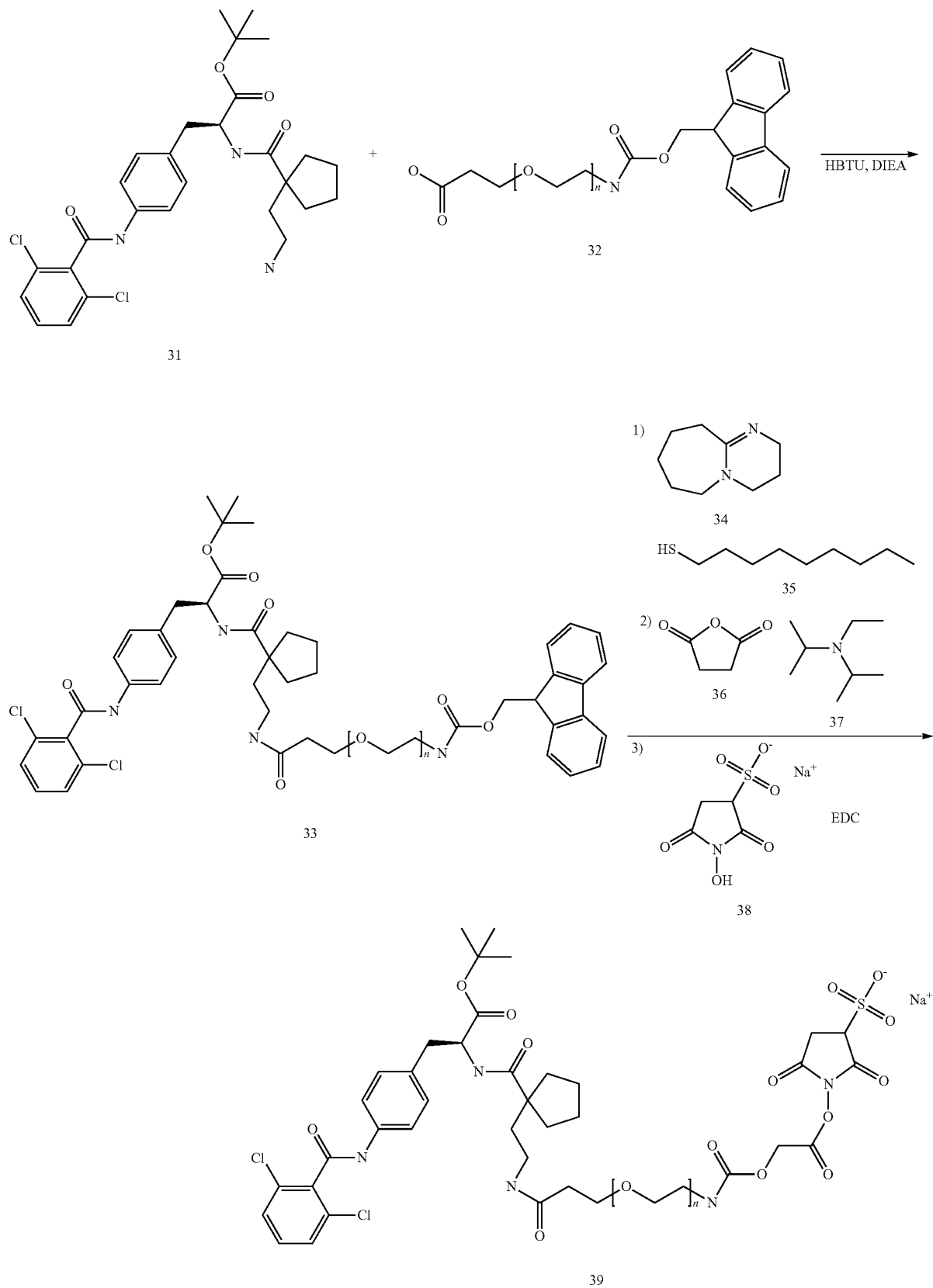

General Synthesis of siRNA Nanoparticles with Chitosan Derivatives that are Covalently Linked with Small Molecule Integrin Antagonist for Targeted Delivery of siRNA siRNA nanoparticles containing chitosan polymer derivatives of formula I can be prepared by combining aqueous solutions of siRNA with the chitosan polymer derivatives in buffers, concentrations and ratios known to those skilled in the art or as widely published. Nanoparticles form spontaneously according to the electrostatic association of the negatively charged siRNA with positively charged chitosan. The size and charge of the siRNA/derivatized chitosan nanoparticle is controlled in part by the N to P ratio (the ratio of the average number of basic chitosan amino groups to negatively charged phosphodiester groups of the siRNA). In particular embodiments, the N to P ratio is between 2 and 200, 50 being preferred. The average molecular weight of the chitosan polymer derivatives varies between 10,000 and 250,000 Da, with greater than 100,000 Da being preferred. The combination with other derivatized or underivatized chitosans of different molecular weights is one means to control the size and charge of the nanoparticle.

Utility

The chitosan polymer derivatives of formula I are useful for conjugation or in formulating compositions to improve the delivery of therapeutic agents such as small molecules, peptides, or nucleic acids (i.e. siRNA) to target cells expressing VLA-4 and αVβ3 dimers.

Accordingly, the compositions of the present invention containing chitosan polymer derivatives of formula I may be used to encapsulate, condense or otherwise formulate therapeutic agents such as small molecules, peptides, or nucleic acids (i.e., siRNAs), for treating various diseases and conditions that are associated with the expression of VLA-4 and αVβ3. Such disease and conditions include cancer and may include various metabolic related diseases.

In particular embodiments, the present invention comprises a method of treating or preventing cancer in a mammal (preferably a human) in need of such treatment, wherein the method comprises administering a therapeutically effective amount of a composition containing a chitosan polymer derivative of formula I. In a further embodiment there is provided the use of a compound of formula I for the treatment or prophylaxis of inflammation, cancer, or a metabolic disease or condition. In a further embodiment there is provided the use of a compound of formula I for the the preparation of a medicament for the treatment or prophylaxis of inflammation, cancer, or a metabolic disease or condition.

In particular embodiments such compositions are chitosan-siRNA nanoparticles. Such compositions can be administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The "effective amount" of the compound to be administered will be governed by such considerations as the minimum amount necessary to inhibit the expression of the target protein and avoid unacceptable toxicity. For example, such amount may be below the amount that is toxic to normal cells, or the mammal as a whole. The compositions containing a compound of formula I of the invention may be administered by parenteral, intraperitoneal, and intrapulmonary administration. Parenteral infusions include intramuscular, intravenous, intraarterial, intraperitoneal, or subcutaneous administration.

EXAMPLES

The invention will be more fully understood by reference to the following examples. They should not, however, be construed as limiting the scope of the invention.

Reagents were purchased from Aldrich, Sigma, and Pierce BioScience or other suppliers as indicated below and used without further purification. The purification of multi-milligram to multi-gram scale was conducted by methods known to those skilled in the art such as elution of silica gel flash column. Preparative flash column purifications were also effected in some cases by the use of disposable prepacked multigram silica gel columns (RediSep) eluted with a CombiFlash system. Biotage™ and ISCO™ are also flash column instruments that may be used in this invention for purification of intermediates.

For the purpose of judging compound identity and purity, LC/MS (liquid chromatography/mass spectroscopy) spectra were recorded using the following system. For measurement of mass spectra, the system consists of a Micromass Platform II spectrometer: ES Ionization in positive mode (mass range: 150-1200 amu). The simultaneous chromatographic separation was achieved with the following HPLC system: ES Industries Chromegabond WR C-18 3u 120 Å (3.2×30 mm) column cartridge; Mobile Phase A: Water (0.02% TFA) and Phase B: Acetonitrile (0.02% TFA); gradient 10% B to 90% B in 3 minutes; equilibration time of 1 minute; flow rate of 2 mL/minute. In some cases, ammonium acetate at 20 millimolar concentration was used as a modifier for effective ionization during preparative HPLC. In such cases, the ammonium salt was isolated.

For some separations, the use of super critical fluid chromatography may also be useful. Super critical fluid chromatography separations were performed using a Mettler-Toledo Minigram system with the following typical conditions: 100 bar, 30° C., 2.0 mL/min eluting a 12 mm AD column with 40% MeOH in super critical fluid $CO_2$. In the case of analytes with basic amino groups, 0.2% isopropyl amine was added to the methanol modifier.

Compounds were characterized either by $^1$H-NMR using a Varian Inova 400 MHz NMR Spectrometer or a Varian Mercury 300 MHz NMR Spectrometer as well as by high resolution mass spectrometry using a Broker Apex-II high-resolution 4.7 T FT-Mass Spectrometer. Final compounds were also characterized by high resolution mass spectrometry using a LTQ CL Orbitrap sold by Thermo Electron.

Abbreviations used herein are as follows:
AIBN 2,2'-azobisisobutyronitrile
Bu butyl
DCE 1,2-dichloroethane
DCM: dichloromethane
DBU 1,8-diazabicyclo[5.4.0]undec-7-ene
DIAD diisopropyl azodicarboxylate
DIPEA diisopropylethylamine
DMF N,N-dimethylformamide
DMSO dimethylsulfoxide
EDC-HCl 1-ethyl-3-(3-dimethylaminopropyl)carbodiimide hydrochloride
EtOAc ethyl acetate
EtOH ethyl alcohol
FCC flash column chromatography h hour
HBTU O-(benzotriazol-1-yl)-N,N,N',N'-tetramethyluroniumhexafluorophosphate
HOBt hydroxybenzotriazole
HPLC high pressure liquid chromatography
HRMS high resolution mass spectra
LRMS low resolution mass spectra
LC liquid chromatography
L-Pro L-proline
MCPBA meta-chloroperoxybenzoic acid
MeOH methyl alcohol
MW microwave
NIS N-iodosuccinimide
NBS N-bromosuccinimide
NMP 1-methyl-2-pyrrolidinone
PdCl$_2$(dppf) [1,1'-Bis(diphenylphosphino)ferrocene]dichloropalladium(II)
PEGn Polyethylene glycol repeating n times (e.g., PEG2=—OCH2CH2OCH2CH2-)
PG protecting group
PyBroP bromo-tris-pyrrolidino-phosphonium hexafluorophosphate
rt room temperature
TBAF tetrabutylammonium fluoride
TBDMS tert-butyl-dimethylsilyl
TBTU 2-(1H-benzotriazole-1-yl)-1,1,3,3-tetramethyluronium tetrafluoroborate
TMS trimethylsilyl
TMSSMe (methylthio)trimethylsilane
TEA triethylamine
TEMPO 2,2,6,6-tetramethylpiperidine-1-oxyl
TFA trifluoroacetic acid
THF tetrahydrofuran
TPP triphenylphosphine Preparation of Ligands αvβ3 Ligand 1:

(S)—N-[4-[3-[[3-[2-[2-[2-[2-[2-[2-[2-[2-[3-(2,5-dioxo-2,5-dihydro-pyrrol-1-yl)-propionylamino]ethoxy]ethoxy]ethoxy]ethoxy]ethoxy]ethoxy]ethoxy]ethoxy]-1-oxopropyl]amino]propoxy]-phenyl]-3-[2-[3-[guanidino]-benzoylamino]-acetylamino]-succinamic acid Step 1: Preparation of 3-(N,N-bis-tert-butoxycarbonylguanidine)-benzoic acid

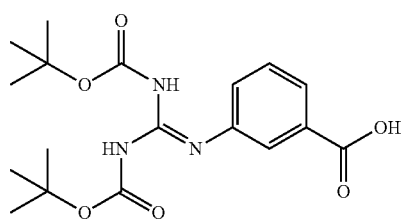 [SMILES: CC(C)(C)OC(=O)NC(=Nc1cccc(C(=O)O)c1)NC(=O)OC(C)(C)C]

A solution of the 3-aminobenzoic acid (823 g, 0.60 mole), N,N'-bis(tert-butoxycarbonyl)-S-methylisothiourea (1,3-diboc-2-methylisothiourea, CAS #107819-90-9) (174.2 g, 0.6 mole), and pyridine (94.92 g, 97 mL, 1.20 mole, 2.0 equivalents) in a mixture of anhydrous dimethylformamide (600 mL) and anhydrous 1,2-dichloroethane (600 mL) was treated with mercuric acetate (95.6 g, 0.30 mole, 0.5 equivalents) and stirred with overhead mechanical stirrer for 5 h at room temperature. Then, the solids were filtered off, washed with dichloromethane and the combined filtrate and washings were evaporated to afford the crude product (~307 g). To this crude material methanol (240 mL) was added and the mixture was stirred vigorously for 2 h. Then, slowly add 2400 mL of water while stirring vigorously. Filter, wash the solids thoroughly with water and suck dry overnight to obtain the 3-(N,N-bis-tert-butoxycarbonylguanidino)-benzoic acid in more than theoretical yield. Pump dry on high vac. The weight obtained was over the theoretical value (theoretical=227.6 g, actual=251.2 g $^1$H NMR implies ~10% of DMF present)

Step 2: Preparation of 2-(3-(N,N-bis-tert-butoxycarbonylguanidino)benzoyl)-amino-acetic acid benzyl ester

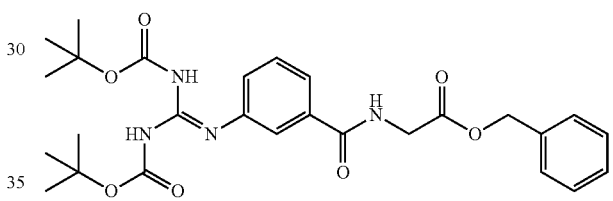

A light brown solution of 3-(N,N-bis-tert-butoxycarbonylguanidino)benzoic acid (171.56 g, 0.4073 mole), 2-chloro-4,6-dimethoxy-triazine (71.52 gm, 0.4073 mole), and N-methylmorpholine (41.2 gm, 44.78 mL, 0.4073 mole) in anhydrous tetrahydrofuran (1600 mL) was stirred (overhead mechanical stirrer) for 2 h at room temperature and then the glycine benzylester p-TsOH salt (137.44 g, 0.4073 mole) and a second equivalent of N-methylmorpholine (41.2 g, 44.78 mL, 0.4073 mole) were added. The resulting mixture was stirred at room temperature for 36 h. Then, the tetrahydrofuran was removed on the rotary evaporator and ethyl acetate (2000 mL) was then added. The resulting mixture was washed successively with ice cold 0.5 N HCl (3×1000 mL), water (1×1000 mL), 5% aqueous sodium carbonate (1×1000 mL), water (1×1000 mL), saturated aqueous sodium chloride (1×1000 mL) and dried over sodium sulfate. The solids were filtered off, and the solvent was evaporated to afford the crude product (228.5 g) as an oil. The crude material was purified by chromatography on the Waters Prep500 (10 runs) using dichloromethane:hexane:ethyl acetate=40:45:15 as the eluent, to afford 2-(3-(N,N-bis-tert-butoxycarbonylguanidino)benzoyl)-amino-acetic acid benzyl ester (79.3% yield). (Note: on the first runs obtained 152 g of clean material and 33 g of slightly impure material which was rechromatographed in two runs). ES(±)-HRMS role calcd. for $C_{27}H_{34}N_4$ (M+H)$^+$ 527.2500, obsd. 527.2499.

Step 3: Preparation of 2-(3-(N,N-bis-tert-butoxycarbonylguanidino)benzoyl)-amino-acetic acid

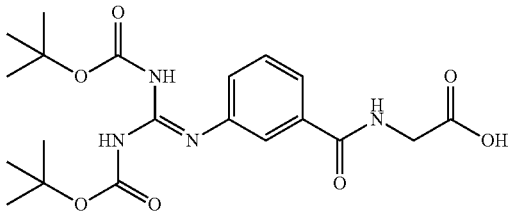 [SMILES: CC(C)(C)OC(=O)NC(=Nc1cccc(C(=O)NCC(=O)O)c1)NC(=O)OC(C)(C)C]

A solution of 2-(3-(N,N-bis-tert-butoxycarbonylguanidino)benzoyl)-amino-acetic acid benzyl ester (170.0 g, 0.323 mole) in absolute ethanol (2000 mL) was hydrogenated over 10% Pd on carbon (20 g wet catalyst, which contains ~50% water) at 60 psi overnight (18 h) in the High Pressure facility at room temperature. The catalyst was filtered off, and solvent was evaporated to afford the product. The product was azeotroped with toluene (3 times) to remove all the ethanol, to afford 2-(3-(N,N-bis-tert-butoxycarbonylguanidino)benzoyl)-amino-acetic acid (97.88% yield) as a white solid. ESN-HRMS m/e calcd. for $C_{20}H_{28}N_4O_7$ (M+H)$^+$ 437.2031, obsd. 437.2030.

Step 4: Preparation of [3-(4-nitro-phenoxy)-propyl]-carbamic acid tert-butyl ester

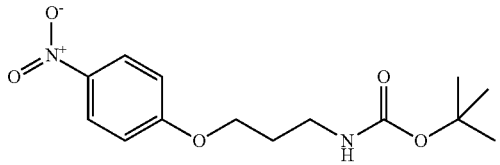 [SMILES: CC(C)(C)OC(=O)NCCCOc1ccc([N+](=O)[O-])cc1]

To a solution of (3-hydroxy-propyl)-carbamic acid tert-butyl ester (7.03 g, 40.1 mmol) in anhydrous THF (40 mL) were added 4-nitrophenol (5.07 g, 36.5 mmol), triphenylphosphine (10.5 g, 40.1 mmol) at room temperature under nitrogen atmosphere. The resulting solution was cooled to ~0° C. with an ice-water bath and then diisopropyl azodicarboxylate (DIAD, 8.1 g, 40.1 mmol) was added drop-wise for 15-20 minutes. After addition, the solution was warmed to room temperature and stirred for 15 h at which time LCMS analysis indicated the presence of 16% of the starting material. Then, another 0.1 equivalents of all the above reagents were added and the reaction mixture was stirred for another 15 h. The solids were filtered off and were washed with ethyl acetate and then the filtrate was washed with saturated sodium chloride solution and dried over anhydrous magnesium sulfate. Filtration and concentration gave the crude residue which was purified using an ISCO (340 g) column chromatography to obtain [3-(4-nitro-phenoxy)-propyl]-carbamic acid tert-butyl ester (64% yield) as a white solid. ES(+)-HRMS m/e calcd. for $C_{14}H_{20}N_2O_5$ (M+Na)$^+$ 319.1264, obsd. 319.1266.

Step 5: Preparation of [3-(4-amino-phenoxy)-propyl]-carbamic acid tert-butyl ester

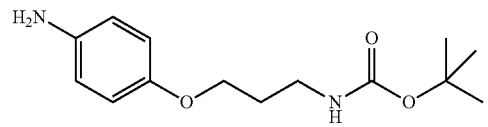 [SMILES: CC(C)(C)OC(=O)NCCCOc1ccc(N)cc1]

To a solution of [3-(4-nitro-phenoxy)-propyl]-carbamic acid tert-butyl ester (7.7 g, 26 mmol) in methanol (200 mL, heated to dissolve starting material) were added water (10 mL), ammonium chloride (20.9 g, 390 mmol, 15 equivalents), and zinc dust (16.4 g, 260 mmol, 10 equivalents, 3-portions) at room temperature. After addition of zinc dust, the reaction mixture was exothermic and the reaction mixture was stirred for 1-2 h at which time TLC analysis of the mixture indicated the absence of starting material. Then, the solids were filtered off and were washed with water and ethyl acetate and the organic compound from filtrate was extracted with ethyl acetate (3×100 mL). The combined extracts were washed with brine solution and dried over anhydrous magnesium sulfate. Filtration and concentration gave the crude residue which was purified using an ISCO (330 g) column chromatography to isolate [3-(4-amino-phenoxy)-propyl]-carbamic acid tert-butyl ester (79% yield) as a white solid. ES(+)-HRMS role calcd. for $C_{14}H_{22}N_2O_3$ (M+Na)$^+$ 289.1522, obsd. 289.1523.

Step 6: Preparation of (S)—N-[4-(3-tert-butoxycarbonylamino-propoxy)-phenyl]-3-(9H-fluoren-9-ylmethoxycarbonylamino)-succinamic acid tert-butyl ester

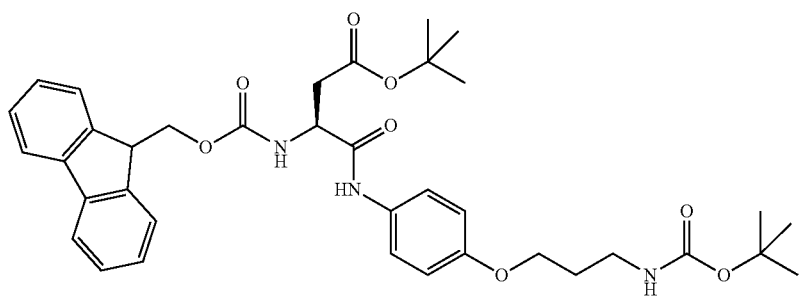 [SMILES: CC(C)(C)OC(=O)C[C@H](NC(=O)OCC1c2ccccc2-c2ccccc21)C(=O)Nc1ccc(OCCCNC(=O)OC(C)(C)C)cc1]

To a solution of [3-(4-amino-phenoxy)-propyl]-carbamic acid tert-butyl ester (5.41 g, 20.2 mmol) and (S)-2-(9H-fluoren-9-ylmethoxycarbonylamino)-succinic acid tert-butyl ester in DMF (40 mL) were added HOBT (3 g, 22.2 mmol), and DIPEA (8.52 g, 66.6 mmol) at room temperature. The resulting solution was cooled to 0° C. with an ice-bath and the solid HBTU (8.43 g, 22.2 mmol) was added in 3 portions during 5-10 minutes period. After addition, the cooling bath was removed and the reaction mixture was allowed to warm to room temperature and stirred for 2.5 h at which point LCMS analysis indicated the absence of starting material. Then, the reaction mixture was diluted with ethyl acetate (400 mL) and were washed with water (400 ml), saturated sodium bicarbonate solution (400 mL), and brine solution (400 mL). After drying over anhydrous magnesium sulfate, the filtration was concentrated and the crude residue was purified using an ISCO (330 g) column chromatography to isolate (S)—N-[4-(3-tert-butoxycarbonylamino-propoxy)-phenyl]-3-(9H-fluoren-9-ylmethoxycarbonylamino)-succinamic acid tert-butyl ester (95% yield) as a white solid. ES(+)-HRMS m/e calcd. for $C_{37}H_{45}N_3O_8$ (M+Na)$^+$ 682.3099, obsd. 682.3105.

Step 7: Preparation of (S)-3-amino-N-[4-(3-tert-butoxycarbonylamino-propoxy)-phenyl]-succinamic acid tert-butyl ester

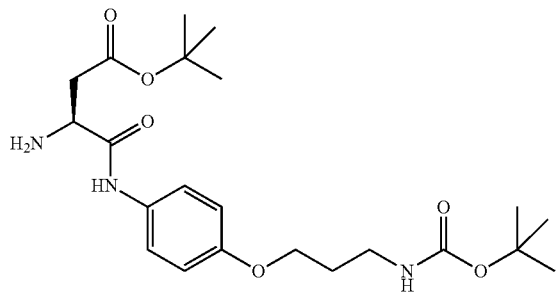 [SMILES: CC(C)(C)OC(=O)C[C@H](N)C(=O)Nc1ccc(OCCCNC(=O)OC(C)(C)C)cc1]

To a solution of (S)'N-[4-(3-tert-butoxycarbonylamino-propoxy)-phenyl]-3-(9H-fluoren-9-ylmethoxycarbonylamino)-succinamic acid tert-butyl ester (11 g, 16.67 mmol) in THF (95 mL) were added piperidine (4.26 g, 50 mmol) at room temperature. The resulting solution was stirred 4 h at which point LCMS analysis indicated the absence of starting material. Then, the solvent was removed under vacuum and the residue was azeotrophed with toluene to obtain a white solid which was dissolved in minimum ethyl acetate (25-30 mL) at hot condition and then it was diluted with hexanes (250-300 mL) until precipitation. The resulting solids were collected by filtration and washed with hexanes to obtain, after air drying, (S)-3-amino-N-[4-(3-tert-butoxycarbonylamino-propoxy)-phenyl]-succinamic acid tert-butyl ester (81% yield) as a white solid. ES(+)-HRMS m/e calcd. for $C_{22}H_{35}N_3O_6$ (M+Na)$^+$ 460.2418, obsd. 460.2416.

Step 8: Preparation of (S)-3-(2-(3-(N,N-bis-tert-butoxycarbonylguanidino)-benzoylamino)-acetylamino)-N-[4-(3-tert-butoxycarbonylamino-propoxy)-phenyl]-succinamic acid tert-butyl ester

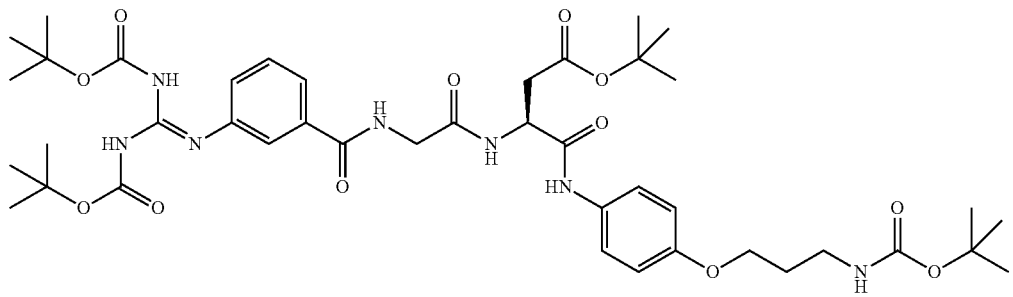 [SMILES: CC(C)(C)OC(=O)C[C@H](NC(=O)CNC(=O)c1cccc(N=C(NC(=O)OC(C)(C)C)NC(=O)OC(C)(C)C)c1)C(=O)Nc1ccc(OCCCNC(=O)OC(C)(C)C)cc1]

To a mixture of (S)-3-amino-N-[4-(3-tert-butoxycarbonylamino-propoxy)-phenyl]-succinamic acid tert-butyl ester (2.0 g, 4.58 mmol), 2-(3-(N,N-bis-tert-butoxycarbonylguanidino)benzoyl)-amino-acetic acid (2.0 g, 4.58 mmol), HBTU (1.91 g, 5.04 mmol), and HOBT (681 mg, 5.04 mmol) were added DMF (15 mL) followed by DIPEA (1.95 g, 15.12 mmol) at room temperature under nitrogen atmosphere. The resulting light brown solution was stirred for 2 days at which point lot of gel like solids were formed. Then, water (~50 mL) was added and the resulting light brown paste was dissolved in ethyl acetate (~200 mL) at hot condition. Then, the two layers were separated and the aqueous layer was extracted one more time with ethyl acetate (100 mL). The combined ethyl acetate extracts were washed with saturated sodium bicarbonate solution, water, and brine solution and then the organic layer was dried over anhydrous magnesium sulfate. Filtration and concentration gave the crude light brown solid which was purified using an ISCO (120 g) column chromatography to isolate (S)-3-(2-(3-(N,N-bis-tert-butoxycarbonylguanidino)-benzoylamino)-acetylamino)-N-[4-(3-tert-butoxycarbonylamino-propoxy)-phenyl]-succinamic acid tert-butyl ester (94% yield) as a white solid. ES(+)-HRMS calcd. for $C_{42}H_{61}N_7O_{12}$ (M+H)$^+$ 856.4450, obsd. 856.4451.

Step 9: Preparation of (S)—N-[4-(3-amino-propoxy)-phenyl]-3-(2-(3-(guanidino)-benzoylamino)-acetylamino)-succinamic acid trifluoroacetate salt

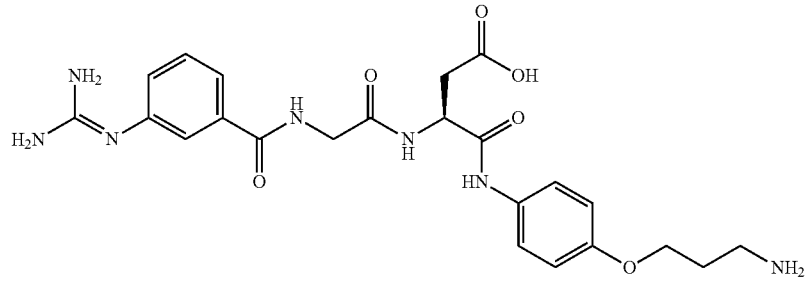 [SMILES: NCCCOc1ccc(NC(=O)[C@H](CC(=O)O)NC(=O)CNC(=O)c2cccc(N=C(N)N)c2)cc1]

To a solution of (S)-3-(2-(3-(N,N-bis-tert-butoxycarbonylguanidino)-benzoylamino)-acetylamino)-N-[4-(3-tert-butoxycarbonylamino-propoxy)-phenyl]-succinamic acid tert-butyl ester (3.7 g, 4.32 mmol) in dichloromethane (80 mL) was added an excess of trifluoroacetic acid (40 mL) at 0° C. (ice-bath) under nitrogen atmosphere. The resulting colorless solution was stirred for 1-2 h at this temperature and then it was allowed to warm to room temperature by removing the cooling bath. After stirring for 15 h, the solvent was removed under vacuum and the residue was azeotrophed with toluene. The resulting dark blue paste was triturated with tert-butyl methyl ether, but it did not give good solids. Then, the solvent was removed under vacuum and the residue was triturated with dichloromethane and diethyl ether. The resulting light brown solids were collected by filtration and washed with diethyl ether. After drying in the air, 2.7 g of (S)—N-[4-(3-amino-propoxy)-phenyl]-3-(2-(3-(guanidino)-benzoylamino)-acetylamino)-succinamic acid was isolated as a trifluoroacetate salt (85% yield). ES(+)-HRMS rule calcd. for $C_{23}H_{29}N_7O_6$ $(M+H)^+$ 500.2252, obsd., 500.2252.

General Method:

Step 10: Preparation of (S)—N-[4-[3-[[3-[2-[2-[2-[2-[2-[2-[2-[2-[3-(2,5-dioxo-2,5-dihydro-pyrrol-1-yl)-propionylamino]ethoxy]ethoxy]ethoxy]ethoxy]ethoxy]ethoxy]ethoxy]ethoxy]-1-oxopropyl]amino]propoxy]-phenyl]-3-[2-[3-[guanidino]-benzoylamino]-acetylamino]-succinamic acid

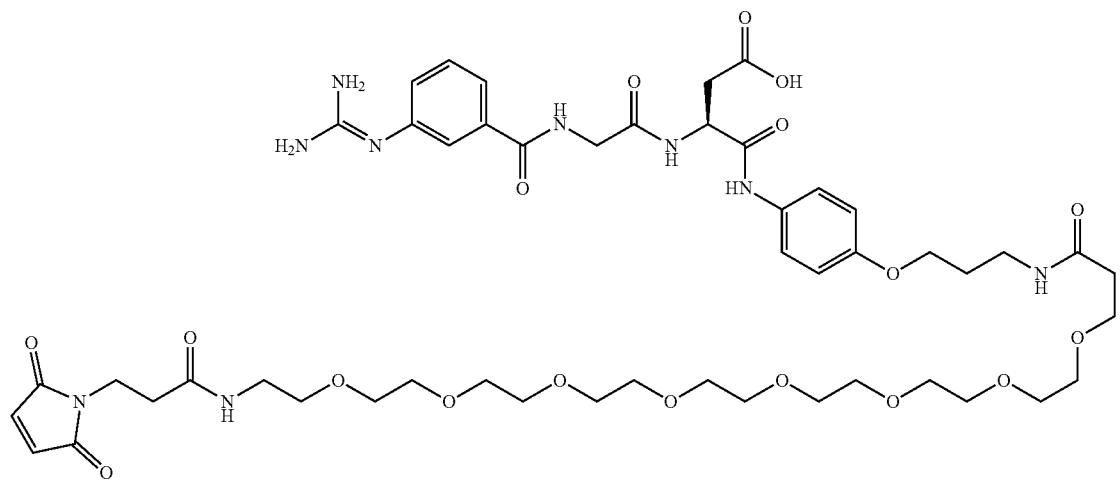 [SMILES: NC(N)=Nc1cccc(C(=O)NCC(=O)N[C@@H](CC(=O)O)C(=O)Nc2ccc(OCCCNC(=O)CCOCCOCCOCCOCCOCCOCCOCCOCCNC(=O)CCN3C(=O)C=CC3=O)cc2)c1]

To a solution of (S)—N-[4-(3-amino-propoxy)-phenyl]-3-(2-(3-(guanidino)-benzoylamino)-acetylamino)-succinamic acid (245 mg, 0.289 mmol) and 3-[2-[2-[2-[2-[2-[2-[2-[3-(2,5-dioxo-2,5-dihydro-pyrrol-1-yl)-propionylamino]-ethoxy]ethoxy]ethoxy]ethoxy]ethoxy]ethoxy]ethoxy]-propionic acid-2,5-dioxo-pyrrolidin-1-yl ester (200 mg, 0.289 mmol) in DMSO (5 mL) was added an excess of DIPEA (186 mg, 252 uL, 1.44 mmol) at room temperature under nitrogen atmosphere. The resulting light yellow solution was stirred for 2 h at which time LCMS analysis indicated the absence of starting material. Then, the excess DIPEA was removed under vacuum and the desired product was isolated by purification using HPLC method to obtain 212 mg of (S)—N-[4-[3-[3-[2-[2-[2-[2-[2-[2-[2-[3-(2,5-dioxo-2,5-dihydro-pyrrol-1-yl)-propionylamino]ethoxy]ethoxy]ethoxy]ethoxy]ethoxy]ethoxy]ethoxy]-1-oxopropyl]amino]propoxy]-phenyl]-3-[2-[3-[guanidino]-benzoylamino]-acetylamino]-succinamic acid (68% yield) as a light yellow solid. ES(+)-HRMS m/e calcd. for $C_{49}H_{71}N_9O_{18}$ (M+H)$^+$ 1074.4990, obsd. 1074.4984.

αvβ3 Ligand 2:

Preparation of (S)—N-[4-[3-[3-[2-[2-[2-[2-[2-[2-[2-[2-[2-[2-[2-[3-(2,5-dioxo-2,5-dihydro-pyrrol-1-yl)-propionylamino]ethoxy]ethoxy]ethoxy]ethoxy]ethoxy]ethoxy]ethoxy]ethoxy]ethoxy]ethoxy]ethoxy]-1-oxopropyl]amino]propoxy]-phenyl]-3-[2-[3-[guanidino]-benzoylamino]-acetylamino]-succinamic acid

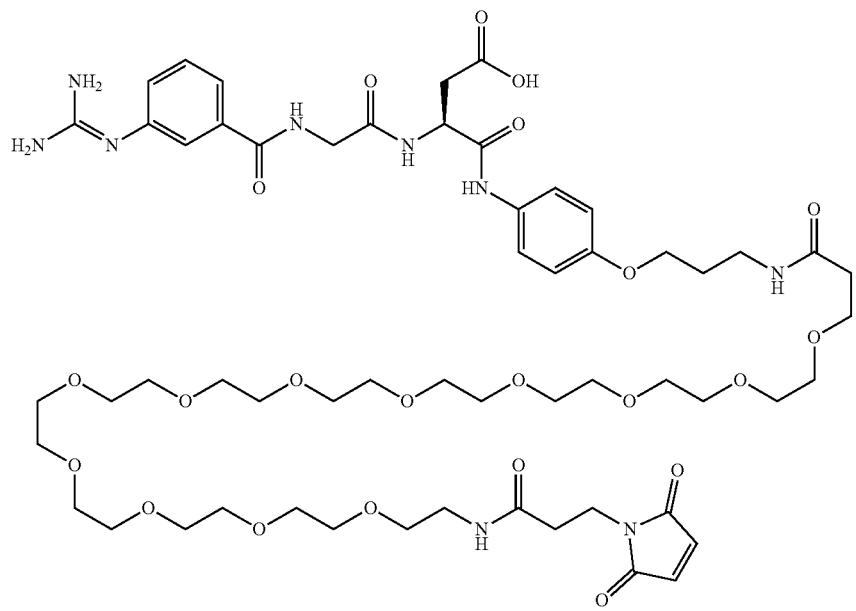 [SMILES: NC(N)=Nc1cccc(C(=O)NCC(=O)N[C@@H](CC(=O)O)C(=O)Nc2ccc(OCCCNC(=O)CCOCCOCCOCCOCCOCCOCCOCCOCCOCCOCCOCCOCCNC(=O)CCN3C(=O)C=CC3=O)cc2)c1]

A similar procedure as described in General method, Step 10 of αvβ3 ligand 1 was used, starting from (S)—N-[4-(3-amino-propoxy)-phenyl]-3-(2-(3-(guanidino)-benzoylamino)-acetylamino)-succinamic acid (245 mg, 0.289 mmol), 3-[2-[2-[2-[2-[2-[2-[2-[2-[2-[2-[2-[3-(2,5-dioxo-2,5-dihydro-pyrrol-1-yl)-propionylamino]-ethoxy]ethoxy]ethoxy]ethoxy]ethoxy]ethoxy]ethoxy]ethoxy]-propionic acid-2,5-dioxo-pyrrolidin-1-yl ester (250 mg, 0.289 mmol), and DIPEA (373 mg, 503 uL, 2.89 mmol) to obtain, after HPLC purification, 312 mg (86% yield) of (S)—N-[4-[3-[3-[2-[2-[2-[2-[2-[2-[2-[2-[2-[2-[2-[3-(2,5-dioxo-2,5-dihydro-pyrrol-1-yl)-propionylamino]ethoxy]ethoxy]ethoxy]ethoxy]ethoxy]ethoxy]ethoxy]ethoxy]ethoxy]ethoxy]-1-oxopropyl]amino]propoxy]-phenyl]-3-[2-[3-[guanidino]-benzoylamino]-acetylamino]-succinamic acid as a light brown oil. ES(+)-HRMS m/e calcd. for $C_{57}H_{87}N_9O_{22}$ (M+H)$^+$ 1250.6039, obsd. 1250.6032.

αvβ3 Ligand 3:

Preparation of (S)—N-[4-[3-[3-[2-[2-[2-[2-[2-[2-[2-[2-[2-[2-[2-[3-(2,5-dioxo-2,5-dihydro-1-yl)-propionylamino]ethoxy]ethoxy]ethoxy]ethoxy]ethoxy]ethoxy]ethoxy]ethoxy]ethoxy]ethoxy]-1-oxopropyl]amino]ethoxy]-phenyl]-3-[2-[3-[guanidino]-benzoylamino]-acetylamino]-succinamic acid Step 1: Preparation of [2-(4-nitro-phenoxy)-ethyl]-carbamic acid tert-butyl ester

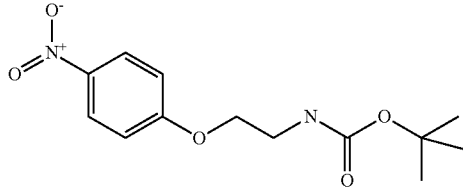 [SMILES: CC(C)(C)OC(=O)NCCOc1ccc([N+](=O)[O-])cc1]

2-(4-Nitro-phenoxy)-ethyl]-carbamic acid tert-butyl ester was prepared by a similar procedure as 2-(4-nitro-phenoxy)-propyl]-carbamic acid tert-butyl ester from (2-hydroxy-ethyl)-carbamic acid tert-butyl ester and 4-nitrophenol.

Step 2: Preparation of [2-(4-amino-phenoxy)-ethyl]-carbamic acid tert-butyl ester

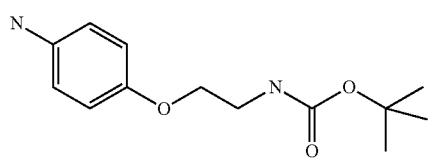 [SMILES: CC(C)(C)OC(=O)NCCOc1ccc(N)cc1]

2-(4-Amino-phenoxy)-ethyl]-carbamic acid tert-butyl ester was prepared by a similar procedure as 2-(4-amino-phenoxy)-propyl]-carbamic acid tert-butyl ester from 2-(4-nitro-phenoxy)-ethyl]-carbamic acid tert-butyl ester.

Step 3: Preparation of (S)—N-[4-(2-tert-butoxycarbonylamino-ethoxy)-phenyl]-3-(9H-fluoren-9-yl-methoxycarbonylamino)-succinamic acid tert-butyl ester

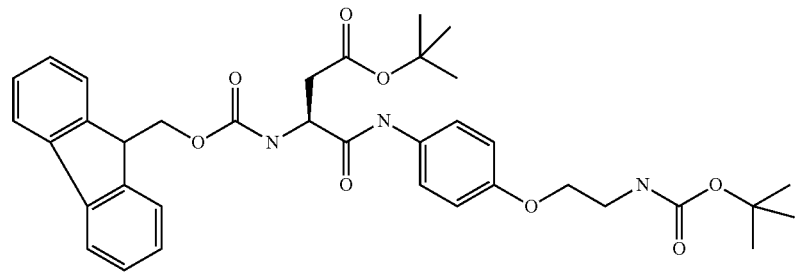 [SMILES: CC(C)(C)OC(=O)C[C@H](NC(=O)OCC1c2ccccc2-c2ccccc21)C(=O)Nc1ccc(OCCNC(=O)OC(C)(C)C)cc1]

(S)—N-[4-(2-tert-Butoxycarbonylamino-ethoxy)-phenyl]-3-(9H-fluoren-9-ylmethoxycarbonylamino)-succinamic acid tert-butyl ester was prepared by a similar procedure as of (S)—N-[4-(3-tert-butoxycarbonylamino-propoxy)-phenyl]-3-(9H-fluoren-9-ylmethoxycarbonylamino)-succinamic acid tert-butyl ester from [3-(4-amino-phenoxy)-ethyl]-carbamic acid tert-butyl ester and (S)-2-(9H-fluoren-9-ylmethoxycarbonylamino)-succinic acid tert-butyl ester.

Step 4: Preparation of (S)-3-amino-N-[4-(2-tert-butoxycarbonylamino-ethoxy)phenyl]succinamic acid tert-butyl ester

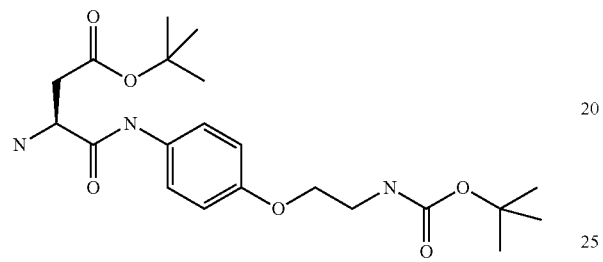

(S)-3-Amino-N-[4-(2-tert-butoxycarbonylamino-ethoxy)phenyl]succinamic acid tert-butyl ester was prepare by a similar procedure as (S)-3-amino-N-[4-(3-tert-butoxycarbonylamino-propoxy)-phenyl]-succinamic acid tert-butyl ester from (S)—N-[4-(3-tert-butoxycarbonylamino-ethoxy)-phenyl]-3-(9H-fluoren-9-ylmethoxycarbonylamino)-succinamic acid tert-butyl ester.

Step 5: Preparation of (S)-tert-butyl 4-(4-(2-(tert-butoxycarbonylamino)ethoxy)phenylamino)-4-oxo-3-(2-(3-(2,2,10,10-tetramethyl-4,8-dioxo-3,9-dioxo-5,7-diazaundecan-6-ylideneamino)benzamido)acetamido)butanoate

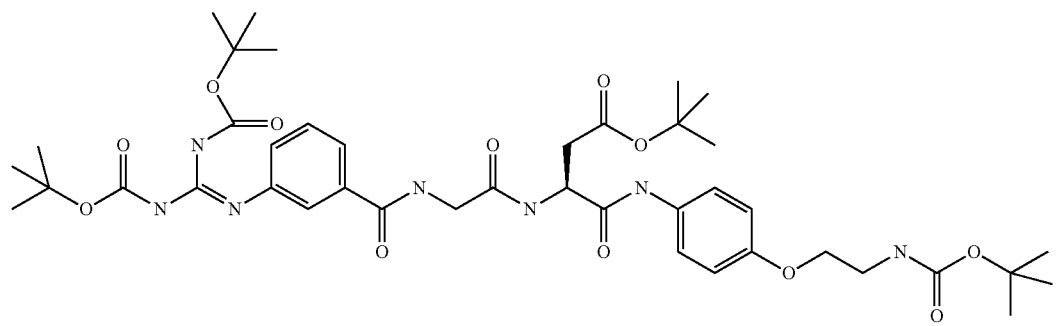 [SMILES: CC(C)(C)OC(=O)C[C@H](NC(=O)CNC(=O)c1cccc(N=C(NC(=O)OC(C)(C)C)NC(=O)OC(C)(C)C)c1)C(=O)Nc1ccc(OCCNC(=O)OC(C)(C)C)cc1]

(S)-tert-Butyl 4-(4-(2-(tert-butoxycarbonylamino)ethoxy)phenylamino)-4-oxo-3-(2-(3-(2,2,10,10-tetramethyl-4,8-dioxo-3,9-dioxo-5,7-diazaundecan-6-ylideneamino)benzamido)acetamido)butanoate was prepared by a similar procedure as (S)-3-(2-(3-(N,N-bis-tert-butoxycarbonylguanidino)-benzoylamino)-acetylamino)-N-[4-(3-tert-butoxycarbonylamino-propoxy)-phenyl]-succinamic acid tert-butyl ester from 2-(3-(2,2,10,10-tetramethyl-4,8-dioxo-3,9-dioxo-5,7-diazaundecan-6-ylideneamino)benzamido)acetic acid and (S)-tert-butyl 3-amino-4-(4-(2-(tert-butoxycarbonylamino)ethoxy)phenylamino)-4-oxobutanoate as a white light yellow solid, 3.57 g (97% yield).

Step 6: Preparation of (S)—N-[4-(2-amino-ethoxy)-phenyl]-3-[2-(3-guanidino-benzoylamino)-acetylamino]-succinamic acid trifluoroacetate salt

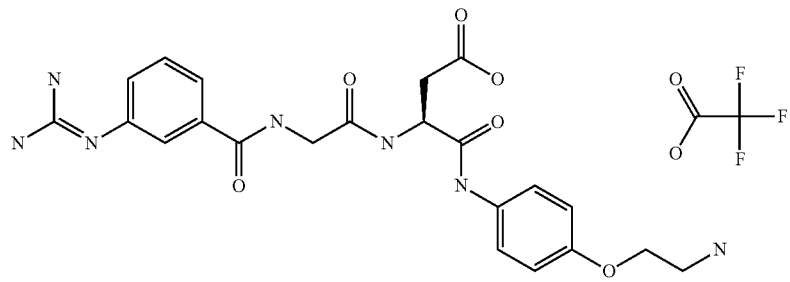 [SMILES: NCCOc1ccc(NC(=O)[C@H](CC(=O)O)NC(=O)CNC(=O)c2cccc(N=C(N)N)c2)cc1 ; O=C(O)C(F)(F)F]

((S)—N-[4-(2-Amino-ethoxy)-phenyl]-3-[2-(3-guanidino-benzoylamino)-acetylamino]-succinamic acid trifluoroacetate salt was prepared by a similar procedure as (S)—N-[4-(3-amino-propoxy)-phenyl]-3-(2-(3-(guanidino)-benzoylamino)-acetylamino)-succinamic acid trifluoroacetate salt from (S)-tert-butyl 4-(4-(2-(tert-butoxycarbonylamino)ethoxy)phenylamino)-4-oxo-3-(2-(3-(2,2,10,10-tetramethyl-4,8-dioxo-3,9-dioxo-5,7-diazaundecan-6-ylideneamino)benzamido)acetamido)butanoate as a HPLC purified lypholized white solid, 430 mg (51% yield), LCMS ES MS m/e calcd. for $C_{22}H_{27}N_7O_6$ $(M+H)^+$ 485.2 obsd. 486.1

Step 7: Preparation of (S)—N-[4-[3-[3-[2-[2-[2-[2-[2-[2-[2-[2-[2-[2-[2-[3-(2,5-dioxo-2,5-dihydro-pyrrol-1-yl)-propionylamino]ethoxy]ethoxy]ethoxy]ethoxy]ethoxy]ethoxy]ethoxy]ethoxy]ethoxy]ethoxy]ethoxy]-1-oxopropyl]amino]ethoxy]-phenyl]-3-[2-[3-[guanidino]-benzoylamino]-acetylamino]-succinamic acid

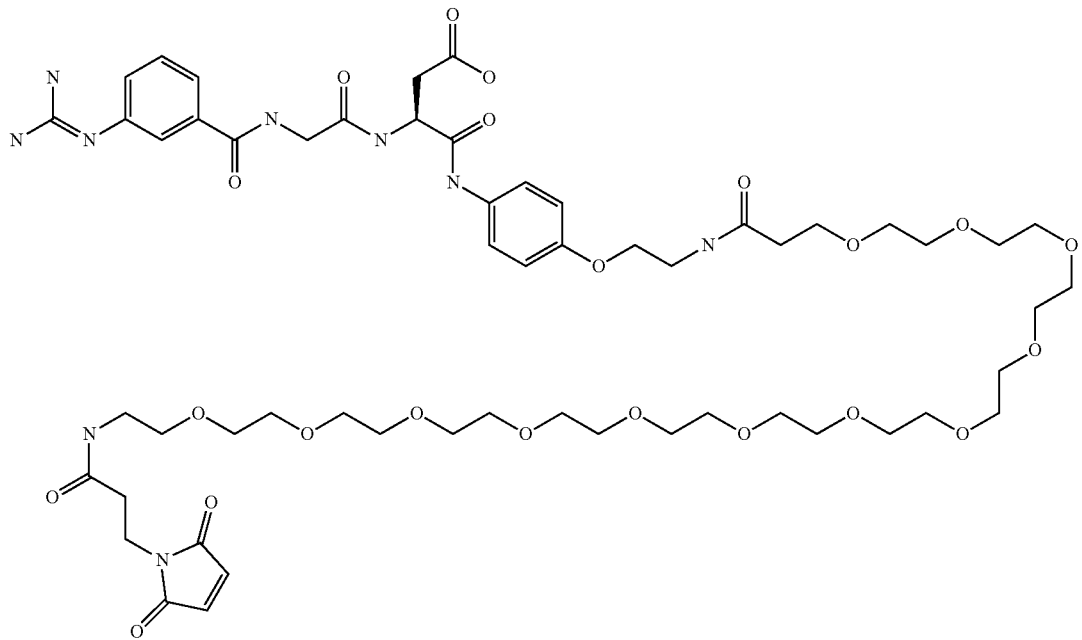 [SMILES: NC(N)=Nc1cccc(C(=O)NCC(=O)N[C@@H](CC(=O)O)C(=O)Nc2ccc(OCCNC(=O)CCOCCOCCOCCOCCOCCOCCOCCOCCOCCOCCOCCOCCNC(=O)CCN3C(=O)C=CC3=O)cc2)c1]

(S)—N-[4-[3-[3-[2-[2-[2-[2-[2-[2-[2-[2-[2-[2-[2-[3-(2,5-dioxo-2,5-dihydro-pyrrol-1-yl)-propionylamino]ethoxy]ethoxy]ethoxy]ethoxy]ethoxy]ethoxy]ethoxy]ethoxy]ethoxy]ethoxy]ethoxy]-1-oxopropyl]amino]ethoxy]-phenyl]-3-[2-[3-[guanidino]-benzoylamino]-acetylamino]-succinamic acid was prepared by a similar procedure as (S)—N-[4-[3-[[3-[2-[2-[2-[2-[2-[2-[2-[3-(2,5-dioxo-2,5-dihydro-pyrrol-1-yl)-propionylamino]ethoxy]ethoxy]ethoxy]ethoxy]ethoxy]ethoxy]ethoxy]-1-oxopropyl]amino]propoxy]-phenyl]-3-[2-[3-[guanidino]-benzoylamino]-acetylamino]-succinamic acid from (S)—N-[4-(2-amino-ethoxy)-phenyl]-3-[2-(3-guanidino-benzoylamino)-acetylamino]-succinamic acid trifluoroacetic acid salt and 3-[2-[2-[2-[2-[2-[2-[2-[2-[2-[2-[2-[3-(2,5-dioxo-2,5-dihydro-pyrrol-1-yl)-propionylamino]-ethoxy]ethoxy]ethoxy]ethoxy]ethoxy]ethoxy]ethoxy]-propionic acid-2,5-dioxo-pyrrolidin-1-yl ester as a clear, yellow tint viscous semisolid, 274 mg (73% yield). LCMS ESI MS m/e calcd. for $C_{56}H_{85}N_9O_{22}$ $(M+H)^+$ 1235.6, obsd. 1236.7.

VLA$_4$ Ligand 1:

(S)-3-[4-(2,6-dichlorobenzoylamino)phenyl]-2-[[[1-[2-[3-[2-[2-[2-[2-[2-[2-[2-[3-(2,5-dioxo-2,5-dihydropyrrol-1-yl)propionylamino]-ethoxy]ethoxy]ethoxy]ethoxy]ethoxy]ethoxy]ethoxy]ethoxy]propionylamino]ethyl]cyclopentyl]carbonyl]amino]propionic acid Step 1: Preparation of 1-(2-bromoethyl) cyclopentanecarboxylic acid methyl ester

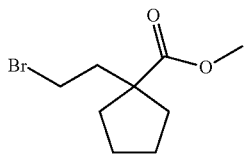

To a solution of diisopropylamine (396 mmol, 56 mL) in THF (85 mL) was added dropwise a solution of n-butyl lithium (393 mmol, 240 mL, 1.6M) in hexanes at −10° C. while maintaining the temperature below 0° C. After addition, the solution was stirred for 30 min at 0° C. To this, a solution of cyclopentanecarboxylic acid methyl ester (263 mmol, 37.4 g) in THF (50 mL) was added dropwise at −70° C. maintaining the internal temperature between −60 to −70° C. After addition, the reaction mixture was stirred for 1 h at −50 to −60° C. Then, a solution of 1,2-dibromoethane (545 mmol, 47 mL) in THF (50 mL) was added dropwise and the light brown suspension was stirred for 1 h at −70 to −60° C. Then, it was allowed to warm to room temperature and stirred overnight. The reaction mixture was poured into a saturated aqueous solution of ammonium chloride (200 mL) and the organic compound was extracted into ether (2×100 mL). The combined extracts were washed with a saturated solution of sodium chloride (150 mL) and dried over anhydrous magnesium sulfate. After filtration of the drying agent, the solution was concentrated under vacuum and the resulting residue was distilled at 95-105° C./2.5 mm Hg to obtain 49.6 g (80% yield) of 1-[2-bromoethyl]cyclopentanecarboxylic acid methyl ester as a colorless oil.

Step 2: Preparation of 1-[2-azidoethyl]cyclopentanecarboxylic acid methyl ester

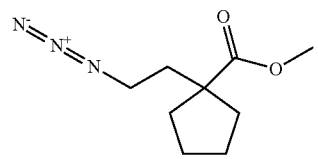

A solution of 1-[2-bromoethyl]cyclopentanecarboxylic acid methyl ester (211 mmol, 49.6 g) and sodium azide (831 mmol, 54 g) in DMF (200 mL) was stirred at 50° C. for 5 h under nitrogen atmosphere. Then, the solids were filtered and the filtrate was concentrated to near dryness. The residue was diluted with ethyl acetate (500 mL) and the undissolved solids were collected by filtration and the filtrate was concentrated to give the crude ethyl 1-(2-azidoethyl) cyclopentane carboxylate which was purified by chromatography over 250 g of silica gel, eluting with 5% ethyl acetate in hexane to give 36.2 g (87% yield) of 1-[2-azidoethyl]cyclopentanecarboxylic acid methyl ester as a light brown oil. EI(+)-HRMS m/c calcd. for $C_9H_{15}N_3O_2$ $(M-H)^+$ 196.1086, obsd. 196.1342.

Step 3: Preparation of 1-[2-azidoethyl cyclopentanecarboxylic acid

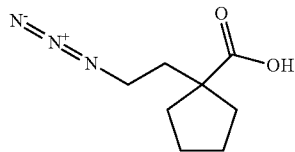 [SMILES: [N-]=[N+]=NCCC1(C(=O)O)CCCC1]

The 1-[2-azidoethyl]cyclopentanecarboxylic acid methyl ester (184 mmol, 36.2 g) was dissolved in THF (500 mL) and methanol (250 mL) and a solution of LiOH monohydrate (368 mmol, 15.44 g) in water (300 mL) was added. The resulting solution was stirred at 40° C. overnight and concentrated. The residue was dissolved in 1 L of water containing 40 mL of 1N NaOH and was washed with hexane (500 mL). The aqueous layer was acidified with 1N hydrochloric acid and the organic compound was extracted with ether (2×500 mL). The combined extracts were washed with saturated sodium chloride solution and the organic layer was dried over anhydrous $Na_2SO_4$. Filtration of the drying agent and concentration gave 32.5 g (96% yield) of 1-[2-azidoethyl cyclopentanecarboxylic acid as an amber liquid. ES(+)-HRMS m/e calcd. for $C_8H_{13}N_3O_2$ $(M+Na)^+$ 206.0900, obsd. 206.0900.

Step 4: Preparation of (S)-3-[4-nitrophenyl]-2-tert-butoxycarbonylamino-propionic acid methyl ester

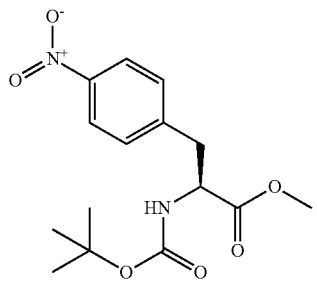 [SMILES: COC(=O)[C@H](Cc1ccc([N+](=O)[O-])cc1)NC(=O)OC(C)(C)C]

To a suspension of (S)-3-[4-nitrophenyl]-2-tert-butoxycarbonylamino-propionic acid (226.2 mmol, 70.2 g) and sodium carbonate (1.13 mol, 95 g) in DMF (500 mL) was added methyl iodide (1.13 mol, 70.4 mL) at room temperature. The suspension was stirred for 15 h at room temperature at which time TLC analysis of the mixture indicated the absence of starting material and the excess methyl iodide and some DMF were removed under high vacuum. Then, it was poured into water (2 L) and stirred at room temperature as a precipitate formed slowly over 72 h. The precipitated solids were collected by filtration and washed with water (2 L). After air and vacuum drying, 72 g (98% yield) of (S)-3-[4-nitrophenyl]-2-tert-butoxycarbonylamino-propionic acid methyl ester was isolated as a light yellow solid (mp 95-96° C.). ES(+)-HRMS calcd. for $C_{15}H_{20}N_2O_6$ (M+H)$^+$ 325.1400, obsd. 325.1404.

Step 5: Preparation of (S)-3-[4-aminophenyl]-2-tert-butoxycarbonylamino-propionic acid methyl ester

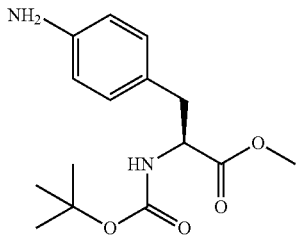 [SMILES: COC(=O)[C@H](Cc1ccc(N)cc1)NC(=O)OC(C)(C)C]

To a mixture of methyl (S)-3-[4-nitrophenyl]-2-tert-butoxycarbonylamino-propionic acid methyl ester (222 mmol, 72 g), zinc dust (~325 mesh, 2.2 mol, 145.2 g, 10 equiv.) and ammonium chloride (33 mol, 178.1 g, 15 equiv.) was added methanol (1 L) and water (500 L) at room temperature. After addition of water, an exothermic reaction ensued and the internal temperature rose to 45 to 50° C. The suspension was stirred for 30 min to 1 h at room temperature, at which time TLC analysis of the mixture indicated the absence of starting material, and the reaction mixture was filtered through a pad of celite and the filtered cake was washed with methanol (1 L) and water (500 mL). Concentration to remove most of the methanol and some water afforded white solids which were collected by filtration and washed with water. After air drying, 65.5 g (100% yield) of (S)-3-[4-aminophenyl]-2-tert-butoxycarbonylamino-propionic acid methyl ester was isolated as a white solid (mp 86-89° C.). ES(+)-HRMS m/e calcd. for $C_{15}H_{22}N_2O_4$ (M+H)$^+$ 294.1621, obsd. 294.1614.

Step 6: Preparation of (S)-2-tert-butoxycarbonylamino-3-[4-(2,6-dichlorobenzoylamino)phenyl]propionic acid methyl ester

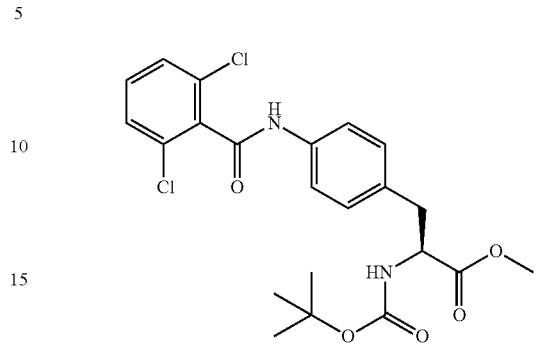

To a solution of (S)-3-[4-aminophenyl]-2-tert-butoxycarbonylamino-propionic acid methyl ester (127.6 mmol, 37.57 g) and 2,6-dichlorobenzoyl chloride (140.6 mmol, 29.45 g) in dichloromethane (350 mL) was added DIPEA (192 mmol, 24.8 g) at room temperature. The brown solution was stirred for 15 h at room temperature to afford a white suspension at this time TLC analysis of the mixture indicated the absence of starting material. Then, the solids were collected by filtration and the solids were washed with dichloromethane (150 mL) and air dried to obtain 52.75 g (88.4% yield) of (S)-2-tert-butoxycarbonylamino-3-[4-(2,6-dichlorobenzoylamino)phenyl]propionic acid methyl ester as a white solid: mp 192-194° C. ES(+)-HRMS rule calcd. for $C_{22}H_{24}Cl_2N_2O_5$ (M+H)$^+$ 466.1062, obsd. 466.1069.

Step 7: Preparation of (S)-2-amino-3-[4-(2,6-dichlorobenzoylamino)phenyl]propionic acid methyl ester hydrochloride salt

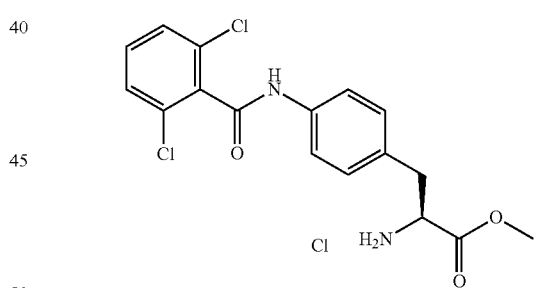

A suspension of (S)-2-tert-butoxycarbonylamino-3-[4-(2,6-dichlorobenzoylamino)phenyl]propionic acid methyl ester (92.97 mmol, 43.45 g) in dioxane (90 mL) was treated with 166 mL of 4.0N hydrochloric acid in dioxane at room temperature. After 5 minutes, the solids went into solution and the mixture was stirred for 2 h. Then, some of the dioxane was removed under vacuum to afford an yellow syrup and 250 mL of ethyl ether was added. A gum was formed which was dissolved in THF (100 mL) and methanol (100 mL). The solvent was removed under vacuum to obtain 43.7 g (100% yield) of (S)-2-amino-3-[4-(2,6-dichlorobenzoylamino)phenyl]propionic acid methyl ester hydrochloride salt as a white solid: mp 180-195° C. This was stored in the refrigerator under argon atmosphere. ES(+)-HRMS m/e calcd, for $C_{17}H_{16}Cl_2N_2O_3$ (M+H)$^+$ 367.0616, obsd, 367.0611.

Step 8: Preparation of (S)-2-[[1-(2-azidoethyl)cyclopentanecarbonyl]amino]3-[4-(2,6-dichlorobenzoylamino)phenyl]propionic acid methyl ester

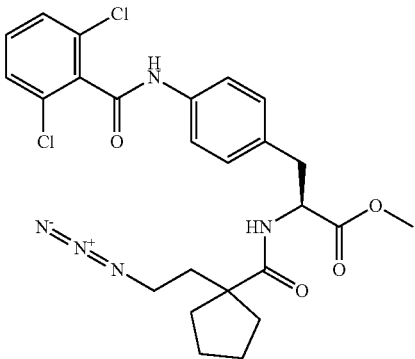 [SMILES: COC(=O)[C@H](Cc1ccc(NC(=O)c2c(Cl)cccc2Cl)cc1)NC(=O)C1(CCN=[N+]=[N-])CCCC1]

To a solution of (S)-2-amino-3-[4-(2,6-dichlorobenzoylamino)phenyl]propionic acid methyl ester hydrochloride salt (24.79 mmol, 10 g) and 1-[2-azidoethyl]cyclopentanecarboxylic acid methyl ester (27.29 mmol, 5 g) in DMF (100 mL) were added HBTU (27.33 mmol, 10.37 g) and DIPEA (68.3 mmol, 8.82 g) at room temperature. The clear solution was stirred for 48 h at room temperature and water was added (~200 mL) to the reaction mixture to precipitate the product. The solid was collected by filtration and washed with water (100 mL) and hexane (~100 mL). After drying at air, 11.2 g of the product was obtained as a light brick solid which was treated with acetonitrile (100 mL) at hot condition. All impurities went into acetonitrile and the solid was collected by filtration to afford 8.24 g of coupling product. The acetonitrile solution was removed under vacuum and the residue was dissolved in ethyl acetate and the product was precipitated by the addition of hexane. Again, the solid was collected by filtration and the solids were dried at air to obtain another 2.03 g (78% total yield) of (S)-2-[[1-(2-azidoethyl)cyclopentanecarbonyl]amino]3-[4-(2,6-dichlorobenzoylamino)phenyl]propionic acid methyl ester as a white solid. ES(+)-HRMS rule calcd. for $C_{25}H_{27}Cl_2N_5O_4$ $(M+Na)^+$ 554.1332, obsd. 554.1334.

Step 9: Preparation of (S)-2-[[1-(2-azidoethyl)cyclopentanecarbonyl]amino]3-[4-(2,6-dichlorobenzoylamino)phenyl]propionic acid

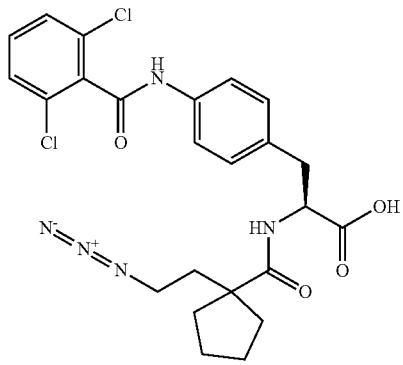 [SMILES: [N-]=[N+]=NCCC1(C(=O)N[C@@H](Cc2ccc(NC(=O)c3c(Cl)cccc3Cl)cc2)C(=O)O)CCCC1]

To a suspension of (S)-2-[[1-(2-azidoethyl)cyclopentanecarbonyl]amino]3-[4-(2,6-dichlorobenzoylamino)phenyl]propionic acid methyl ester (27.7 mmol, 14.77 g) THF (200 mL) and ethanol (200 mL) was added aqueous 1.0N sodium hydroxide (150 mL) at room temperature. The mixture was stirred for 15 h at room temperature at which time TLC analysis of the mixture indicated the absence of starting material. Then, it was diluted with water (20 mL) and the THF and ethanol was removed by rotary evaporation and diluted with 100 mL of water and extracted with ether (200 mL) to remove any neutral impurities. The aqueous layer was neutralized with 1N HCl and the resulting white solids were collected by filtration and washed with water and hexanes. After air-drying, 13.37 g (93% yield) of (S)-2-[[1-(2-azidoethyl)cyclopentanecarbonyl]amino]3-[4-(2,6-dichlorobenzoylamino)phenyl]propionic acid was obtained as a white solid. ES(+)-HRMS m/e calcd. for $C_{24}H_{25}Cl_2N_5O_4$ $(M+Na)^+$ 540.1176, obsd. 540.1177.

Step 10: Preparation of (S)-2-[[1-(2-aminoethyl)cyclopentanecarbonyl]amino]3-[4-(2,6-dichlorobenzoylamino)phenyl]propionic acid

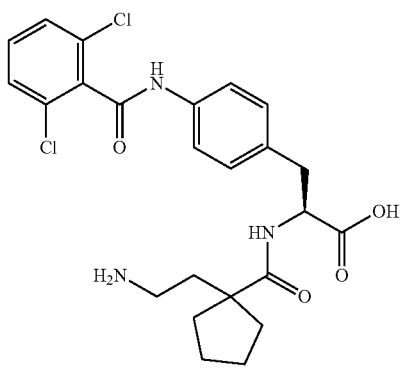 [SMILES: NCCC1(C(=O)N[C@@H](Cc2ccc(NC(=O)c3c(Cl)cccc3Cl)cc2)C(=O)O)CCCC1]

To a solution of (S)-2-[[1-(2-azidoethyl)cyclopentanecarbonyl]amino]3-[4-(2,6-dichlorobenzoylamino)phenyl]propionic acid (12.11 mmol, 6.28 g) in THF (91 mL) was added a solution of trimethylphosphine in THF (48.46 mmol, 48.5 mL, 1.0M) at 0° C. It was a clear solution in the beginning and after 30 min some precipitate was formed and this mixture was stirred for overnight at which time TLC analysis of the mixture indicated the absence of starting material.

Then, 10 equiv. of water (120 mmol, 2.16 mL) was added and the mixture was stirred for 2 h at room temperature. The solvent was removed under vacuum and the residue was azeotrophed two times with toluene to give a pasty material which was purified using HPLC method to obtain 4.57 g (77% yield) of (S)-2-[[1-(2-aminoethyl)cyclopentanecarbonyl]amino]3-[4-(2,6-dichlorobenzoylamino)phenyl]propionic acid as an amorphous white solid. ES(+)-HRMS m/e calcd. for $C_{24}H_{27}Cl_2N_3O_4$ $(M+H)^+$ 492.1452, obsd, 492.1451.

Step 11: Preparation of (S)-3-[4-(2,6-dichlorobenzoylamino)phenyl]-2-[[[1-[2-[3-[2-[2-[2-[2-[2-[2-[2-[3-(2,5-dioxo-2,5-dihydropyrrol-1-yl)propionylamino]-ethoxy]ethoxy]ethoxy]ethoxy]ethoxy]ethoxy]ethoxy]ethoxy]propionylamino]ethyl]cyclopentyl]carbonyl]amino]propionic acid

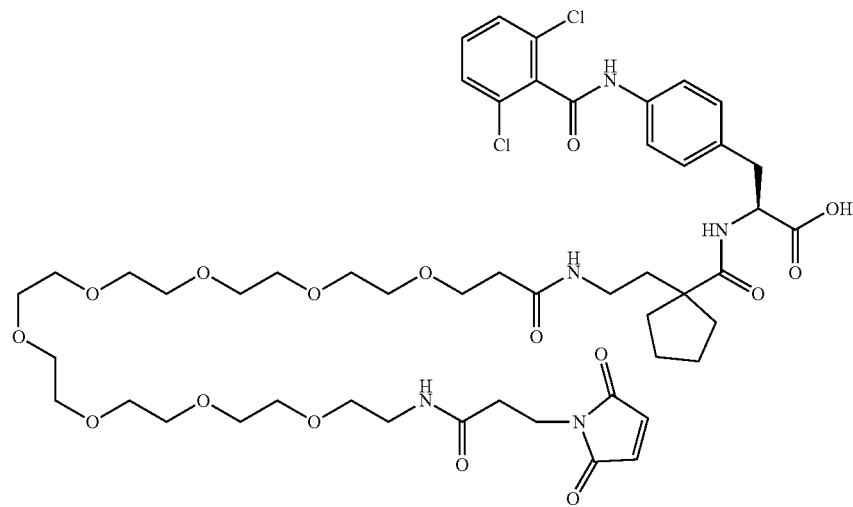 [SMILES: O=C(CCOCCOCCOCCOCCOCCOCCOCCOCCNC(=O)CCN1C(=O)C=CC1=O)NCCC1(C(=O)N[C@@H](Cc2ccc(NC(=O)c3c(Cl)cccc3Cl)cc2)C(=O)O)CCCC1]

A similar procedure as described in General method, Step 10 of αvβ3 ligand 1 was used, starting from (S)-2-[[1-(2-aminoethyl)cyclopentanecarbonyl]amino]-3-[4-(2,6-dichlorobenzoylamino)phenyl]propionic acid (607 mg, 1.0 mmol), 3-[2-[2-[2-[2-[2-[2-[2-[2-[3-(2,5-dioxo-2,5-dihydro-pyrrol-1-yl)-propionylamino]-ethoxy]ethoxy]ethoxy]ethoxy]ethoxy]ethoxy]ethoxy]-propionic acid-2,5-dioxo-pyrrolidin-1-yl ester (689 mg, 1.0 mmol), and DIPEA (388 mg, 522 uL, 3.0 mmol) to obtain, after HPLC purification, 788 mg (74% yield) of (S)-3-[4-(2,6-dichlorobenzoylamino)phenyl]-2-[[1-[2-[3-[2-[2-[2-[2-[2-[2-[2-[3-(2,5-dioxo-2,5-dihydropyrrol-1-yl)propionylamino]-ethoxy]ethoxy]ethoxy]ethoxy]ethoxy]ethoxy]ethoxy]ethoxy]propionylamino]ethyl]cyclopentane carbonyl]amino]propionic acid as a light yellow solid. ES(+)-HRMS m/e calcd. for $C_{50}H_{69}N_5O_{16}Cl_2$ (M+H)+ 1066.4189, obsd. 1066.4182.

VLA$_4$ Ligand 2 tert-butyl ester:

N-[2-[2-[2-[2-[2-[2-[2-[2-[2-[2-[2-[2-[2-[2-[2-[2-[2-[2-[2-[2-[2-[2-[2-[1-(S)-1-tert-butoxycarbonyl-2-[4-(2,6-dichlorobenzoylamino)phenyl]ethylcarbamoyl]cyclopentyl]ethylcarbamoyl]ethoxy]ethoxy]ethoxy]ethoxy]ethoxy]ethoxy]ethoxy]ethoxy]ethoxy]ethoxy]ethoxy]ethoxy]ethoxy]ethoxy]ethoxy]ethoxy]ethoxy]ethoxy]ethoxy]ethoxy]ethoxy]ethyl]succinamic acid 2,5-dioxo-3-sulfo-pyrrolidin-1-yl ester sodium salt Step 1: Preparation of (S)-2-[[1-(2-azido-ethyl)-cyclopentanecarbonyl]-amino]-3-[4-(2,6-dichloro-benzoylamino)-phenyl]-propionic acid tert-butyl ester

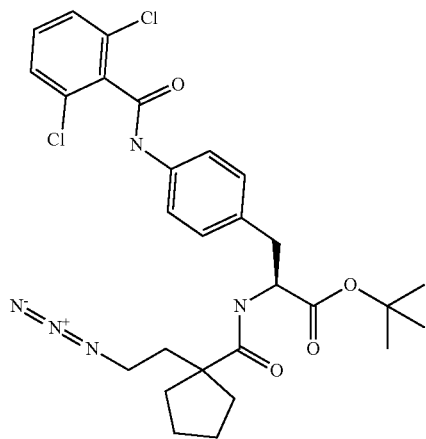 [SMILES: CC(C)(C)OC(=O)[C@H](Cc1ccc(NC(=O)c2c(Cl)cccc2Cl)cc1)NC(=O)C1(CCN=[N+]=[N-])CCCC1]

In a 500 mL round-bottomed flask, (S)-2-(1-(2-azido-ethyl)cyclopentanecarboxamido)-3-(4-(2,6-dichlorobenzamido)phenyl)propanoic acid (6.216 g, 12.0 mmol, Eq: 1.00) was combined with DCM (120 mL) to give a white suspension and the reaction mixture was cooled in an ice bath under nitrogen. Trifluoroacetic anhydride (5.04 g, 24.0 mmol, Eq: 2) dissolved in 10 mL of DCM was added portion wise to the reaction. During addition, the solution cleared and had a yellow tint and it was stirred in the ice bath for 2 h and then tert-butanol (8.89 g, 120 mmol, Eq: 10) was added portion wise. After 1 h, the reaction was removed from the ice bath and allow to warm to room temperature overnight. The reaction was refluxed for 1 h and then concentrated forming a white solid. The solid was partitioned between a saturated aqueous sodium bicarbonate solution (100 mL) and ethyl acetate (200 mL), organic phase separated and washed with water (100 mL) and brine (150 mL). The aqueous layer was extracted with ethyl acetate (100 mL) and washed with the same water and brine. The organic layers were combined, dried over magnesium sulfate, concentrated, and dried under high vacuum. The crude product was purified by SFC, affording (S)-2-{[1-(2-azido-ethyl)-cyclopentanecarbonyl]-amino}-3-[4-(2,6-dichloro-benzoylamino)-phenyl]-propionic acid tert-butyl ester as a white solid (1.94 g, 28.1% yield) with the same optical rotation as the starting material. ES(+)-LRMS m/e calcd. for $C_{24}H_{25}N_5O_4Cl_2$ (M+H)+ 517.1, obsd. 518.

Step 2: Preparation of (S)-2-{[1-(2-amino-ethyl)-cyclopentanecarbonyl]-amino}-3-[4-(2,6-dichloro-benzoylamino)-phenyl]-propionic acid tert-butyl ester

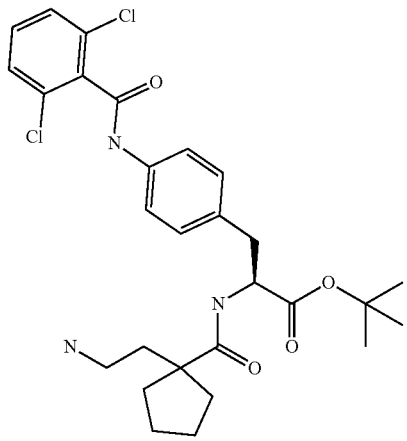 [SMILES: CC(C)(C)OC(=O)[C@H](Cc1ccc(NC(=O)c2c(Cl)cccc2Cl)cc1)NC(=O)C1(CCN)CCCC1]

To a solution of (S)-2-{[1-(2-azido-ethyl)-cyclopentanecarbonyl]-amino}-3-[4-(2,6-dichloro-benzoylamino)-phenyl]-propionic acid (1.9 g, 3.31 mmol, Eq: 1) in 1 L round bottom flask was added THF (40 mL), stirred under nitrogen, and then trimethyl phosphine (16.5 mL, 16.5 mmol, 1 M, THF, Eq: 5) was added. The resulting clear solution was stirred at room temperature for 21 h under nitrogen atmosphere. The reaction mixture was concentrated dried from DCM/Hexanes, partitioned between acetonitrile (50 mL) and water (50 mL) and stirred at room temperature for 22 h. The reaction mixture was then concentrated, partitioned between ethyl acetate (175 mL) and saturated aqueous sodium bicarbonate solution (200 mL) and organic phase separated. The aqueous phase was extracted with EA (100 mL). The organic layers were washed with brine (75 mL), combined, dried over magnesium sulfate, filtered, concentrated, and dried from DCM/Hexanes and then DCM to afford (S)-2-{[1-(2-amino-ethyl)-cyclopentanecarbonyl]-amino}-3-[4-(2,6-dichloro-benzoylamino)-phenyl]-propionic acid tert-butyl ester as a yellow solid (1.67 g, 92% yield). ES(+)-LRMS m/e calcd. for $C_{24}H_{27}N_3O_4Cl_2$ (M+H)+ 491.1, obsd. 492.

Step 3: Preparation of (S)-3-[4-(2,6-dichlorobenzoylamino)phenyl]-2-[[1-[2-[3-[2-[2-[2-[2-[2-[2-[2-[2-[2-[2-[2-[2-[2-[2-[2-[2-[2-[2-[9H- fluoen-9-ylmethoxycarbonylamino]ethoxy]ethoxy]ethoxy]ethoxy]ethoxy]ethoxy]ethoxy]ethoxy]ethoxy]ethoxy]ethoxy]ethoxy]ethoxy]ethoxy]ethoxy]ethoxy]ethoxy]ethoxy]ethoxy]propionylamino]ethyl]cyclopentanecarbonyl]amino] propionic acid tert-butyl ester

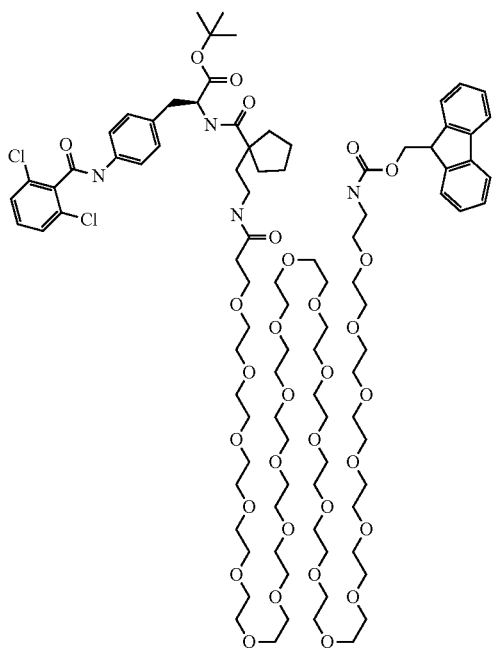 [SMILES: CC(C)(C)OC(=O)[C@H](Cc1ccc(NC(=O)c2c(Cl)cccc2Cl)cc1)NC(=O)C1(CCNC(=O)CCOCCOCCOCCOCCOCCOCCOCCOCCOCCOCCOCCOCCOCCOCCOCCOCCOCCOCCOCCOCCOCCOCCOCCOCCNC(=O)OCC2c3ccccc3-c3ccccc32)CCCC1]

To a 50 ml round bottom flask containing 3-[2-[2-[2-[2-[2-[2-[2-[2-[2-[2-[2-[2-[2-[2-[2-[2-[2-[2-[2-[2-[9H-fluoen-9-ylmethoxycarbonylamino]ethoxy]ethoxy]ethoxy]ethoxy]ethoxy]ethoxy]ethoxy]ethoxy]ethoxy]ethoxy]ethoxy]ethoxy]ethoxy]ethoxy]ethoxy]ethoxy]ethoxy]ethoxy]ethoxy]propionic acid (305 mg, 223 µmol, Eq: 1.0) was added ((S)-2-{[1-(2-amino-ethyl)-cyclopentanecarbonyl]-amino}-3-[4-(2,6-dichloro-benzoylamino)-phenyl]-propionic acid tert-butyl ester (134 mg, 245 µmol Eq: 1.1), acetonitrile (2 mL) and DIEA (86.4 mg, 117 µL, 669 µmol, Eq: 3). The yellow solution was stirred for 5 min at room temperature and then HBTU (127 mg, 334 µmol, Eq: 1.5) was added. The reaction's atmosphere was purged with nitrogen, the flask sealed, and stirred at room temperature for 2.8 days. The reaction was worked up by addition of TFA (50 µL) passed through a 0.2 µm PVDF syringe filter (w/1× rinse 1 mL) and then purified by RP-HPLC (C18 Pursuit, 20×150 mm, 30 mL/min, water/acetonitrile with 0.1% TFA, 35 to 100% acetonitrile over 8 min, and three injections). The appropriate fractions of were combined, 0.5 g of diisopropylamine resin (Aldrich 538736-25 g) was added, and the mixture was stirred for 3 h at room temperature. The material was filtered through a #1 Whatman filter paper and the filtrate concentrated, dried from acetonitrile, and dried on high vacuum affording (S)-3-[4-(2,6-dichlorobenzoylamino)phenyl]-2-[[1-[2-[3-[2-[2-[2-[2-[2-[2-[2-[2-[2-[2-[2-[2-[2-[2-[2-[2-[9H-fluoen-9-ylmethoxycarbonylamino]ethoxy]ethoxy]ethoxy]ethoxy]ethoxy]ethoxy]ethoxy]ethoxy]ethoxy]ethoxy]ethoxy]ethoxy]ethoxy]ethoxy]ethoxy]ethoxy]ethoxy]ethoxy]ethoxy]propionylamino]ethyl]cyclopentanecarbonyl]amino] propionic acid tert-butyl
ester (264 mg, 62% yield) as a colorless viscous oil. ES(+)-LRMS m/e calcd. for $C_{94}H_{146}N_4O_{31}Cl_2$ $(M+H)^+$ 1899, obsd. 950 $((M+H)/2)^+$.

Step 4: Preparation of (S)-2-[[1-[2-[3-[2-[2-[2-[2-[2-[2-[2-[2-[2-[2-[2-[2-[2-[2-[2-[2-[2-[2-[aminoethoxy]ethoxy]ethoxy]ethoxy]ethoxy]ethoxy]ethoxy]ethoxy]ethoxy]ethoxy]ethoxy]ethoxy]ethoxy]ethoxy]ethoxy]ethoxy]ethoxy]ethoxy]ethoxy]ethoxy]propionylamino]ethyl]cyclopentanecarbonyl]amino]-3-[4-(2,6-dichlorobenzoylamino)phenyl]-propionic acid tert-butyl ester

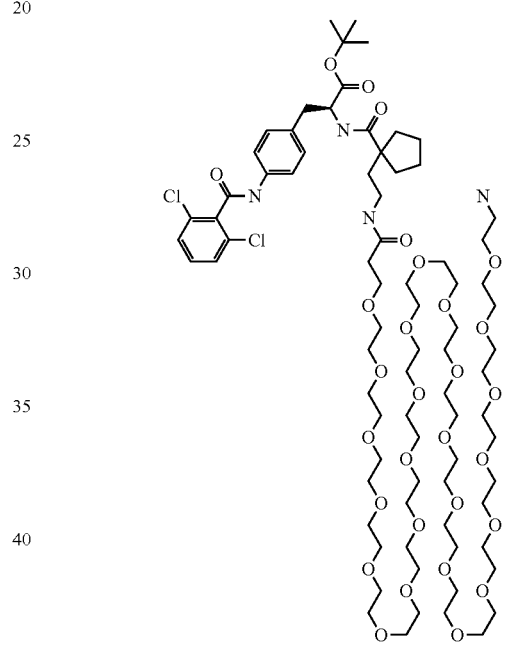

To a 25 ml round bottom flask containing (S)-3-[4-(2,6-dichlorobenzoylamino)phenyl]-2-[[1-[2-[3-[2-[2-[2-[2-[2-[2-[2-[2-[2-[2-[2-[2-[2-[2-[2-[2-[2-[2-[9H-fluoen-9-ylmethoxycarbonylamino]ethoxy]ethoxy]ethoxy]ethoxy]ethoxy]ethoxy]ethoxy]ethoxy]ethoxy]ethoxy]ethoxy]ethoxy]ethoxy]ethoxy]ethoxy]ethoxy]ethoxy]ethoxy]ethoxy]propionylamino]ethyl]cyclopentanecarbonyl]amino]propionic acid tert-butyl ester (260 mg, 137 µmol, Eq: 1.00) was added DMF (2 mL) and nitrogen was bubbled into the solution. Nonane-1-thiol (219 mg, 261 µL, 1.37 mmol, Eq: 10), and then DBU (41.7 mg, 41.3 µL, 274 µmol, Eq: 2) were added, the flask wrapped in aluminum foil and the reaction was stirred at room temperature for 17 h. The reaction was filtered through a syringe filter (0.45 µm PTFE) with 2 rinsing of ACN 1 mL/each) and the sample was purified by RP-HPLC (C18 Pursuit, 20×150 mm, 30 mL/min, 3 injections, with different starting concentrations of the gradient 15, 20, and 30% to 100% ACN in water, 8 min, no modifier). Appropriate fractions combined, concentrate, dried from ACN affording (S)-2-[[1-[2-[3-[2-[2-[2-[2-[2-[2-[2-[2-[2-[2-[2-[2-[2-[2-[2-[2-[2-[2-[2-[2-[aminoethoxy]ethoxy]ethoxy]ethoxy]ethoxy]ethoxy]ethoxy]ethoxy]ethoxy]ethoxy]ethoxy]ethoxy]ethoxy]ethoxy]ethoxy]ethoxy]ethoxy]ethoxy]ethoxy]propionylamino]ethyl]cyclopentanecarbonyl]amino]-3-[4-(2,6-dichlorobenzoylamino)phenyl]-propionic acid tert-butyl ester as a colorless viscous oil (79 mg, 82% yield). ES(+)-LRMS m/e calcd. for $C_{79}H_{136}N_4O_{29}Cl_2$ (M+H)$^+$1677.9, obsd. 839 ((M+H)/2)+. Step 5: Preparation of N-[2-[2-[2-[2-[2-[2-[2-[2-[2-[2-[2-[2-[2-[2-[2-[2-[2- [2-[2-[2-[2-[2-[2-[1-[(S)-1-tert-butoxycarbonyl-2-[4-(2,6-dichlorobenzoylamino)phenyl]ethylcarbamoyl]cyclopentyl]ethylcarbamoyl]ethoxy]ethoxy]ethoxy]ethoxy]ethoxy]ethoxy]ethoxy]ethoxy]ethoxy]ethoxy]ethoxy]ethoxy]ethoxy]ethoxy]ethoxy]ethoxy]ethoxy]ethoxy]ethoxy]ethoxy]ethoxy]ethyl]succinamic acid

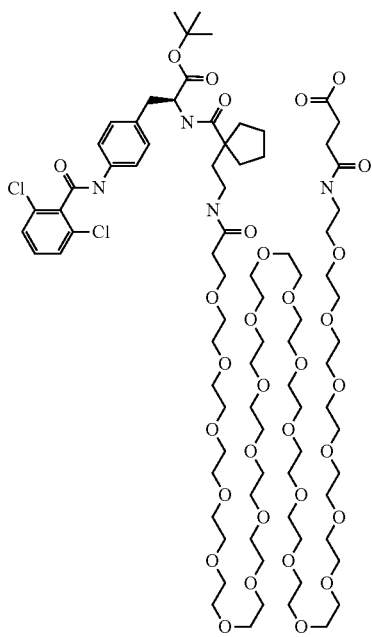 [SMILES: CC(C)(C)OC(=O)[C@H](Cc1ccc(NC(=O)c2c(Cl)cccc2Cl)cc1)NC(=O)C1(CCNC(=O)CCOCCOCCOCCOCCOCCOCCOCCOCCOCCOCCOCCOCCOCCOCCOCCOCCOCCOCCOCCOCCOCCOCCOCCOCCNC(=O)CCC(=O)O)CCCC1]

In a 25 mL pear shaped flask, (S)-2-[[1-[2-[3-[2-[2-[2-[2-[2-[2-[2-[2-[2-[2-[2-[2-[2-[2-[2-[2-[2-[2-[2-[2-[aminoethoxy]ethoxy]ethoxy]ethoxy]ethoxy]ethoxy]ethoxy]ethoxy]ethoxy]ethoxy]ethoxy]ethoxy]ethoxy]ethoxy]ethoxy]ethoxy]ethoxy]ethoxy]ethoxy]propionylamino]ethyl]cyclopentanecarbonyl]amino]-3-[4-(2,6-dichlorobenzoylamino)phenyl]-propionic acid tert-butyl ester (77 mg, 37.7 μmol, Eq: 1.00) was combined with DMSO (1 mL) to give a colorless solution. DIPEA (23.7 mg, 32 μL, 183 μmol, Eq: 4.87) and dihydrofuran-2,5-dione (succinic anhydride) (6 mg, 60.0 μmol, Eq: 1.59) were added and the reaction was stirred 15.5 h. The solution containing N-[2-[2-[2-[2-[2-[2-[2-[2-[2-[2-[2-[2-[2-[2-[2-[2-[2-[2-[1-[(S)-1-tert-butoxycarbonyl-2-[4-(2,6-dichlorobenzoylamino)phenyl]ethylcarbamoyl]cyclopentyl]ethylcarbamoyl]ethoxy]ethoxy]ethoxy]ethoxy]ethoxy]ethoxy]ethoxy]ethoxy]ethoxy]ethoxy]ethoxy]ethoxy]ethoxy]ethoxy]ethoxy]ethoxy]ethoxy]ethoxy]ethoxy]ethyl]succinamic acid was used in Step 6 without purification. ES(+)-LRMS m/e calcd. for $C_{83}H_{140}N_4O_{32}Cl_2$ (M+H)$^+$1777.0, obsd. 889 ((M+H)/2)$^+$.

Step 6: Preparation of N-[2-[2-[2-[2-[2-[2-[2-[2-[2-[2-[2-[2-[2-[2-[2-[2-[2-[2-[2-[2-[2-[2-[1-[(S)-1-tert-butoxycarbonyl-2-[4-(2,6-dichlorobenzoylamino)phenyl]ethylcarbamoyl]cyclopentyl]ethylcarbamoyl]ethoxy]ethoxy]ethoxy]ethoxy]ethoxy]ethoxy]ethoxy]ethoxy]ethoxy]ethoxy]ethoxy]ethoxy]ethoxy]ethoxy]ethoxy]ethoxy]ethoxy]ethoxy]ethoxy]ethoxy]ethyl]succinamic acid 2,5-dioxo-3-sulfo-pyrrolidin-1-yl ester sodium salt

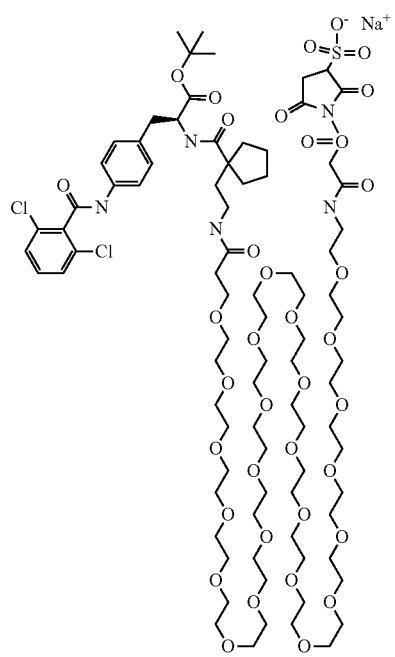

To a solution of N-[2-[2-[2-[2-[2-[2-[2-[2-[2-[2-[2-[2-[2-[2-[2-[2-[2-[2-[2-[2-[2-[2-[1-[(S)-1-tert-butoxycarbonyl-2-[4-(2,6-dichlorobenzoylamino)phenyl]ethylcarbamoyl]cyclopentyl]ethylcarbamoyl]ethoxy]ethoxy]ethoxy]ethoxy]ethoxy]ethoxy]ethoxy]ethoxy]ethoxy]ethoxy]ethoxy]ethoxy]ethoxy]ethoxy]ethoxy]ethoxy]ethoxy]ethoxy]ethoxy]ethoxy]ethyl]succinamic acid was added sulfo-NHS ester (18.1 mg, 83.6 μmol, Eq:2) and then EDC (16.0 mg, 83.6 μmol, Eq:2). The reaction mixture was stirred at room temperature under nitrogen for 17 h. An additional 5 mg of sulfo-NHS ester and 18 mg of EDC were added, the reaction mixture was stirred for another 4.5 h, and then the solution containing N-[2-[2-[2-[2-[2-[2-[2-[2-[2-[2-[2-[2-[2-[2-[2-[2-[2-[2-[2-[2-[2-[2-[1-[(S)-1-tert-butoxycarbonyl-2-[4-(2,6-dichlorobenzoylamino)phenyl]ethylcarbamoyl]cyclopentyl]ethylcarbamoyl]ethoxy]ethoxy]ethoxy]ethoxy]ethoxy]ethoxy]ethoxy]ethoxy]ethoxy]ethoxy]ethoxy]ethoxy]ethoxy]ethoxy]ethyl]succinamic acid 2,5-dioxo-3-sulfo-pyrrolidin-1-yl ester sodium salt was taken to the next step for the attachment of chitosan derivative. ES(+)-LRMS m/e calcd. for $C_{87}H_{142}N_5O_{37}Cl_2S$ (M+H)$^+$ 1953.0, obsd. 977 ((M+H)/2)$^+$.

VLA$_4$ Ligand 3:
(S)-2-[4-[(3-[2-[2-[2-[2-[2-[2-[2-[2-[3-(2,5-Dioxo-2,5-dihydropyrrol-1-yl)propionylamino]ethoxy]ethoxy]ethoxy]ethoxy]ethoxy]ethoxy]ethoxy]propionylamino)methyl]-2,6-difluorobenzoylamino]-3-[4-(1,3,6-trimethyl-2,4-dioxo-1,2,3,4-tetrahydropyrimidin-5-yl)phenyl]propionic acid trifluoracetate salt Step 1: Preparation of (S)-2-tert-butoxycarbonylamino-3-[4-(1,3,6-trimethyl-2,4-dioxo-1,2,3,4-tetrahydropyrimidin-5-yl)phenyl]propionic acid methyl ester

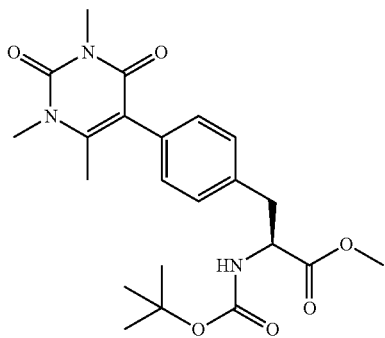 [SMILES: COC(=O)[C@H](Cc1ccc(-c2c(C)n(C)c(=O)n(C)c2=O)cc1)NC(=O)OC(C)(C)C]

To a suspension of zinc dust (52.29 g, 800 mmol) in THF (26.0 mL) was added 1,2-dibromoethane (4.58 mL, 53.2 mmol) at room temperature. This suspension was heated to 60-65° C. with a heat gun until evolution of ethylene gas ceased (observed). The suspension was cooled to room temperature, trimethylchlorosilane (3.38 mL, 26.6 mmol) was added and the mixture was stirred for 15 min. A suspension of 5-iodo-1,3,6-trimethyl uracil (74.6 g, 266 mmol) in DMA (225 mL) was warmed to obtain a clear solution and was added in one portion to the reaction mixture. After addition, the mixture was heated to 70° C. The internal temperature of the reaction mixture rose to 80-85° C. due to the exothermic reaction. The reaction mixture was stirred at 70° C., for 3-4 h at which time TLC of an aliquot which had been quenched with saturated ammonium chloride indicated the absence of starting material. The reaction mixture was diluted with THF (140 mL), was cooled to room temperature and the excess zinc dust was allowed to settle over 2-3 h.

This solution containing the zinc compound (266 mmol) was added to a solution of Pd(dba)$_2$ (4.6 g, 8 mmol), tri-o-tolylphosphine [P(Tol)$_3$] (9.0 g, 29.6 mmol) and (S)-2-tert-butoxycarbonylamino-3-(4-iodo)phenyl]propionic acid methyl ester (75.56 g, 186 mmol) in THF (280 mL) at room temperature and the light yellow mixture was stirred for 48 h at 50-55° C. The reaction mixture was poured into a saturated ammonium chloride solution and was extracted with ethyl acetate (3×750 mL). The combined extracts were washed with brine solution (1.5 L) and dried over anhydrous magnesium sulfate. Filtration of the drying agent and concentration gave the crude product which was purified by silica gel column chromatography using a Biotage (75 m) column to obtain 57.88 g (72% yield) of (S)-2-tert-butoxycarbonylamino-3-[4-(1,3,6-trimethyl-2,4-dioxo-1,2,3,4-tetrahydropyrimidin-5-yl)phenyl]propionic acid methyl ester as an amorphous white solid. EI-HRMS m/e calcd for C$_{22}$H$_{29}$N$_3$O$_6$ (M$^+$) 431.2056, found 431.2054.

Step 2: Preparation of (S)-2-amino-3-[4-(1,3,6-trimethyl-2,4-dioxo-1,2,3,4-tetrahydropyrimidin-5-yl)phenyl]propionic acid methyl ester hydrochloride salt

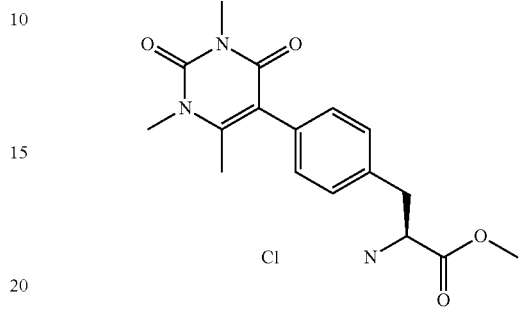

A portion of the solid (S)-2-tert-butoxycarbonylamino-3-[4-(1,3,6-trimethyl-2,4-dioxo-1,2,3,4-tetrahydropyrimidin-5-yl)phenyl]propionic acid methyl ester (7.4 g, 17.15 mmol) obtained above was treated with 4N hydrochloric acid in dioxane (17 mL, 68 mmol,) at room temperature and the solution was stirred for 1 h as a white precipitate formed. The mixture was diluted with diethyl ether and the supernatant was decanted and the residue was dried first on the rotary evaporator and then under high vacuum to afford 6.28 g (99% yield) of (S)-2-amino-3-[4-(1,3,6-trimethyl-2,4-dioxo-1,2,3,4-tetrahydropyrimidin-5-yl)phenyl]propionic acid methyl ester hydrochloride salt as an amorphous yellow solid. FAB-HRMS m/e calcd for C$_{17}$H$_{21}$N$_3$O$_4$ (M+H) 332.1610, found 332.1617.

Step 3: Preparation of (S)-2-(4-bromo-2,6-difluorobenzoylamino)-3-[4-(1,3,6-trimethyl-2,4-dioxo-1,2,3,4-tetrahydropyrimidin-5-yl)phenyl]propionic acid propyl ester

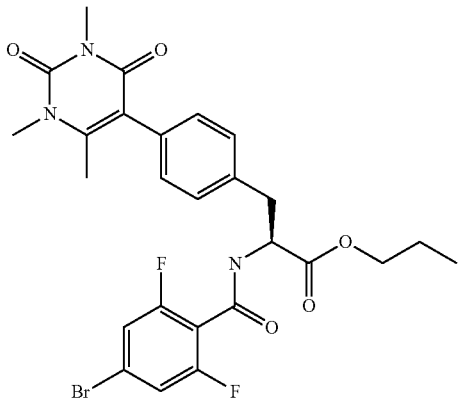 [SMILES: CCCOC(=O)[C@H](Cc1ccc(-c2c(C)n(C)c(=O)n(C)c2=O)cc1)NC(=O)c1c(F)cc(Br)cc1F]

To a suspension of (S)-2-amino-3-[4-(1,3,6-trimethyl-2,4-dioxo-1,2,3,4-tetrahydropyrimidin-5-yl)phenyl]propionic acid propyl ester (4.67 g, 13 mmol) 4-bromo-2,6-difluorobenzoic acid (3.12 g, 13.16 mmol), and HBTU (4.99 g, 13.16 mmol) in DMF (60 mL) was added diisopropylethylamine (6.8 mL, 39 mmol) at room temperature. After 1 min, everything went into solution and the solution was stirred for 36 h at room temperature. The brown solution was poured into water (500 mL) to afford a cloudy suspension. Then, the organic compound was extracted with ethyl acetate (2×200 mL). The combined extracts were washed successively with 1N hydrochloric acid (100 mL), saturated sodium bicarbonate solution (100 mL), and brine solution (200 mL) and was dried over anhydrous magnesium sulfate. Filtration of the drying agent and concentration of the solvent gave the crude product which was purified using an ISCO (400 g) column chromatography to afford 14.1 g (85% yield) of (S)-2-(4-bromo-2,6-difluorobenzoylamino)-3-[4-(1,3,6-trimethyl-2,4-dioxo-1,2,3,4-tetrahydropyrimidin-5-yl)phenyl]propionic acid propyl ester as an amorphous off-white solid. ES-HRMS m/e calcd for $C_{26}H_{26}BrF_2N_3O_5$ $(M+H)^+$ 578.1097, found 578.1096.

Step 4: Preparation of (S)-2-(4-cyano-2,6-difluorobenzoylamino)-3-[4-(1,3,6-trimethyl-2,4-dioxo-1,2,3,4-tetrahydropyrimidin-5-yl)phenyl]propionic acid propyl ester

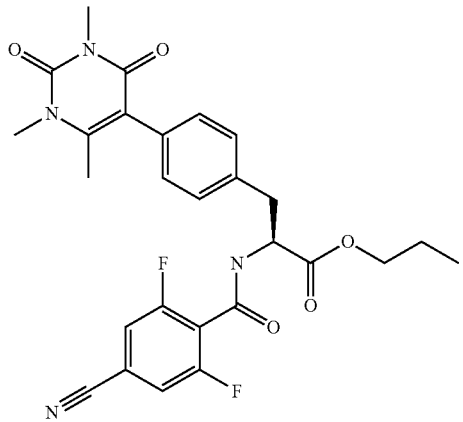 [SMILES: CCCOC(=O)[C@H](Cc1ccc(-c2c(C)n(C)c(=O)n(C)c2=O)cc1)NC(=O)c1c(F)cc(C#N)cc1F]

To a suspension of (S)-2-(4-bromo-2,6-difluorobenzoylamino)-3-[4-(1,3,6-trimethyl-2,4-dioxo-1,2,3,4-tetrahydropyrimidin-5-yl)phenyl]propionic acid propyl ester (5.78 g, 10 mmol), zinc cyanide (940 mg, 8 mmol), and tetrakis(triphenylphosphine)palladium (1.16 g, 1 mmol) in DMF (40 mL, distilled and degassed) at room temperature. The resulting solution was heated to 85° C. and stirred for 24 h at which time TLC analysis of the mixture indicated the absence of starting material. Then, the reaction mixture was cooled to room temperature and it was poured into water (100 mL) to afford a cloudy suspension. Then, the organic compound was extracted with ethyl acetate (2×100 mL). The combined extracts were washed with brine solution (100 mL) and dried over anhydrous magnesium sulfate. Filtration of the drying agent and concentration of the solvent gave the crude product which was purified using an ISCO (150 g) column chromatography to afford 5.2 g (99% yield) of (S)-2-(4-cyano-2,6-difluorobenzoylamino)-3-[4-(1,3,6-trimethyl-2,4-dioxo-1,2,3,4-tetrahydropyrimidin-5-yl)phenyl]propionic acid propyl ester as an amorphous white solid. ES HRMS m/e calcd for $C_{27}H_{26}F_2N_4O_5$ $(M+H)^+$ 525.1944, found 525.1942.

Step 5: Preparation of (S)-2-(4-aminomethyl-2,6-difluorobenzoylamino)-3-[4-(1,3,6-trimethyl-2,4-dioxo-1,2,3,4-tetrahydropyrimidin-5-yl)phenyl]propionic acid propyl ester

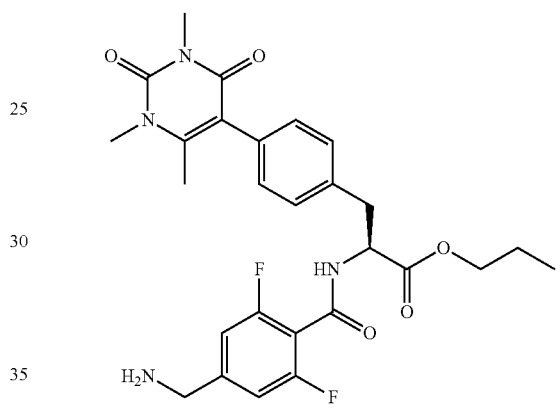

To solution of sodium borohydride (0.29 g, 7.62 mmol, 2 eq.) in THF (5 ml) was added TFA (566 µl, 7.62 mmol, 2 eq.), the reaction was stirred for 10 min., and then a solution of (S)-2-(4-cyano-2,6-difluoro-benzoylamino)-3-[4-(1,3,6-trimethyl-2,4-dioxo-1,2,3,4-tetrahydro-pyrimidin-5-yl)-phenyl]-propionic acid propyl ester (2.0 g, 3.81 mmol) in THF (6 ml) was added drop wise (flask was rinsed w/THF (2×1 ml) and added to reaction). The reaction was stirred at room temperature under nitrogen for 1.3 h. The reaction mixture was cooled in an ice bath and quenched with water (20 ml) and a sodium chloride solution (20 ml water, 100 ml saturated solution). The aqueous mixture was extracted with DCM (2×200 ml), to organic layers wash with brine, combined, dried over magnesium sulfate, and concentrated yield an off white solid 1.77 g. The crude was suspended in isopropyl acetate (75 ml) and isopropyl alcohol (0.75 ml and TMSCl (1 ml) was added dropwise. The reaction was stirred at room temperature for 2 h and the white precipitate was filtered and washed with isopropyl acetate and hexanes to obtain 1.5 g (63% yield) (S)-2-(4-aminomethyl-2,6-difluorobenzoylamino)-3-[4-(1,3,6-trimethyl-2,4-dioxo-1,2,3,4-tetrahydropyrimidin-5-yl)phenyl]propionic acid propyl ester as an amorphous white solid. ES-HRMS calcd for $C_{27}H_{30}F_2N_4O_5$ $(M+H)^+$ 529.2257, found 529.2258.

Step 6: Preparation of (S)-2-(4-aminomethyl-2,6-difluorobenzoylamino)-3-[4-(1,3,6-trimethyl-2,4-dioxo-1,2,3,4-tetrahydropyrimidin-5-yl)phenyl]propionic acid

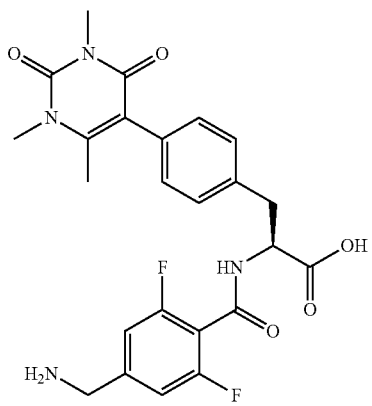 [SMILES: Cc1c(-c2ccc(C[C@H](NC(=O)c3c(F)cc(CN)cc3F)C(=O)O)cc2)c(=O)n(C)c(=O)n1C]

To a suspension of (S)-2-(4-aminomethyl-2,6-difluorobenzoylamino)-3-[4-(1,3,6-trimethyl-2,4-dioxo-1,2,3,4-tetrahydropyrimidin-5-yl)phenyl]propionic acid propyl ester (508 mg, 0.96 mmol) in THF (10 mL) was added a solution of lithium hydroxide (240 mg, 10 mmol) in water (2 mL) at room temperature. The mixture was stirred for 15 h at which time TLC analysis indicated the absence of starting material. Then, the THF was removed under reduced pressure and the residue was diluted with water (100 mL) and the mixture was acidified with TFA. The crude was purified by HPLC method to afford 450 mg (78% yield) of (S)-2-(4-aminomethyl-2,6-difluorobenzoylamino)-3-[4-(1,3,6-trimethyl-2,4-dioxo-1,2,3,4-tetrahydropyrimidin-5-yl)phenyl]propionic acid as a TFA salt as a white solid. ES-LRMS m/e calcd for $C_{24}H_{24}F_2N_4O_5$ (M+H)$^+$ 487, found 487.

Step 7: Preparation of (S)-2-[4-[(3-[2-[2-[2-[2-[2-[2-[2-[2-[3-(2,5-dioxo-2,5-dihydropyrrol-1-yl)propionylamino]ethoxy]ethoxy]ethoxy]ethoxy]ethoxy]ethoxy]ethoxy]propionylamino)methyl]-2,6-difluorobenzoylamino]-3-[4-(1,3,6-trimethyl-2,4-dioxo-1,2,3,4-tetrahydropyrimidin-5-yl)phenyl]propionic acid

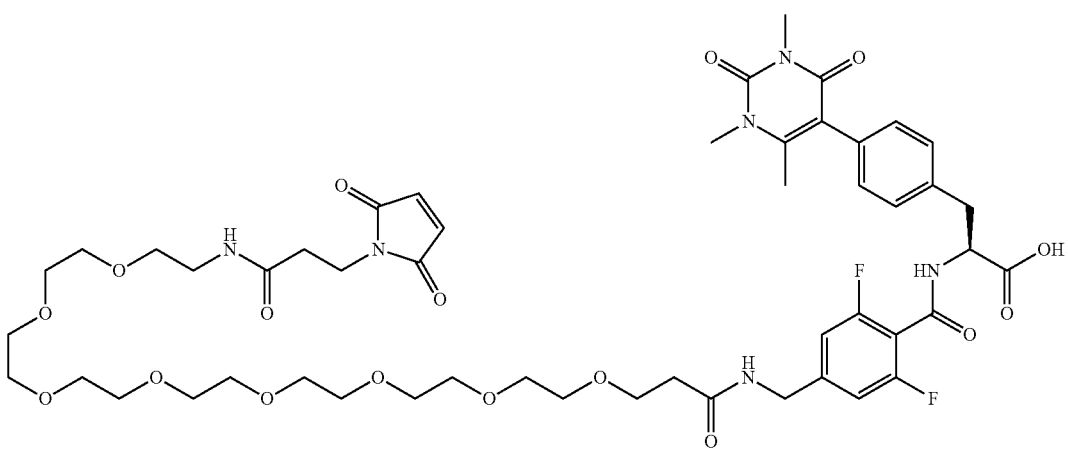 [SMILES: Cc1c(-c2ccc(C[C@H](NC(=O)c3c(F)cc(CNC(=O)CCOCCOCCOCCOCCOCCOCCOCCOCCNC(=O)CCN4C(=O)C=CC4=O)cc3F)C(=O)O)cc2)c(=O)n(C)c(=O)n1C]

A similar procedure as described in General method, Step 10 of αvβ3 ligand 1 was used, starting from (S)-2-(4-aminomethyl-2,6-difluorobenzoylamino)-3-[4-(1,3,6-trimethyl-2,4-dioxo-1,2,3,4-tetrahydropyrimidin-5-yl)phenyl] propionic acid TFA salt (121 mg, 0.2 mmol, 3-[2-[2-[2-[2-[2-[2-[2-[2-[3-(2,5-dioxo-2,5-dihydro-pyrrol-1-yl)-propionylamino]-ethoxy]ethoxy]ethoxy]ethoxy]ethoxy]ethoxy]ethoxy]-propionic acid-2,5-dioxo-pyrrolidin-1-yl ester (100 mg, 0.145 mmol), and DIPEA (258 mg, 348 uL, 2.0 mmol) to obtain, after HPLC purification, 80 mg (38% yield) of (S)-2-[4-[(3-[2-[2-[2-[2-[2-[2-[2-[2-[3-(2,5-dioxo-2,5-dihydropyrrol-1-yl)propionylamino]ethoxy]ethoxy]ethoxy]ethoxy]ethoxy]ethoxy]ethoxy]propionylamino)methyl]-2,6-difluorobenzoylamino]-3-[4-(1,3,6-trimethyl-2,4-dioxo-1,2,3,4-tetrahydropyrimidin-5-yl)phenyl]propionic acid as a white solid. ES(+)-HRMS m/e calcd. for $C_{50}H_{66}F_2N_6O_{17}$ $(M+H)^+$ 1061.4526, obsd. 1061.4521.

Procedures for Synthesis of Integrin Antagonist-Derivatized Chitosans

Definitions

Loading values were determined by $^1$H NMR integrations of the thioacetyl, alkyl, aromatic peaks, or combination average with respect to the known value of the acetyl group of the starting chitosan. Percent loading was reported in mole %. The concentration of the loaded ligand was reported in nanomoles of ligand with respect to the average molecular weight of the monomer of the biopolymer per milligram of chitosan. The average molecular weight of the monomer was determined by the sum of the mole percent of each monomer's molecular weight. The N value was reported as micromoles of primary amine per milligram of chitosan, μmol/mg. The following abbreviations have the below definitions:

Cs=Chitosan,

NM=Nova Matrix (Catalog #UP B 80/20), Protosan (trade name for chitosan) 14% acetylated, used as is, AK=AK scientific (Catalog #K638), chitosan, 2.5% acetylated, used as is, Pr—S=3-Mercapto-propionamide

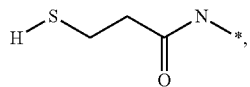

Pr—S—Ac=Thioacetic acid S-(2-carbamoyl-ethyl) ester-amide

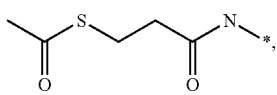

PEG12=

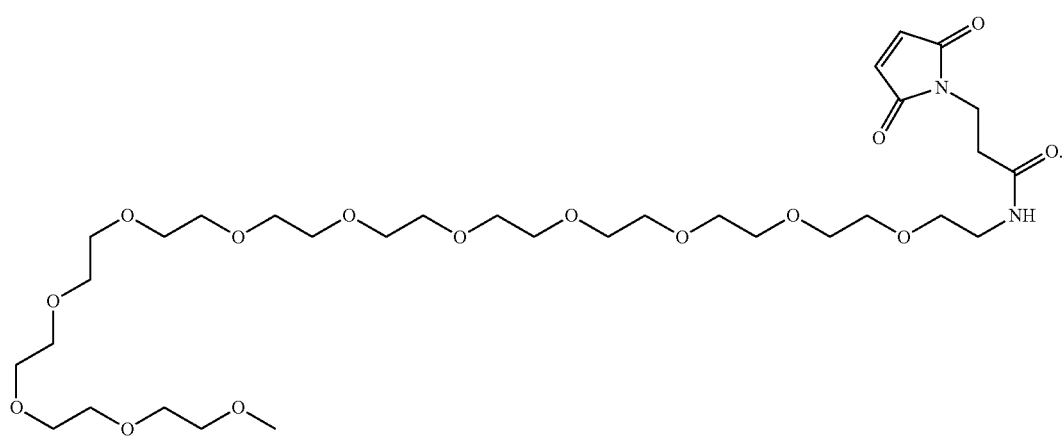 [SMILES: COCCOCCOCCOCCOCCOCCOCCOCCOCCOCCOCCOCCNC(=O)CCN1C(=O)C=CC1=O]

In addition, the following table describes which variables in Formula I of the present invention apply to each of the named ligands prepared above. For example, in the table R1 is either: (1) the small molecule antagonist for αVβ3:

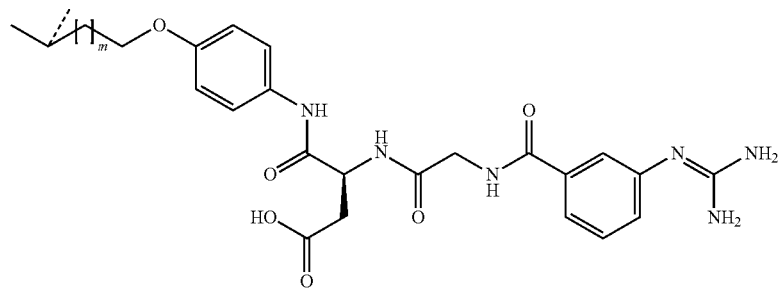

or (2) the small molecule antagonist for α4⊕1:

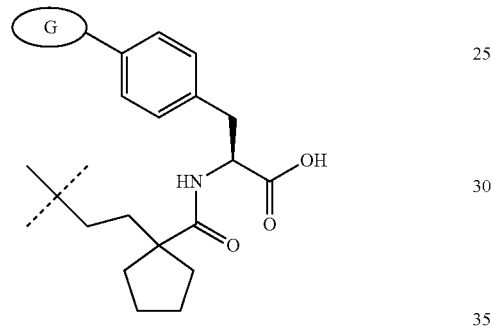

Likewise, Y is either: (1) amide-propionyl-thiol-maleimide-propionly-amide (Pr—S-Mal), or (2) succinic acid amide (Suc); and specification of the remaining variables are self-explanatory based on the variables as described for Formula I in the beginning of the Detailed Description.

| Ligand From Above Examples | Small Molecule Antagonist for the R1 Variable | Specification Of Variables Within R1 | PEG length | Specification of the Y Variable |
| --- | --- | --- | --- | --- |
| αVβ3 Ligand 1 | antagonist for αVβ3 | m = 1 | n = 7 | Y = Pr—S-Mal |
| αVβ3 Ligand 2 | antagonist for αVβ3 | m = 1 | n = 11 | Y = Pr—S-Mal |
| αVβ3 Ligand 3 | antagonist for αVβ3 | m = 0 | n = 11 | Y = Pr—S-Mal |
| α4β1 Ligand 1 | antagonist for α4β1 | G = 2,6-dichlorobenzamido | n = 7 | Y = Pr—S-Mal |
| α4β1 Ligand 2 | antagonist for α4β1 | G = 2,6-dichlorobenzamido | n = 23 | Y = Suc |
| α4β1 Ligand 3 | antagonist for α4β1 | G = 1,3,6-trimethyl-2,4-dioxo-1,2,3,4-tetrahydropyrimidin-5-yl | n = 7 | Y = Pr—S-Mal |

Example 1

Cs(NM)-αvβ3 Ligand 3 (0.3% Loading) (Chitosan Derivative D)

Step 1: Cs(NM)-Pr—S—Ac(0.26%)

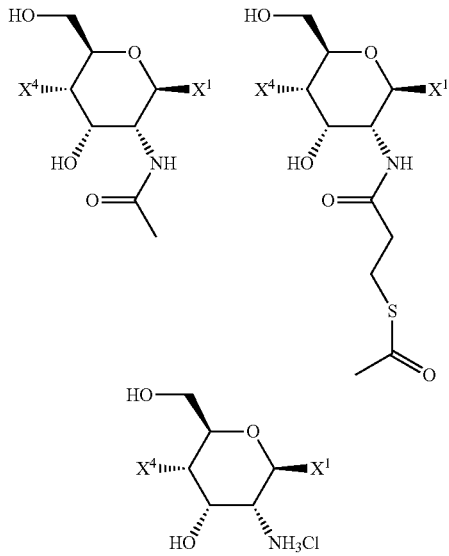

In an Erlenmeyer flask was added Protosan (novamatrix (NM)) (200 mg, 1.13 mmol), 1H-benzo[d][1,2,3]triazol-1-ol (153 mg, 1.13 mmol, Eq: 1.0), 3-(acetylthio)propanoic acid (836 µg, 5.64 µmol, Eq: 0.005), and water (50 mL). The mixture was stirred until a clear colorless solution formed, and then was diluted with Acetonitrile (50.0 mL). To this was added EDC (3.25 mg, 16.9 µmol, Eq: 0.015) and the reaction was stirred at RT for 13 hr. The reaction was partially acidified with 1 mL of 0.1 M HCl, concentrated, transferred to a dialysis bag (10K MWCO, Thermo Scientific, Snake Skin), and dialyzed against 4 L of 2.5% NaCl solution for 3 h, 2% for 5 h, 1% for 6 h, 0.5% 12 h, water 12 h 4 times. The dialysate was lypholized yielding off white fibrous solid, 158 mg. The loading was determined by $^1$H NMR integration of the methyl of the thioacetate at 2.21 ppm as compared to the methyl of the N acetate at 1.9 ppm (14% assumed) was 0.26 mole %, 13.3 nmol/mg, and the N values was 4.32 nmol/mg (0.26%, 13.3 nmol/mg, N 4.32 µmol/mg), Step 2 Cs(NM)-Pr—SH (0.26%)

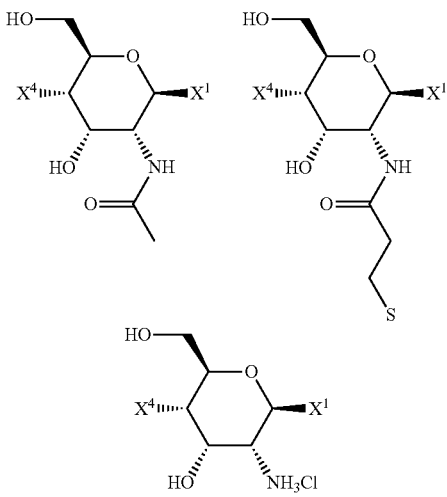

In a 20 mL vial, Cs(NM)-Pr—S—Ac (0.26%) (46.6 mg) was combined with HCl (0.1 M) (15.0 mL, previously degassed with nitrogen) to give a clear slight yellow tint solution. The solution was purged with nitrogen (1 min), sealed, wrapped in aluminum foil, and heated in a heating block at 100° C. in the dark. After 4 h, the vial was placed in a freezer (−20° C.) overnight. The next day the reaction was transferred to a round bottom flask (200 mL), rinsed with 0.1 M HCl (previously degassed with nitrogen), concentrated under reduced pressure producing a clear to opaque off white film/sheet solid. The material was immediately used as is (0.26%, 13.3 nmol/mg).

Step 3: Cs(NM)-αvβ3 Ligand 3 (0.3% Loading) (Chitosan Derivative D)

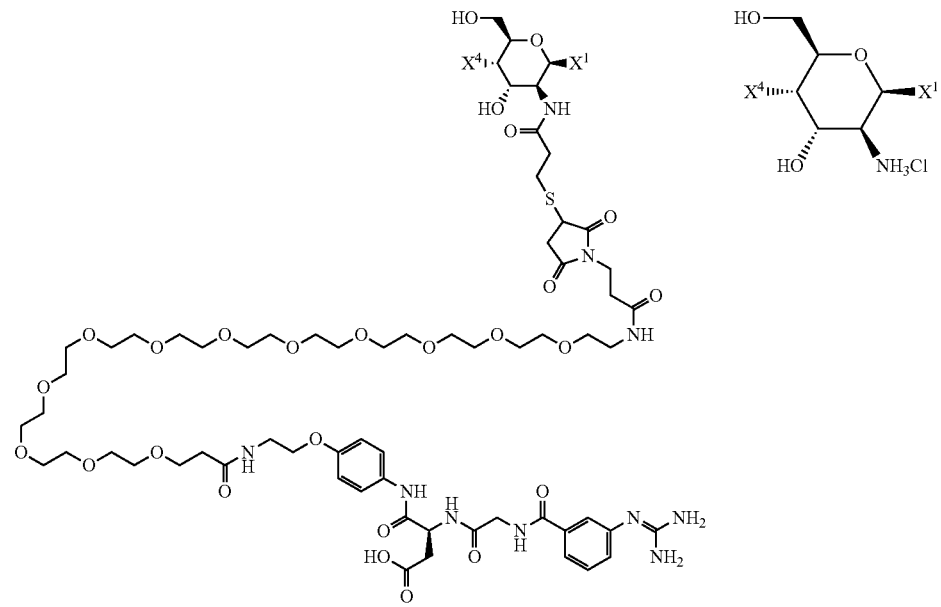

In a pear shaped round bottom flask, Cs(NM)-Pr—SH (0.26%) (44 mg, 13.3 nmol/mg, 0.585 µmol) was dissolved in water (5 mL, previously degassed with nitrogen). The pH of the reaction was adjusted to pH 6.2-6.3 with aqueous NaOH (1 M). The αvβ3 Ligand 3 (2.13 mg, 1.72 µmol, Eq 3) in a test tube was dissolved in DMSO (1 mL, and 0.5 mL rinse; previously degassed with nitrogen) and then transferred by pipette to the reaction. The reaction was stirred at RT under nitrogen for 11 h. The reaction was acidified (HCl, 0.1 M, 3 mL), diluted with aqueous NaCl (5 mL, 10%), and stirred for 5-10 min. The reaction was transferred (and rinsed once with water 5 mL) into a Vivacell 70 (Sartoriusstedim) membrane centrifuge device (10K MWCO). The solution was concentrated by centrifugation (~1K), and the retentate was re-suspended and concentrated 3 times with water, and one time 0.001 M HCl. The retentate were transferred with two rinsings of water (1 mL/ea) to a syringe with a 0.45 µm PVDF (Gelman Aerodisc) syringe filter, filtered, and lyophilized yielding a white fibrous solid, 11 mg. The loading of the ligand, as determined by $^1$H NMR integration of the rounded average the aromatic peak at 6.85 ppm and the methylene peak at 2.33 ppm compared to the methyl of the acetate at 1.9 ppm, was 0.3% (15 nmol/mg) and the N value was 4.2 µmol/mg (0.3%, 15 nmol/mg, N 4.2 µmol/mg). The values were based on the NMR.

Example 2

Cs(NM)-αvβ3 Ligand 3 (0.6% Loading) (Chitosan Derivative E)

Step 1: Cs(NM)-Pr—S—Ac (0.47%)

The product (clear to opaque off white film/sheet solid, 176 mg) was prepared by a similar procedure as Cs(NM)-Pr—S—Ac (0.26%) from Protosan (200 mg, 1.13 mmol), 1H-benzo[d][1,2,3]triazol-1 (153 mg, 1.13 mmol, Eq: 1.0), 3-(acetylthio)propanoic acid (1.67 mg, 11.3 µmol, Eq: 0.01), and EDC (6.49 mg, 33.9 µmol, Eq: 0.03). (0.47%, N 4.30 nmol/mg).

Step 2: Chitosan(NM)-Pr—SH (0.47%)

The product (clear to opaque off white film/sheet solid) was prepared by a similar procedure as Cs(NM)-Pr—SH (0.26%) from Cs(NM)-Pr—S—Ac (0.47%) (47.5 mg). The material was used as is (0.47%, 23.7 nmol/mg).

Step 3: Cs(NM)-αvβ3 Ligand 3 (0.6% Loading) (Chitosan Derivative E)

The product (a white fibrous solid, 20 mg) was prepared by a similar procedure as Cs(NM)-Pr—S-αvβ3 Ligand 3 (0.3%) from Cs(NM)-Pr—SH (0.47%) (42 mg, 23.7 nmol/mg, 0.995 µmol) and αvβ3 Ligand 3 (3.7 mg, 2.99 µmol, Eq. 3). (0.6% (29 nmol/mg, N 4.1 µmol/mg).

Example 3

Cs(NM)-αvβ3 Ligand 3 (1.9% Loading) (Chitosan Derivative F)

Step 1: Cs(NM)-Pr—S—Ac (1.9%)

The product (clear to opaque off white film/sheet solid, 226 mg) was prepared by a similar procedure as Cs(NM)-Pr—S—Ac (0.26%) from Protosan (200 mg, 1.13 mmol), 1H-benzo[d][1,2,3]triazol-1-ol (153 mg, 1.13 mmol, Eq: 1.0), 3-(acetylthio)propanoic acid (5.02 mg, 33.9 µmol, Eq: 0.03), and EDC (19.5 mg, 102 µmol, Eq: 0.09). (1.9%, N 4.20 nmol/mg).

Step 2: Cs(NM)-Pr—SH (13%)

The product (clear to opaque off white film/sheet solid) was prepared by a similar procedure as Cs(NM)-Pr'SH (0.26%)) from Cs(NM)-Pr—S—Ac (1.9%) (48 mg). The material was used as is (1.9%, 95.3 nmol/mg).

Step 3: Cs(NM)-αvβ3 Ligand 3 (1.9% Loading) (Chitosan Derivative F)

The product (a white fibrous solid, 28 mg) was prepared by a similar procedure as Cs(NM)-Pr—S-αvβ3 Ligand 3 (0.3%) from Cs(NM)-Pr—SH (1.9%) (45 mg, 95.3 nmol/mg, 4.29 µmol) and αvβ3 Ligand 3 (15.9 mg, 12.8 µmol, Eq 3). (1.9%, 89 nmol/mg, N 3.7 µmol/mg).

Example 4

Cs(NM)-αvβ3 Ligand 3 (6% Loading) (Chitosan Derivative G)

Step 1: Cs(NM)-Pr—S—Ac (6.1%)

The product (clear to opaque off white film/sheet solid, 43 mg was prepared by a similar procedure as Cs(NM)-Pr—S—Ac (0.26%) from Protosan (200 mg, 1.13 mmol), 1H-benzo[d][1,2,3]triazol-1-ol (153 mg, 1.13 mmol, Eq: 1.0), 3-(acetylthio)propanoic acid (10 mg, 67.7 µmol, Eq: 0.06), and EDC (39 mg, 203 µmol, Eq: 0.18). (6.1%, N 3.92 nmol/mg).

Step 2: Cs(NM)-Pr—SH (6.1%)

The product (clear to opaque off white film/sheet solid) was prepared by a similar procedure as Cs(NM)-Pr—SH (0.26%) from Cs(NM)-Pr—S—Ac (6.1%) (32.5 mg). The material was immediately used as is (6.05%, 300.1 nmol/mg).

Step 3: Cs(NM)-αvβ3 Ligand 3 (6% Loading) (Chitosan Derivative G)

The product (a white fibrous solid, 17 mg) was prepared by a similar procedure as Cs(NM)-Pr—S-αvβ3 Ligand 3 (0.3%) from Cs(NM)-Pr—SH (6.1%) (30 mg, 300.1 nmol/mg, 9.00 µmol) and αvβ3 Ligand 3 (32.7 mg, 26.4 µmol, Eq. 3). (6%, 217 nmol/mg, N 2.9 µmol/mg).

Example 5

Cs(NM)-αvβ3 Ligand 3 (5% Loading) (Chitosan Derivative H)

Step 1: Cs(NM)-Pr—S—Ac (8.8%)

The product (clear to opaque off-white film/sheet solid, 165 mg) was prepared by a similar procedure as Cs(NM)-Pr—S—Ac (0.26%) from Protosan (200 mg, 1.13 mmol), 1H-benzo[d][1,2,3]triazol-1-ol (153 mg, 1.13 mmol, Eq: 1.0), 3-(acetylthio)propanoic acid (15.1 mg, 102 µmol, Eq: 0.09), and EDC (58.4 mg, 305 µmol, Eq: 0.27). (8.8%, N 3.73 nmol/mg).

Step 2: Cs(NM)-Pr—SH (8.8%)

The product (clear to opaque off white film/sheet solid) was prepared by a similar procedure as Cs(NM)-Pr—SH (0.26%) from Cs(NM)-Pr—S—Ac (8.8%) (48 mg). The material was immediately used as is (8.84%, 435.4 nmol/mg).

Step 3: Cs(NM)-αvβ3 Ligand 3 (5% Loading) (Chitosan Derivative H)

The product (a white fibrous solid, 15 mg) was prepared by a similar procedure as Cs(NM)-Pr—S-αvβ3 Ligand 3 (0.3%) from Cs(NM)-Pr—SH (8.8%) (32 mg, 435.4 nmol/mg, 13.9 μmol) and αvβ3 Ligand 3 (50.5 mg, 40.8 μmol, Eq. 2.9). (5.3%, 198 nmol/mg, N 3.0 μmol/mg).

Example 6

Cs(AK)-αvβ3 Ligand 2 (0.15% Loading) (Chitosan Derivative A)

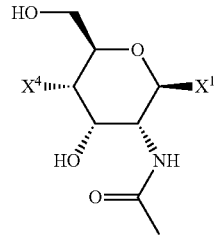

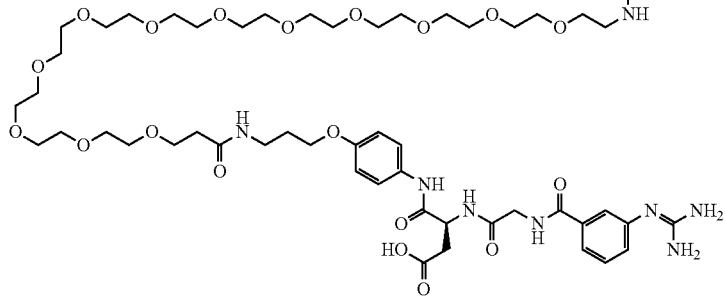

Step 1: Cs(Ak)-Pr—S—Ac (0.7%)

The product (white fibrous solid, 154 mg) was prepared by a similar procedure as Cs(NM)-Pr—S—Ac (0.26%) from chitosan (200 mg) purchased from Chitosan (AK) (200 mg, 1.13 mmol), 1H-benzo[d][1,2,3]triazol-1-ol (168 mg, 1.24 mmol, Eq: 1.1), 3-(acetylthio)propanoic acid (1.67 mg, 11.3 μmol, Eq: 0.01), and EDC (64.9 mg, 339 μmol, Eq: 0.3). (0.7%, 34.8 nmol/mg, N 4.88 nmol/mg).

Step 2: Cs(Ak)-Pr—SH (0.7%)

The product (clear to opaque off white film/sheet solid) was prepared by a similar procedure as Cs(NM)-Pr—SH (0.26%) from Cs(Ak)-Pr—S—Ac (0.7%) (54 mg). The material was immediately used as is (0.69%, 34.8 nmol/mg).

Step 3: Cs(AK)-αvβ3 Ligand 2 (0.15% Loading) (Chitosan Derivative A)

The product (white fibrous solid, 41 mg) was prepared by a similar procedure as Cs(NM)-Pr—S-αvβ3 Ligand 3 (0.3%) from Cs(Ak)-Pr—SH (0.7%) (36 mg, 0.69%, 34.8 nmol/mg, 1.25 μmol) and αvβ3 Ligand 2 (3.7 mg, 2.84 μmol, Eq. 2.3). (0.15%, 7.5 nmol/mg, N 4.87 μmol/mg)

Example 7

Cs(AK)-αvβ3 Ligand 2 (0.21% Loading) (Chitosan Derivative B)

Step 1: Cs(Ak)-Pr—S—Ac (1.5%)

The product (white fibrous solid, 108 mg) was prepared by a similar procedure as Cs(NM)-Pr—S—Ac (0.26%) from chitosan (200 mg) purchased from Chitosan (AK) (200 mg, 1.13 mmol), 1H-benzo[d][1,2,3]triazol-1-ol (168 mg, 1.24 mmol, Eq: 1.1), 3-(acetylthio)propanoic acid (4.18 mg, 28.2 μmol, Eq: 0.025), and EDC (64.9 mg, 339 μmol, Eq: 0.3). (1.5%, 73.8 nmol/mg, N 4.82 nmol/mg).

Step 2: Cs(Ak)-Pr—SH (1.5%)

The product (clear to opaque off white film/sheet solid) was prepared by a similar procedure as Cs(NM)-Pr—SH (0.26%) from Cs(Ak)-Pr—S—Ac (1.5%) (49 mg). The material was immediately used as is (1.5%, 73.8 nmol/mg).

Step 3: Cs(AK)-αvβ3 Ligand 2 (0.21% Loading) (Chitosan Derivative B)

The product (white fibrous solid, 38 mg) was prepared by a similar procedure as Cs(NM)-Pr—S-αvβ3 Ligand 3 (0.3%) from Cs(Ak)-Pr—SH (1.5%) (28 mg, 1.5%, 73.8 nmol/mg, 1.85 μmol) and αvβ3 Ligand 2 (5.2 mg, 4.16 μmol, Eq. 2.2). (0.21%, 1.0.6 nmol/mg, N 4.85 μmol/mg)

Example 8

Cs(AK)-αvβ3 Ligand 2 (0.76% Loading) (Chitosan Derivative C)

Step 1: Cs(Ak)-Pr—S—Ac (1.8%)

The product (white fibrous solid, 77 mg) was prepared by a similar procedure as Cs(NM)-Pr—S—Ac (0.26%) from chitosan (205 mg) purchased from Chitosan (AK) (205 mg, 1.16 mmol), 1H-benzo[d][1,2,3]triazol-1-ol (208 mg, 1.54 mmol, Eq: 1.33), 3-(acetylthio)propanoic acid (10.5 mg, 70.9 μmol, Eq: 0.061), and EDC (78 mg, 407 μmol, Eq: 0.352). (1.8%, 88.5 nmol/mg N 4.80 nmol/mg).

Step 2: Cs(Ak)-Pr—SH (1.8%)

The product (clear to opaque off white film/sheet solid) was prepared by a similar procedure as Cs(NM)-Pr—SH (0.26%) from Cs(Ak)-Pr—S—Ac (1.8%) (50 mg). The material was immediately used as is (1.8%, 88.5 nmol/mg).

Step 3: Cs(AK)-αvβ3 Ligand 2 (0.76% Loading) (Chitosan Derivative C)

The product (white fibrous solid, 41 mg) was prepared by a similar procedure as Cs(NM)-Pr—S-αvβ3 Ligand 3 (0.3%) from Cs(Ak)-Pr—SH (0.38%) (29 mg, 3.7%, 182.3 nmol/mg, 5.29 μmol) and αvβ3 Ligand 2 (12.4 mg, 9.92 μmol, Eq.1.9). (0.76%, 36.7 nmol/mg, N 4.66 μmol/mg).

Example 9

Cs(NM)-VLA₄ Ligand 1 (21% Loading) (Chitosan Derivative I)

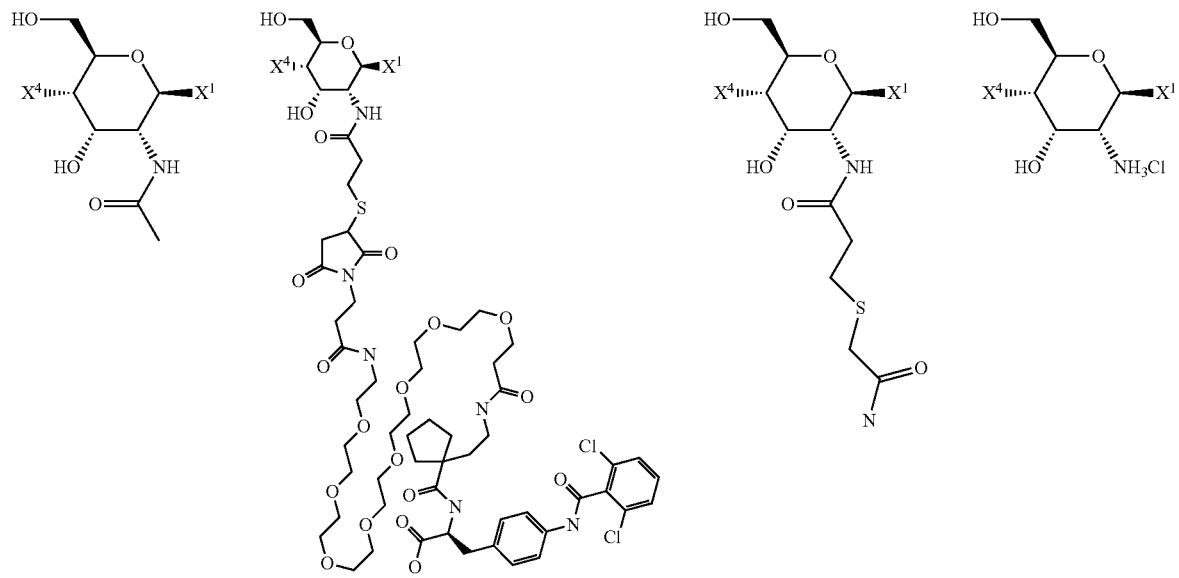

Step 1: Cs(NM)-Pr—S—Ac (25%)

The product (white solid) was prepared by a similar procedure as Cs(NM)-Pr—S—Ac (0.26%) from Protosan (280 mg, 1.58 mmol), 3-(acetylthio)propanoic acid (185.2 mg, 1.25 mmol, Eq: 0.79), and EDC (160 mg, 835 μmol, Eq: 0.528). (25%, 1180 nmol/mg).

Step 2: Chitosan(NM)-Pr—SH (25%)

The product (clear to opaque off white film/sheet solid) was prepared by a similar procedure as Cs(NM)-Pr—SH (0.26%) from Cs(NM)-Pr—S—Ac (25%). The material was used as is (25%, 1180 nmol/mg).

Step 3. Cs(NM)-VLA$_4$ Ligand 1 (Chitosan Derivative I (21% Loading)

The product (a white fibrous solid, 10 mg) was prepared by a similar procedure as Cs(NM)-Pr—S-αvβ3 Ligand 3 (0.3%) from Cs(NM)-Pr—SH (25%) (16.7 mg, 1180 nmol/mg, 19.8 μmol), DIEA (2.5 μL, 14.5 μmol, Eq. 1), and VLA$_4$ Ligand 1 (15.5 mg, 14.5 μmol, Eq. 0.7). The reaction was quenched with bromo-acetamide (Eq. 50), acidified with 1 M HCl, liquid extracted with ethyl acetate and hexanes mixtures, and was purified by dialysis (21%, 480 nmol/mg, N 1.4 μmol/mg).

Example 10

Cs(NM)-VLA$_4$ Ligand 3 (18% Loading) (Chitosan Derivative J)

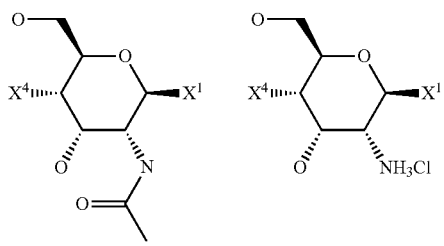

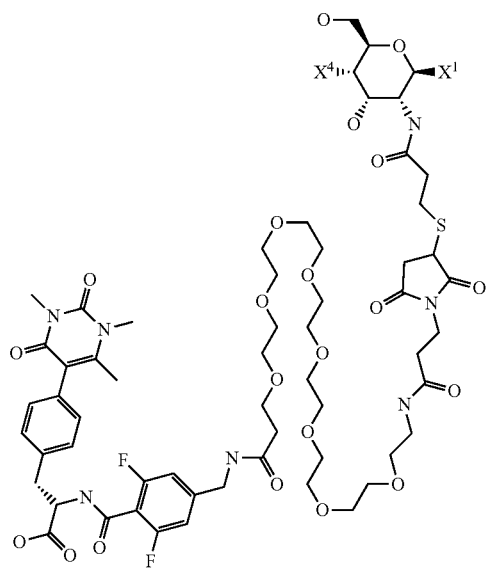

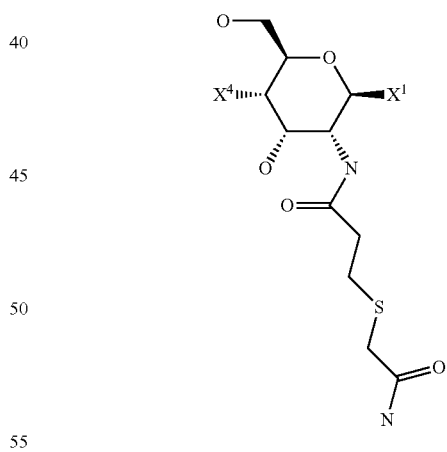

The product (a white fibrous solid, 13.4 mg) was prepared by a similar procedure as Cs(NM)-Pr—S-αvβ3 Ligand 3 (0.3%) from Cs(NM)-Pr—SH (25%) (18.3 mg, 1180 nmol/mg, 21.6 μmol), DIEA (3.7 μL, 21 μmol, Eq. 1), and VLA$_4$ Ligand 3 (22.5 mg, 21.2 μmol, Eq. 1). The reaction was quenched with bromo-acetamide (Eq. 22), acidified with 1 M HCl, and was purified by filtration through Amicon Ultra-15, 10K NMWL membrane. (18% (440 nmol/mg, N 1.4 μmol/mg).

Example 11

Cs(NM)-VLA₄ Ligand 2 Acid (4% Loading) (Chitosan Derivative K)

Step 1: Cs(NM)-VLA₄ Ligand 2-tert-butyl ester

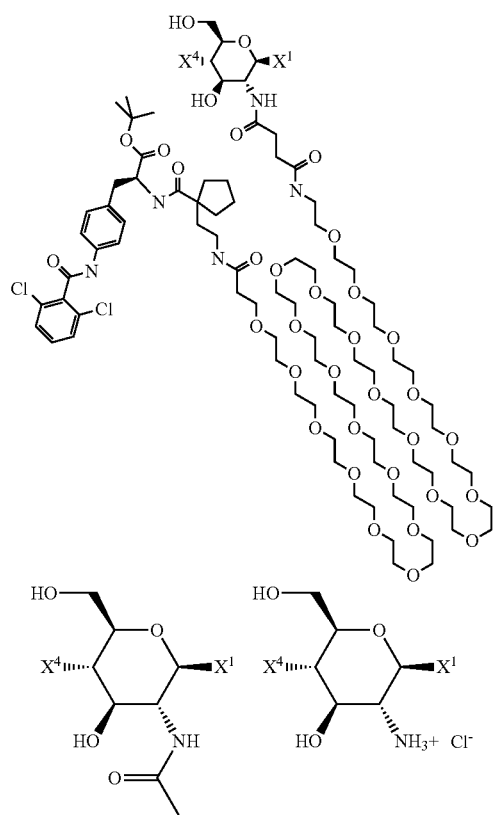

Step 2: Cs(NM)-VLA₄ Ligand 2 Acid (4% Loading) (Chitosan Derivative K)

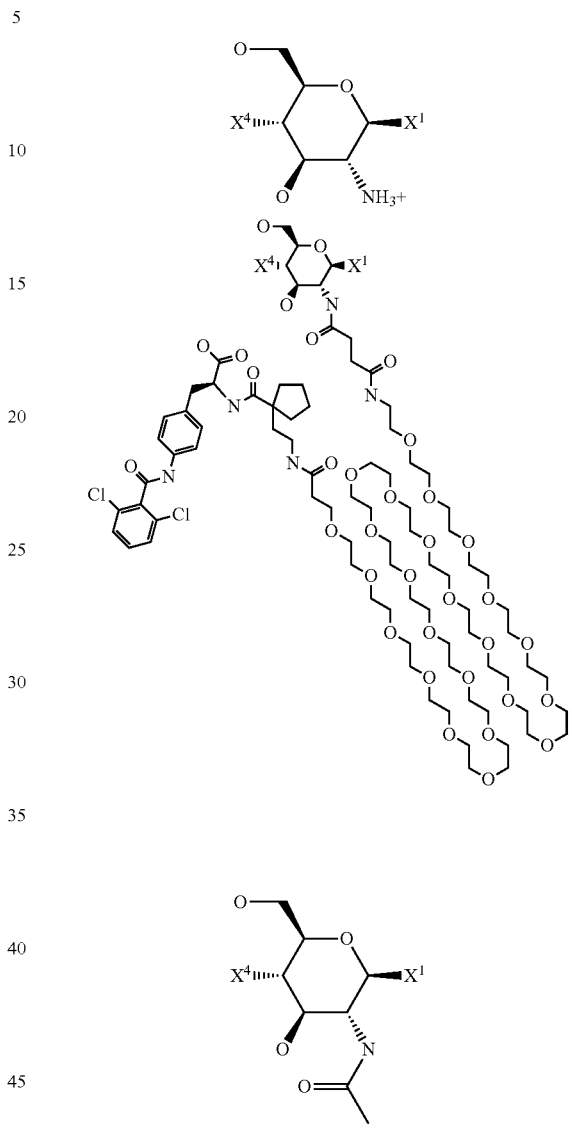

In a 20 mL vial, Cs(NM) (Chitosan)(16.9 mg, 83.6 μmol, Eq: 4) and HOBT (12.8 mg, N 4.33 μmol/mg, 55.4 μmol, Eq: 2.7) were combined with water (10 mL) to give a suspension. The mixture was stirred at: RT for 1.5 h to dissolve and form the CS-HOBT salt. The DMSO solution (0.55 ml) containing VLA₄ Ligand 2-tert-butyl ester (41.3 mg, 20.9 μmol, Eq: 1.00)) was added drop to portion wise with two rinsings (1 mL and 0.5 mL) and the reaction mixture was stirred at RT overnight for 19 h. Then, the reaction mixture was acidified with a.q. HCl (1 M, 0.5 mL), stirred at room temperature for 1 h, and filtered (via centrifuge) through Amicon membrane (Ultracell 10K MWCO, 5000 g) and washed with water (4×7 mL, 5000 g, 1-2 h). The retentate (0.5-1 mL) each time was a slight yellow very viscous oil with consistency of a thick syrup or honey, care was taken to ensure complete mixing prior to centrifuging. The final retentate was dissolved in ~20 mL of water and transferred to two 20 mL vials and lypholized over the weekend to obtain Cs(NM)-VLA₄ Ligand 2-tert-butyl ester as a white solid (26 mg and was used as is for the next step).

Cs(NM)-VLA₄-Ligand 2-tert-butyl ester (26 mg, from above reaction) was added aq HCl (0.2 M, 10 mL) and stirred at RT with shaking in a 20 mL. The material swelled and turned light yellow and had a "soapy foam" appearance. The material did not dissolve completely and was agitated with a spatula to break the material into smaller pieces. The reaction vessel was sealed and placed in a heating block at 100° C. and after 10 minutes everything dissolved and the soapy foam disappeared. After 1.5 h the vial was removed from the heat, allowed to cool to RT. There were particles in the solution and the solution was filtered through a whatman (#1) filter paper and the filtrate was purified by filtration (via centrifuge) through Amicon membrane (Ultracell 10K MWCO, 5000 g) and washed with dilute HCl (10 mL 0.01 M HCl and 10 mL of 0.005 M HCl 10 mL). The retentate was lypholized for 3.5 days to obtain Cs(NM)-VLA₄ Ligand 2 Acid as a white solid (13 mg, 144 nmol/mg, N 3.15 μmol/mg).

Example 12

Cs(NM)-Pr—S-PEG12 (0.14% Loading) (Chitosan Derivative L)

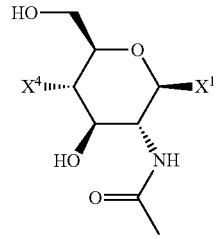
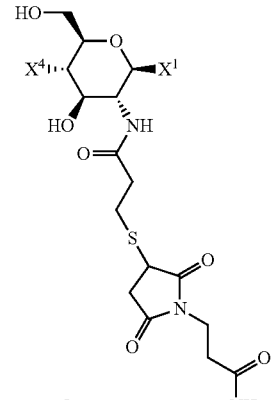
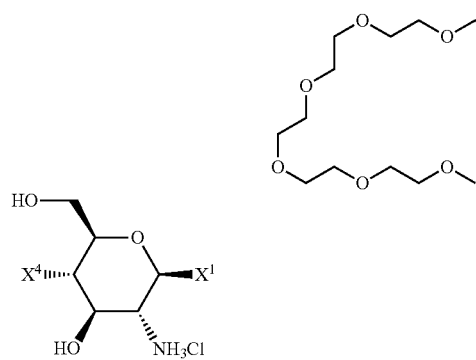

Cs(NM)-Pr—S-Peg12 (0.14% Loading) (Chitosan Derivative L)

The product (a white fibrous solid, 12 mg) was prepared by a procedure similar to that used for the preparation of Chitosan Derivative D. However, in this procedure, Cs(NM)-Pr—SH (0.26%) (26.8 mg, 13.3 nmol/mg, 0.356 μmol) is reacted with a PEG reagent which lacks any targeting element and terminates with a methoxy group: 3-(2,5-dioxo-2,5-dihydropyrrol-1-yl)-N-[2-[2-[2-[2-[2-[2-[2-[2-[2-[2-[2-[2-methoxyethoxy]ethoxy]ethoxy]ethoxy]ethoxy]ethoxy]ethoxy]ethoxy]ethoxy]ethoxy]ethoxy]ethyl]propionamide (2.5 mg, 3.5 μmol, Eq. 10) resulting in Chitosan Derivative L (0.14%, 6.9 nmol/mg, N 4.3 μmol/mg).

Cs(NM)-Pr—S-Peg12 (0.83% Loading) (Chitosan Derivative M)

The product (a white fibrous solid, 12 mg) was prepared by a procedure similar to that used for the preparation of Chitosan Derivative D. However, in this procedure, Cs(NM)-Pr—SH (0.47%) (27 mg, 23.7 nmol/mg, 0.640 μmol) is reacted with a PEG reagent which lacks any targeting element and terminates with a methoxy group: 3-(2,5-dioxo-2,5-dihydropyrrol-1-yl)-N-[2-[2-[2-[2-[2-[2-[2-[2-[2-[2-[2-[2-methoxyethoxy]ethoxy]ethoxy]ethoxy]ethoxy]ethoxy]ethoxy]ethoxy]ethoxy]ethoxy]ethoxy]ethyl] propionamide (4.6 mg, 6.4 μmol, Eq. 10)) resulting in Chitosan Derivative M (0.83%, 40.3 nmol/mg, N 4.16 μmol/mg).

Cs(NM)-Pr—S-Peg12 (1.4% Loading) (Chitosan Derivative N)

The product (a white fibrous solid, 13 mg) was prepared by a procedure similar to that used for the preparation of Chitosan Derivative D. However, in this procedure, Cs(NM) Pr—SH (1.9%) (24.3 mg, 95.3 nmol/mg, 2.32 μmol) is reacted with a PEG reagent which lacks any targeting element and terminates with a methoxy group: 3-(2,5-dioxo-2,5-dihydropyrrol-1-yl)-N-[2-[2-[2-[2-[2-[2-[2-[2-[2-[2-[2-[2-methoxyethoxy]ethoxy]ethoxy]ethoxy]ethoxy]ethoxy]ethoxy]ethoxy]ethoxy]ethoxy]ethoxy]ethyl]propionamide (16.5 mg, 23.2 μmol, Eq. 10) resulting in Chitosan Derivative N (1.4%, 65.3 nmol/mg, N 4.05 μmol/mg).

Cs(NM)-Pr—S-Peg12 (5.3% Loading) (Chitosan Derivative O)

The product (a white fibrous solid, 7 mg) was prepared by a procedure similar to that used for the preparation of Chitosan Derivative D. However, in this procedure, Cs(NM)-Pr—SH (6.1%) (25.5 mg, 300.1 nmol/mg, 7.65 μmol) is reacted with a PEG reagent which lacks any targeting element and terminates with a methoxy group: 3-(2,5-dioxo-2,5-dihydropyrrol-1-yl)-N-[2-[2-[2-[2-[2-[2-[2-[2-[2-[2-[2-[2-methoxyethoxy]ethoxy]ethoxy]ethoxy]

ethoxy]ethoxy]ethoxy]ethoxy]ethoxy]ethoxy]ethoxy]ethyl]propionamide (27.3 mg, 38.4 µmol, Eq. 5) resulting in Chitosan Derivative O (5.3%, 220 nmol/mg, N 3.39 µmol/mg).

Cs(NM)-Pr—S-Peg12 (9.6% Loading) (Chitosan Derivative F)

The product (a white fibrous solid, 13 mg) was prepared by a similar procedure as Cs(NM)-Pr—S-αvβ3 Ligand 3 (0.3%) except that Cs(NM)-Pr—SH (8.8%) (27.2 mg, 435.4 nmol/mg, 11.8 µmol) is reacted with a PEG reagent which lacks any targeting element and terminates with a methoxy group: 3-(2,5-dioxo-2,5-dihydropyrrol-1-yl)-N-[2-[2-[2-[2-[2-[2-[2-[2-[2-[2-[2-[2-methoxyethoxy]ethoxy]ethoxy]ethoxy]ethoxy]ethoxy]ethoxy]ethoxy]ethoxy]ethoxy]ethoxy]ethyl]propionamide (4.2.9 mg, 60.4 µmol, Eq. 5) resulting in Chitosan Derivative P (9.6%, 353 nmol/mg, N 2.82 µmol/mg).

VLA-4 (α4β1) Binding Assay

Chitosan covalently linked with small molecule α4β1 antagonists having the general structure of formula IA below were assessed for their α4β1 (VLA-4) binding affinity:

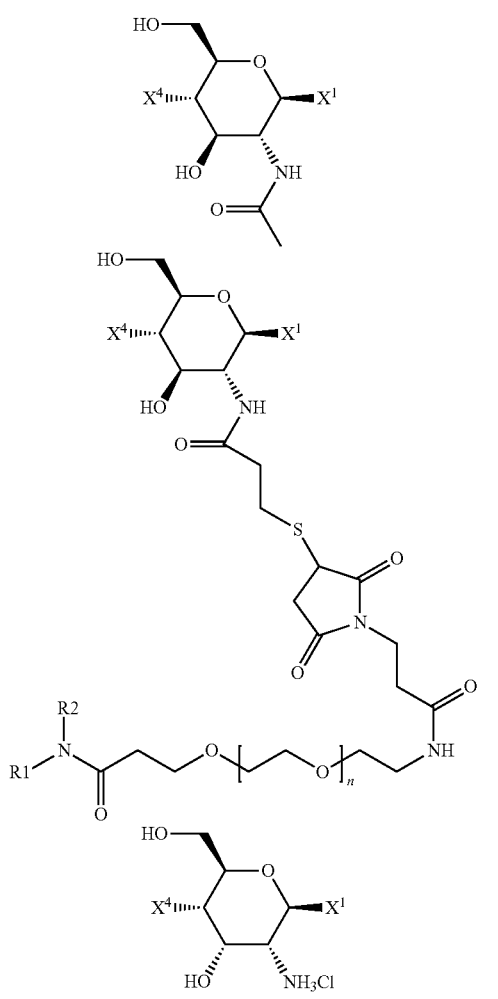

IA wherein R1 is:

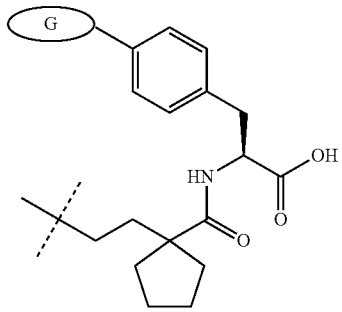

and wherein the remaining variables are as defined in Formula I.

The following adhesion assay has been reported previously and used in this invention with minor modification. See U.S. Pat. Nos. 6,229,011 and 6,380,387 both of which are incorporated herein by reference in their entirety. The functional in vitro potency of the chitosan polymer derivatives linked to VLA-4 (α4β1) targeting compounds (from the examples) were determined using a Jurkat cell-based assay (below) since Jurkat cells express high levels of VLA-4 on their membrane surface. Each assay was conducted in a 96-well plate with VCAM-1 used as the counter ligand for the cells (i.e., VCAM-1 was bound to the surface of the wells).

More specifically, 96-well high-binding F96 Maxisorp immuno microtiter plates (Nunc) were coated overnight with 25 ng/well of VCAM-1. On the day of the experiment, plates were blocked for 1 hour with PBS buffer containing 1% nonfat dry milk to eliminate nonspecific binding. The plates were then washed with DPBS (Dulbecco's Phosphate Buffered Saline) and blotted dry. Any excess liquid was carefully aspirated from the wells.

As a control, a small molecule antagonist (27):

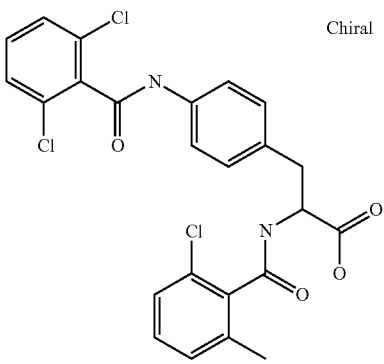

27 for inhibiting VLA-4 was added to control wells in buffer containing 4% DMSO and diluted down the plate, typically in a concentration range of 1000 nM to 0.2 nM. Jurkat Clone E6-1 cells (ATCC) were labeled with 100 µg/ml 6-carboxyfluorescein diacetate, a, fluorescent dye, and then activated with RPMI 1640 medium containing 0.5 mM of the divalent cation $Mn^{2+}$ and 0.05% bovine serum albumin. It is noted that this activation is needed to achieve maximal binding for the ligand may simulate the activation of integrins by cytokines and chemokines in vivo. The control compound (27) was determined to have an $IC_{50}$ of about 12 nM (i.e. 50% of the cells did not bind to VCAM-1 on the surface of the wells since the VLA-4 receptors of the cells were presumably bound to or associated with the control compound).

To assess VLA-4 inhibition by the VLA-4 targeted chitosans (from the examples), Jurkat cells (expressing high levels of VLA-4) were added to the VCAM-1-coated plates to a final concentration of $2 \times 10^5$ cells/well in 96-well plates and allowed to incubate with the test chitosans (from the examples) for 45 minutes at 37° C. After removing unbound cells by gently washing the wells with PBS, the fluorescence signal from the bound cells was read on a Tecan Safire2 microplate reader at 450 nm. Points were plotted and the $IC_{50}$s of each derivatized chitosan polymer were determined by regression analysis using the linear portion of the concentration-response curve. These results are shown below in the Table 1:

TABLE 1

| RO # | Source of chitosan | DA (%) | Small molecule | n | DS (%) | N nmol/mg | Ligand nmol/mg | Binding $IC_{50}$ (nM) |
|---|---|---|---|---|---|---|---|---|
| Chitosan Derivative I | Protasan >10 KDa | 14 | VLA4 Ligand 1 | 8 | 20 | 1.4 | 480 | 17 |
| Chitosan Derivative J | Protasan >10 KDa | 14 | VLA4 Ligand 3 | 8 | 18 | 1.5 | 444 | 22 |
| Chitosan Derivative K | Protasan >10 KDa | 14 | VLA4 Ligand 2 | 24 | 1 | 3.1 | 144 | >1000 |
| Control (27) | | | Small molecule | | | | | 4 |
| Underivatized chitosan | Protasan >10 KDa | | None | | | | | >1000 |

Alpha-V-Beta-3 (αVβ3) Binding Assay

Chitosan covalently linked with small molecule αVβ3 antagonists having the general structure of formula IA below were assessed for their αVβ3 binding affinity:

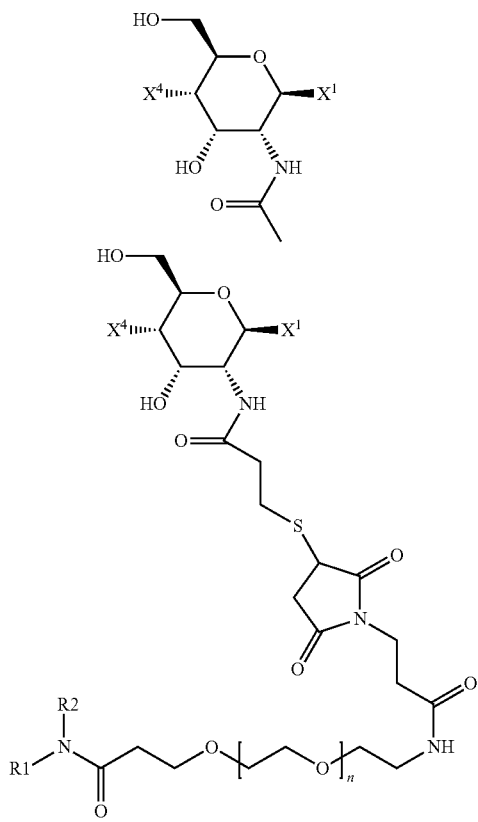

IA

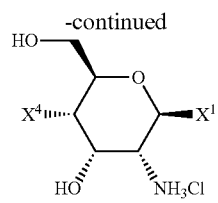

-continued wherein R1 is:

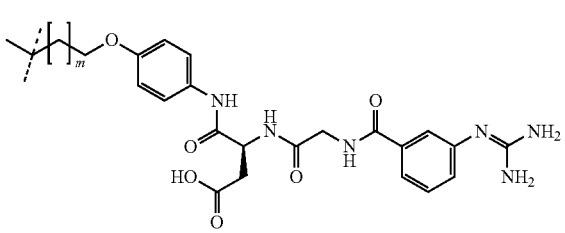

and wherein the remaining variables are as defined in Formula I.

Human αVβ3 Solid Phase Assay:

Immuno 96-well Plates (NUNC, Part #439454) were coated with avβ3 (R & D, Cat #3050-AV) by adding 100 uL of avβ3 (1×) to each well and incubating the plates overnight at 4° C. Buffer used was Buffer A: 20 mM Tris, 150 mM NaCl, 1 mM $CaCl_2$, 1 mM $MgCl_2$, pH 7.4. After removal of the coating reagent, 150 uL of 3.5% BSA in Buffer A was added to each well to block the plates for 105 minutes at 37° C. After blocking, plates were washed 5 times with 200 uL of Buffer B (Buffer A+1 mM MnCl2). 50 uL of compound solution (2×) in 5% DMSO and 50 uL of fibrinogen (2×) (Innovative Research, Cat #IFIB) were then added to each well. Plates were shaken for 2 minutes, and then incubated for 2 hours for 37° C. After the plates were washed 5 times with 200 uL of Buffer B, the $1^{st}$ antibody rabbit anti-human fibrinogen (Innovative Research, Cat IASHFBGN-GF) in the amount of 100 uL/well, and the 2$^{nd}$ antibody Goat anti-rabbit IgG Horse-radish peroxidease conjugate (Invitrogen, Cat #G21234) in the amount of 50 uL/well were added to plates, respectively. After the addition of 1$^{st}$ antibody and after the addition of 2$^{nd}$ antibody, plates were shaken for 2 minutes and incubated for 60 minutes at 37° C., and then washed 5 times with 200 uL of Buffer B correspondingly. The final conditions of the solid phase assay were: [αvβ3]=1.25 ug, [fibrinogen]=0.75 ug/mL, [Anti-FG]=1/2400 (diluted), [HPR-Anti-rabbit]=1/1000 (diluted). When the binding assay was completed, 100 uL/well of detection reagent ABTS (mixture of reagent A and reagent B) (KPL, Cat #50-62-00) was added to plates. Plates were shaken at RT for 5-8 min, and the development of a green color was gradually showing. After being added 100 uL/well Stop Buffer (1.0 M Phosphoric Acid (HPO4)), plates were read on Envision at Absorbance mode 450 nm. A control compound (28) was determined to have an IC$_{50}$ of about 2 nM (i.e. 50% of the cells did not bind to αVβ3 on the surface of the wells since the αVβ3 receptors of the cells were presumably bound to or associated with the control compound):

28

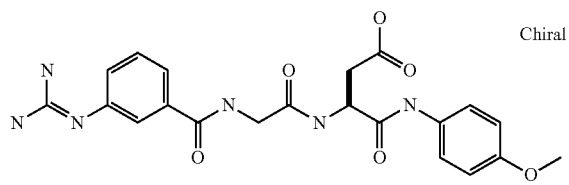

Chiral

The results are shown below in Table 2.

mRNA of the housekeeping gene AHA1 was used in an assay to test its ability to knockdown its expression according to the following method in A549, KB and MDA-MB0435 cells (since such cells are useful for the evaluation of putative anti-cancer activities).

Materials and Methods
siRNA: siAHA at 30 nM
Cells: A549, KB, MDA-MB435

Transfection reagent: Chitosan resuspended in 0.2M Sodium Acetate, ph 5.5, to N/P weight ratio in mg/ml as indicated in the table below. Vials were placed on shakers overnight. A ten-fold concentration stock solution of chitosan solution in 0.2M Sodium Acetate, ph 5.5, was made. Similarly, a ten-fold concentration of stock solution siRNA in OptiMEM was made. Equal volumes of the chitosan and siRNA were combined to make 5× siRNA/chitosan complexes in a 24 well plate which was mixed on a shaker for two hours.

Forward transfection: Cells were plated into 96-wells with 7×10$^4$ cells/mL with 80 ul per well giving a final concentration of 5×10$^3$ cells per well in media containing 10% serum. These plates were incubated overnight at 37° C. At this time, 20 ul of the siRNA/chitosan complex was transferred to the plated cells. The plated cells were then incubated for 48 hrs at 37° C.

The efficacy of siRNA knock-down was measured with the Quanti Gene (QG) Assay as reported by the vendor. A Quanti Gene Cell viability (CV) test was performed on cells with cell titer glow from the same well used for the Quantigene assay (from Panomics of Affymetrix, Santa Clara, Calif.). The results are shown Table 3 and FIGS. 1, 2, and 3.

Figure 2:
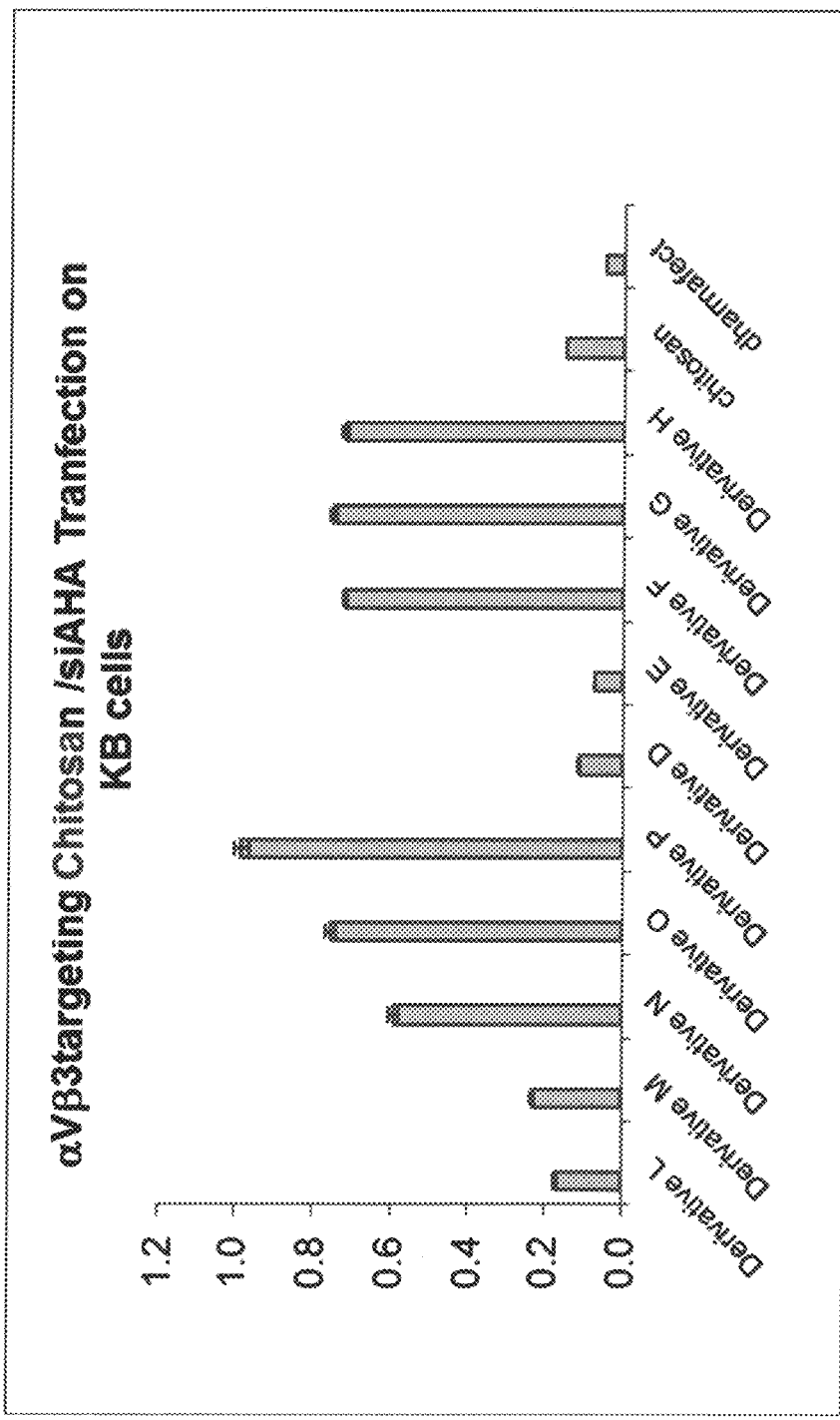
FIG. 2 shows a bar graph of Aha1 mRNA knockdown in KB cells (relative to GAPDAH RNA as a control) with chitosan-siRNA nanoparticles in which the chitosans were covalently derivatized with a αVβ3 small molecule antagonist. The chitosans vary by the degree to which the small molecule has been loaded to available reactive amino termini of the chitosan oligomer prior to complexation with siRNA.
Figure 3:
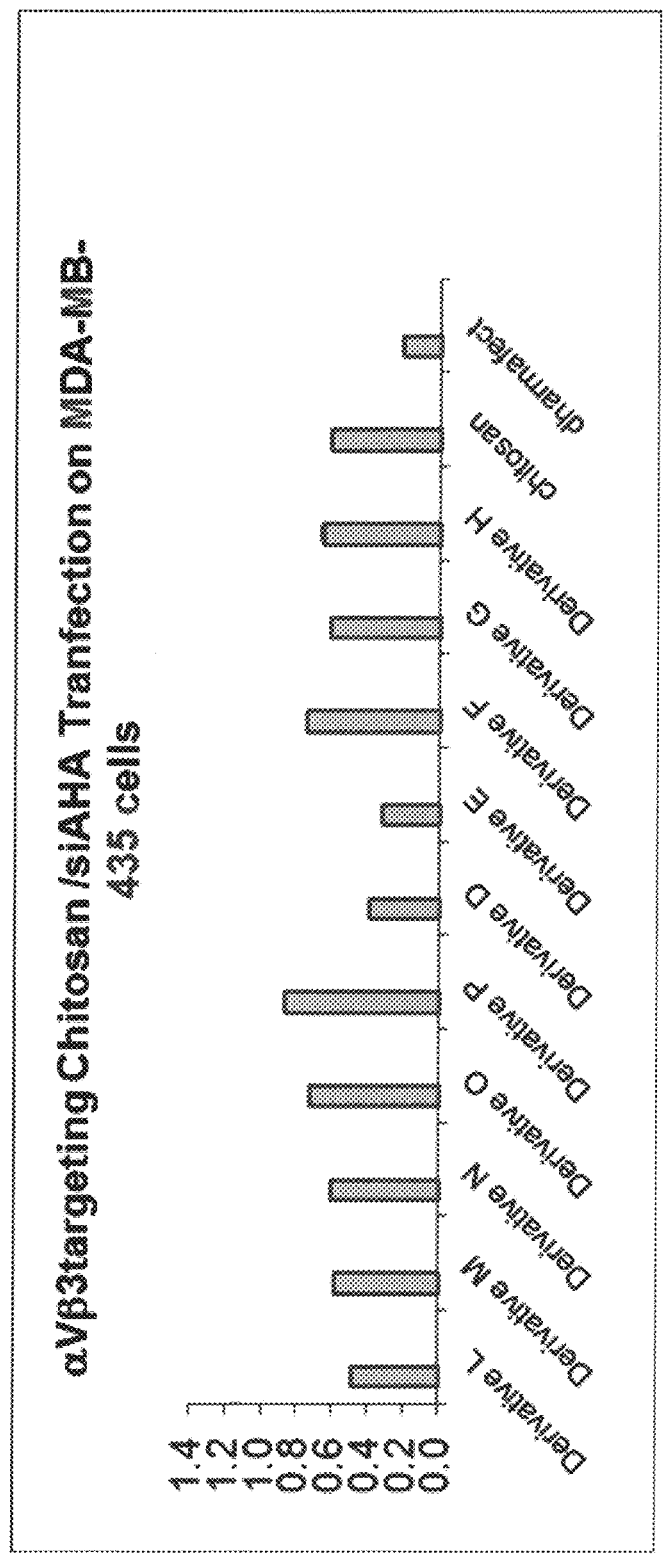
FIG. 3 shows a bar graph of Aha1 mRNA knockdown in MDA-MB-435 cells (relative to GAPDAH RNA as a control) with chitosan-siRNA nanoparticles in which the chitosans were covalently derivatized with a αVβ3 small molecule antagonist. The chitosans vary by the degree to which the small molecule has been loaded to available reactive amino termini of the chitosan oligomer prior to complexation with siRNA.

FIGS. 1, 2, and 3 show the reduction of AHA1 expression in A549, KB and MDA MB-54 cells when treated with siRNA nanoparticles created by combination of siRNA and derivatized chitosans. The y-axis indicates the observed

TABLE 2

| RO # | Source of chitosan | DA (%) | Small molecule | n | DS (%) | N μmol/mg | Ligand nmol/mg | Binding IC$_{50}$ (μM) |
|---|---|---|---|---|---|---|---|---|
| Chitosan Derivative A | AK Scientific (K638) | 2.5 | αvβ3 Ligand 2 | 3 | 0.15 | 4.9 | 7.5 | 0.155 |
| Chitosan Derivative B | AK Scientific (K638) | 2.5 | αvβ3 Ligand 2 | 3 | 0.21 | 4.8 | 11 | 0.016 |
| Chitosan Derivative C | AK Scientific (K638) | 2.5 | αvβ3 Ligand 2 | 3 | 0.76 | 4.7 | 37 | 0.0056 |
| Chitosan Derivative D | NovaMatrix 80/20 B | 14 | αvβ3 Ligand 3 | 2 | 0.3 | 4.24 | 14.8 | 0.0180 |
| Chitosan Derivative E | NovaMatrix 80/20 B | 14 | αvβ3 Ligand 3 | 2 | 0.6 | 4.14 | 29.1 | 0.0254 |
| Chitosan Derivative F | NovaMatrix 80/20 B | 14 | αvβ3 Ligand 3 | 2 | 2 | 3.74 | 89.1 | 0.0025 |
| Chitosan Derivative G | NovaMatrix 80/20 B | 14 | αvβ3 Ligand 3 | 2 | 6 | 2.89 | 217 | 0.0008 |
| Chitosan Derivative H | NovaMatrix 80/20 B | 14 | αvβ3 Ligand 3 | 2 | 5.3 | 3.02 | 198 | 0.0008 |
| Protasan Chitosan | NovaMatrix 80/20 B | | | | 15 | | | >1000 |
| 28 | | | αVβ3 small molecule | | | | | 0.002 |

Assay of siRNA Nanoparticles Formed with Chitosans Covalently Linked with Small Molecule Integrin Antagonist for Knock-Down of AHA1 mRNA in Cellular Systems Chitosan covalently linked with small molecule integrin antagonist for targeted delivery of siRNA were evaluated in several systems for their efficacy to facilitate intracellular knock-down of targeted RNA messages. siRNA targeting the expression level of AHA1. The lower bar indicates a greater degree of knock-down (a higher degree of siRNA transfection); a high bar, a lesser degree of knock-down (i.e., a lesser degree of siRNA transfection). Chitosan Derivatives L, M, N, O, and P do not contain targeting ligand; rather the derivatization terminates in PEG. Chitosan Derivatives L, M, N, O, and P differ by the extent to which this PEG modification has been installed: 0.14%, 0.83%, 1.4%, 5.3%, and 9.6%, respectively. Chitosan Derivatives D, E, F, G, and H contain the αVβ3 targeting Ligand 3, which has been installed to the following levels: 0.3%, 0.6%, 2%, 6% and 5%, respectively. According to these knock-down data, in A549 and MDA MB-549, α'Vβ3-derivatized chitosans Chitosan Derivative D and Chitosan Derivative E are more efficacious than those chitosan that are derivatized with PEG linkers alone at any derivatization percentage. Both αVβ3-derivatized chitosans Chitosan Derivative D and Chitosan Derivative E are also more efficacious than unmodified chitosan. In KB cells, αVβ3-derivatized chitosans Chitosan Derivative D and Chitosan Derivative E are relatively more efficacious than other chitosan preparations. Dharmafect is a commercially available transfection reagent that is a widely used transfection agent.

TABLE 3

| Chitosan Identifier | Original Source (Vendor) | Acetylation (% AA) | Modification | N+ | N/P ratio | comments |
|---|---|---|---|---|---|---|
| Protasan Chitosan | Protasan | 15 | None | 5.07 | 20 | Parent chitosan |
| Chitosan Derivative L | NovaMatrix 80/20 B | 14 | Pr—S-Mal-PEG12-OMe(0.14%) | 4.3 | 20 | Control for alpha v beta 3 targeted |
| Chitosan Derivative M | NovaMatrix 80/20 B | 14 | Pr—S-Mal-PEG12-OMe(0.83%) | 4.2 | 20 | Control for alpha v beta 3 targeted |
| Chitosan Derivative N | NovaMatrix 80/20 B | 14 | Pr—S-Mal-PEG12-OMe(1.4%) | 4.1 | 20 | Control for alpha v beta 3 targeted |
| Chitosan Derivative O | NovaMatrix 80/20 B | 14 | Pr—S-Mal-PEG12-OMe(5.3%) | 3.4 | 20 | Control for alpha v beta 3 targeted |
| Chitosan Derivative P | NovaMatrix 80/20 B | 14 | Pr—S-Mal-PEG12-OMe(9.6%) | 2.8 | 20 | Control for alpha v beta 3 targeted |
| Chitosan Derivative D | NovaMatrix 80/20 B | 14 | αvβ3 Ligand 3 (0.3%) | 4.24 | 20 | αvβ3, 0.3%, 14.8 nmol/mg |
| Chitosan Derivative E | NovaMatrix 80/20 B | 14 | αvβ3 Ligand 3 (0.6%) | 4.14 | 20 | αvβ3, 0.6%, 29.1 nmol/mg |
| Chitosan Derivative F | NovaMatrix 80/20 B | 14 | αvβ3 Ligand 3 (2.0%) | 3.74 | 20 | αvβ3, 2%, 89.1 nmol/mg |
| Chitosan Derivative G | NovaMatrix 80/20 B | 14 | αvβ3 Ligand 3 (6.0%) | 2.89 | 20 | αvβ3, 6%, 217 nmol/mg |
| Chitosan Derivative H | NovaMatrix 80/20 B | 14 | αvβ3 Ligand 3 (5.0%) | 3.02 | 20 | αvβ3, 5.3%, 198 nmol/mg |

The invention claimed is:

1. A pharmaceutical composition, comprising:
Cs(AK)—Pr—S-αvβ3 Ligand 2 (Chitosan Derivative A), 2.5% N-acetyl-chitosan loaded with 0.15% of (S)—N-[4-[3-[3-[2-[2-[2-[2-[2-[2-[2-[2-[2-[2-[2-[3-(2,5-di-oxo-2,5-dihydro-pyrrol-1-yl)-propionylamino]ethoxy] ethoxy]ethoxy]ethoxy]ethoxy]ethoxy]ethoxy] ethoxy]ethoxy]ethoxy]ethoxy]-1-oxopropyl]amino] propoxy]-phenyl]-3-[2-[3-[guanidino]-benzoylamino]-acetylamino]-succinamic acid;
Cs(AK)—Pr—S-αvβ3 Ligand 2 (Chitosan Derivative B), 2.5% N-acetyl-chitosan loaded with 0.21% of (S)—N-[4-[3-[3-[2-[2-[2-[2-[2-[2-[2-[2-[2-[2-[2-[3-(2,5-di-oxo-2,5-dihydro-pyrrol-1-yl)-propionylamino]ethoxy] ethoxy]ethoxy]ethoxy]ethoxy]ethoxy]ethoxy] ethoxy]ethoxy]ethoxy]ethoxy]-1-oxopropyl]amino] propoxy]-phenyl]-3-[2-[3-[guanidino]-benzoylamino]-acetylamino]-succinamic acid;
Cs(AK)—Pr—S-αvβ3 Ligand 2 (Chitosan Derivative C), 2.5% N-acetyl-chitosan loaded with 0.76% of (S)—N-[4-[3-[3-[2-[2-[2-[2-[2-[2-[2-[2-[2-[2-[2-[3-(2,5-di-oxo-2,5-dihydro-pyrrol-1-yl)-propionylamino]ethoxy] ethoxy]ethoxy]ethoxy]ethoxy]ethoxy]ethoxy] ethoxy]ethoxy]ethoxy]ethoxy]-1-oxopropyl]amino] propoxy]-phenyl]-3-[2-[3-[guanidino]-benzoylamino]-acetylamino]-succinamic acid;
Cs(NM)-Pr—S-αvβ3 Ligand 3 (Chitosan Derivative D), 14% N-acetyl-chitosan loaded with 0.3% of (S)—N-[4-[3-[3-[2-[2-[2-[2-[2-[2-[2-[2-[2-[2-[2-[3-(2,5-di-oxo-2,5-dihydro-pyrrol-1-yl)-propionylamino]ethoxy] ethoxy]ethoxy]ethoxy]ethoxy]ethoxy]ethoxy]ethoxy] ethoxy]ethoxy]ethoxy]ethoxy]-1-oxopropyl]amino] ethoxy]-phenyl]-3-[2-[3-[guanidino]-benzoylamino]-acetylamino]-succinamic acid;
Cs(NM)-Pr—S-αvβ3 Ligand 3 (Chitosan Derivative E), 14% N-acetyl-chitosan loaded with 0.6% of (S)—N-[4-[3-[3-[2-[2-[2-[2-[2-[2-[2-[2-[2-[2-[2-[3-(2,5-di-oxo-2,5-dihydro-pyrrol-1-yl)-propionylamino]ethoxy] ethoxy]ethoxy]ethoxy]ethoxy]ethoxy]ethoxy]ethoxy] ethoxy]ethoxy]ethoxy]ethoxy]-1-oxopropyl]amino] ethoxy]-phenyl]-3-[2-[3-[guanidino]-benzoylamino]-acetylamino]-succinamic acid;
Cs(NM)-Pr—S-αvβ3 Ligand 3 (Chitosan Derivative F), 14% N-acetyl-chitosan loaded with 1.9% of (S)—N-[4-[3-[3-[2-[2-[2-[2-[2-[2-[2-[2-[2-[2-[2-[3-(2,5-di-oxo-2,5-dihydro-pyrrol-1-yl)-propionylamino]ethoxy] ethoxy]ethoxy]ethoxy]ethoxy]ethoxy]ethoxy]ethoxy] ethoxy]ethoxy]ethoxy]ethoxy]-1-oxopropyl]amino] ethoxy]-phenyl]-3-[2-[3-[guanidino]-benzoylamino]-acetylamino]-succinamic acid;
Cs(NM)-Pr—S-αvβ3 Ligand 3 (Chitosan Derivative G), 14% N-acetyl-chitosan loaded with 6% of (S)—N-[4-[3-[3-[2-[2-[2-[2-[2-[2-[2-[2-[2-[2-[2-[3-(2,5-di-oxo-2,5-dihydro-pyrrol-1-yl)-propionylamino]ethoxy] ethoxy]ethoxy]ethoxy]ethoxy]ethoxy]ethoxy] ethoxy]ethoxy]ethoxy]ethoxy]-1-oxopropyl]amino] ethoxy]-phenyl]-3-[2-[3-[guanidino]-benzoylamino]-acetylamino]-succinamic acid;
Cs(NM)-Pr—S-αvβ3 Ligand 3 (Chitosan Derivative H), 14% N-acetyl-chitosan loaded with 5.0% of (S)—N-[4-[3-[3-[2-[2-[2-[2-[2-[2-[2-[2-[2-[2-[2-[3-(2,5-di-oxo-2,5-dihydro-pyrrol-1-yl)-propionylamino]ethoxy] ethoxy]ethoxy]ethoxy]ethoxy]ethoxy]ethoxy]ethoxy] ethoxy]ethoxy]ethoxy]ethoxy]-1-oxopropyl]amino] ethoxy]-phenyl]-3-[2-[3-[guanidino]-benzoylamino]-acetylamino]-succinamic acid;
Cs(NM)-Pr—S-VLA$_4$ Ligand 1 (Chitosan Derivative I), 14% N-acetyl-chitosan derivatized with 20% of (S)-3-

[4-(2,6-dichlorobenzoylamino)phenyl]-2-[[[1-[2-[3-[2-[2-[2-[2-[2-[2-[2-[2-[3-(2,5-dioxo-2,5-dihydropyrrol-1-yl)propionylamino]-ethoxy]ethoxy]ethoxy]ethoxy]ethoxy]ethoxy]ethoxy]ethoxy]propionylamino]ethyl]cyclopentyl]carbonyl]amino]propionic acid;

Cs(NM)-Pr—S-$VLA_4$ Ligand 3 (Chitosan Derivative J), 14% N-acetyl-chitosan derivatized with 18% of (S)-2-[4-[(3-[2-[2-[2-[2-[2-[2-[2-[2-[3-(2,5-Dioxo-2,5-dihydropyrrol-1-yl)propionylamino]ethoxy]ethoxy]ethoxy]ethoxy]ethoxy]ethoxy]ethoxy]ethoxy]propionylamino)methyl]-2,6-difluorobenzoylamino]-3-[4-(1,3,6-trimethyl-2,4-dioxo-1,2,3,4-tetrahydropyrimidin-5-yl)phenyl]propionic acid; or Cs(NM)-$VLA_4$ Ligand 2 Acid (4% Loading) (Chitosan Derivative K), 14% N-acetyl-chitosan derivatized with 4% of N-[2-[2-[2-[2-[2-[2-[2-[2-[2-[2-[2-[2-[2-[2-[2-[2-[2-[2-[2-[2-[2-[2-[2-[2-[1-(S)-1-carboxy-2-[4-(2,6-dichlorobenzoylamino)phenyl]ethylcarbamoyl]cyclopentyl]ethylcarbamoyl]ethoxy]ethoxy]ethoxy]ethoxy]ethoxy]ethoxy]ethoxy]ethoxy]ethoxy]ethoxy]ethoxy]ethoxy]ethoxy]ethoxy]ethoxy]ethoxy]ethoxy]ethoxy]ethoxy]ethoxy]ethoxy]ethoxy]ethoxy]ethoxy]ethyl]succinamic acid.

2. The pharmaceutical composition according to claim 1, further comprising a pharmaceutically acceptable carrier or excipient.

3. A method of inhibiting VLA-4, said method comprising the step of administering a therapeutically effective amount of the pharmaceutical composition according to claim 1 to a patient in need thereof.

* * * * *